US011852970B2

(12) United States Patent
Kudo et al.

(10) Patent No.: US 11,852,970 B2
(45) Date of Patent: Dec. 26, 2023

(54) MATERIAL FOR LITHOGRAPHY, PRODUCTION METHOD THEREFOR, COMPOSITION FOR LITHOGRAPHY, PATTERN FORMATION METHOD, COMPOUND, RESIN, AND METHOD FOR PURIFYING THE COMPOUND OR THE RESIN

(71) Applicants: Mitsubishi Gas Chemical Company, Inc., Tokyo (JP); A SCHOOL CORPORATION KANSAI UNIVERSITY, Suita (JP)

(72) Inventors: Hiroto Kudo, Suita (JP); Masatoshi Echigo, Tokyo (JP); Takumi Toida, Hiratsuka (JP); Takashi Sato, Hiratsuka (JP)

(73) Assignees: Mitsubishi Gas Chemical Company, Inc., Tokyo (JP); A School Corporation Kansai University, Osaka (JP)

( * ) Notice: Subject to any disclaimer, the term of this patent is extended or adjusted under 35 U.S.C. 154(b) by 0 days.

(21) Appl. No.: 15/754,794

(22) PCT Filed: Aug. 23, 2016

(86) PCT No.: PCT/JP2016/074563
§ 371 (c)(1),
(2) Date: Feb. 23, 2018

(87) PCT Pub. No.: WO2017/033943
PCT Pub. Date: Mar. 2, 2017

(65) Prior Publication Data
US 2018/0246405 A1 Aug. 30, 2018

(30) Foreign Application Priority Data

Aug. 24, 2015 (JP) .................................. 2015-165305

(51) Int. Cl.
*G03F 7/004* (2006.01)
*C07C 395/00* (2006.01)
*G03F 7/039* (2006.01)
*G03F 7/20* (2006.01)
*G03F 7/038* (2006.01)

(52) U.S. Cl.
CPC .......... *G03F 7/0045* (2013.01); *C07C 395/00* (2013.01); *G03F 7/004* (2013.01); *G03F 7/038* (2013.01); *G03F 7/039* (2013.01); *G03F 7/0382* (2013.01); *G03F 7/0395* (2013.01); *G03F 7/0397* (2013.01); *G03F 7/20* (2013.01)

(58) Field of Classification Search
CPC ........ G03F 7/0045; G03F 7/039; G03F 7/004; G03F 7/038; G03F 7/0382; G03F 7/0395; G03F 7/0397; G03F 7/20; G03F 7/016; G03F 7/26; C07C 395/00; C08G 79/00; C08G 85/002
See application file for complete search history.

(56) References Cited

U.S. PATENT DOCUMENTS

| 4,152,155 | A | 5/1979 | Lelental et al. |
| 4,370,497 | A * | 1/1983 | Barton .................... C07C 46/06 560/126 |
| 4,379,827 | A | 4/1983 | Hallman |
| 4,460,408 | A | 7/1984 | Badesha et al. |
| 4,480,113 | A | 10/1984 | Brill |
| 4,613,468 | A | 9/1986 | Sandman et al. |
| 5,024,927 | A | 6/1991 | Yamada et al. |
| 5,928,886 | A * | 7/1999 | Logan ............. G01N 33/54386 435/7.92 |
| 2004/0214103 | A1 | 10/2004 | Araki et al. |
| 2005/0048248 | A1 | 3/2005 | Ito et al. |
| 2005/0255712 | A1 | 11/2005 | Kato et al. |
| 2005/0271978 | A1 | 12/2005 | Takeda et al. |
| 2006/0257781 | A1 | 11/2006 | Benoit et al. |
| 2008/0153031 | A1 | 6/2008 | Echigo et al. |
| 2010/0316950 | A1 | 12/2010 | Oguro et al. |
| 2011/0104595 | A1* | 5/2011 | Hayashi ................ B82Y 10/00 430/5 |
| 2012/0171611 | A1 | 7/2012 | Ideno et al. |
| 2013/0011630 | A1 | 1/2013 | Sullivan et al. |
| 2014/0248561 | A1 | 9/2014 | Echigo et al. |

(Continued)

FOREIGN PATENT DOCUMENTS

EP 1511026 A2 3/2005
EP 2743769 A1 6/2014

(Continued)

OTHER PUBLICATIONS

Serguievski et al, Organometallics, Electronic Substituent Effects in Quenching of 1O2 by Diaryl Tellurides , 1997, 16, 4386-4391. (Year: 1997).*
Diaz et al. (Poly(tetrahalo-p-phenylenechalcogenide)s: synthesis and properties, pp. 2454-2455, Published Nov. 1992) (Year: 1992).*
WO2017/188450 translation (Year: 2017).*
Petragnani (Aryl tekkurium Trihalides-II Condensation Reaction With Methylketones and Aromatic Compounds Containing Electron-Repelling Groups, Tetrahedron, vol. 12, pp. 219-225) (Year: 1961).*
Tardigrade (p. 1-7, published 2021) (Year: 2021).*
Emeleus et al. (The Alkyl- and Aryl-substituted Fluorides of Sulphur, Selenium, Tellurium, and Iodide, pp. 1126-1131, Published 1946) (Year: 1946).*
Maksimenko et al. (Reaction of Diaryl Telluroxides with HBF4, Short Communications, Russian Journal of Organic Chemistry, vol. 38, p. 1812, Published 2002) (Year: 2002).*

(Continued)

*Primary Examiner* — Yevgeny Valenrod
*Assistant Examiner* — Blaine G Doletski
(74) *Attorney, Agent, or Firm* — Fitch, Even, Tabin & Flannery LLP

(57) ABSTRACT

A material for lithography containing a tellurium-containing compound or a tellurium-containing resin, a production method therefor, a composition for lithography, a pattern formation method, a compound, a resin, and a method for purifying the compound or the resin are provided. The compounds and materials can provide for high solubility in a safe solvent.

11 Claims, No Drawings

(56) References Cited

U.S. PATENT DOCUMENTS

| | | | |
|---|---|---|---|
| 2014/0363957 A1 | 12/2014 | Hatakeyama et al. | |
| 2015/0090691 A1 | 4/2015 | Echigo et al. | |
| 2015/0099228 A1 | 4/2015 | Tatakeyama et al. | |
| 2015/0192851 A1 | 7/2015 | Yamashita et al. | |
| 2015/0376157 A1 | 12/2015 | Echigo et al. | |
| 2017/0073288 A1 | 3/2017 | Makinoshima et al. | |
| 2017/0242338 A1* | 8/2017 | Hirano | G03F 7/322 |
| 2018/0246405 A1 | 8/2018 | Kudo et al. | |
| 2020/0249573 A1* | 8/2020 | Toida | G03F 7/11 |
| 2020/0262787 A1* | 8/2020 | Echigo | G02B 1/04 |
| 2021/0018841 A1 | 1/2021 | Sato et al. | |
| 2021/0116813 A1 | 4/2021 | Sato et al. | |

FOREIGN PATENT DOCUMENTS

| | | | |
|---|---|---|---|
| EP | 3343290 | | 7/2018 |
| JP | 52019516 | * | 2/1977 |
| JP | S52-019516 A | | 2/1977 |
| JP | 144322 | * | 12/1978 |
| JP | S53-144322 A | | 12/1978 |
| JP | S57-082238 A | | 5/1982 |
| JP | S64-082040 A | | 3/1989 |
| JP | H02039156 | | 2/1990 |
| JP | H07165947 | | 6/1995 |
| JP | H10048831 | | 2/1998 |
| JP | H10-063002 A | | 3/1998 |
| JP | 2002334869 | | 11/2002 |
| JP | 2004177668 | | 6/2004 |
| JP | 2004271838 | | 9/2004 |
| JP | 2005-071488 A | | 3/2005 |
| JP | 2005-128049 A | | 5/2005 |
| JP | 2005250434 | | 9/2005 |
| JP | 2005-326838 A | | 11/2005 |
| JP | 2005-344009 A | | 12/2005 |
| JP | 2007-199653 A | | 8/2007 |
| JP | 2007-526496 A | | 9/2007 |
| JP | 2007226170 | | 9/2007 |
| JP | 2007226204 | | 9/2007 |
| JP | 2008-145539 A | | 6/2008 |
| JP | 2008-163242 A | | 7/2008 |
| JP | 2008-308691 A | | 12/2008 |
| JP | 2009-173623 A | | 8/2009 |
| JP | 2010138393 | | 6/2010 |
| JP | 2013-185009 A | | 9/2013 |
| JP | 2014073986 | | 4/2014 |
| JP | 2014185086 | | 10/2014 |
| JP | 2015018223 | | 1/2015 |
| JP | 2015-075500 A | | 4/2015 |
| JP | 2015-108781 A | | 6/2015 |
| JP | 2015-117271 A | | 6/2015 |
| JP | 2015174877 | | 10/2015 |
| JP | 2016012061 | | 1/2016 |
| KR | 10-2017-0038046 A | | 4/2017 |
| TW | 201616221 A | | 5/2016 |
| WO | 2004066377 | | 8/2004 |
| WO | 2009072465 | | 6/2009 |
| WO | 2011034062 | | 3/2011 |
| WO | 2015137486 | | 9/2015 |
| WO | 2017033943 | | 3/2017 |
| WO | 2016/035560 A1 | | 5/2017 |
| WO | WO2017/188450 | * | 11/2017 |
| WO | WO2017/188451 | * | 11/2017 |
| WO | WO2017/188452 | * | 11/2017 |

OTHER PUBLICATIONS

Kudo, (Synthesis and property of novel tellurium containing polymers, Fiscal Year Final Research Report, 6 pages, Published 2013, cited in IDS filed May 26, 2022) (Year: 2013).*

Xu et al., "Dendritic tellurides acting as antioxidants", Chin. Sci. Bull., vol. 51(19) pp. 2315-2321, Published 2006. As cited in IDS filed Apr. 30, 2018). (Year: 2006).*

JP144322 translated (Year: 1978).*

Vessman et al. (Catalytic Antioxidant Activity of Diaryl Tellurides in a Two-Phase Lipid Peroxidation Model, J. Org. Chem. 60, pp. 4461-4467, Published 1995) (Year: 1995).*

Kudo et al. (Synthesis and Property of Tellurium-Containing Polymers Obtained by Simple Condensation Reaction of Tetrachlorotellurium and 1,3-Dimethoxybenzene, Chem. Lett., 40, pp. 762-764, Published 2011) (Year: 2011).*

Klapotke et al. (Spectroscopic and Structural Studies of Polyfluorophenyl Tellurides and Tellurium(IV) Dihalides, Inoganic. Chem., 40, pp. 5169-5176, Published 2001) (Year: 2001).*

Fukunaga, Mari et al., "Synthesis and Property of Tellurium-Containing Polymer for Extreme Ultraviolet Resist Material," Journal of Photopolymer Science and Technology, 2017, vol. 30, No. 1, pp. 103-107.

Kudo, Hiroto et al., "Synthesis and Property of Tellurium-containing Polymers Obtained by Simple Condensation Reaction of Tetrachlorotellurium and 1,3-Dimethoxybenzene," Chemistry Letters, 2011, vol. 40, No. 7, pp. 762-764.

T. Nakayama et al., A New Three-Component Photoresist Based on Calix[4]resorcinarene Derivative, a Cross-linker, and a Photo-acid Generator, Bull. Chem. Soc. Jpn., Dec. 1998, vol. 71, pp. 2979-2984.

Shinji Okazaki et al., Innovation of Photoresist Material Development, CMC Publishing Co., Ltd., Sep. 2009, pp. 211-224 (16 pages).

Xu Huaping, Dendritic Tellurides Acting as Antioxidants, Chinese Science Bulletin, Oct. 2006, vol. 51, No. 19, pp. 2315-2321.

Suzuki Hitomi, Novel Aromatic Azopolymers with Regularly Interposed Tellurium Atoms in the Backbone, Jul. 1995, vol. 128, pp. 703-709.

Jahnke A. et al., Polytellurophenes with Properties Controlled by Tellurium-Coordination, Angew. Chem. Int. Ed., 2010, vol. 49, pp. 10140-10144.

Patra, A. et al., Synthesis, Structure, and Electropolymerization of 3,4-Dimethoxytellurophene: Comparison with Selenium Analogue, Organic Letters, 2009, vol. 11, No. 7, pp. 1487-1490.

Petragnani, N. et al., "A Facile and General Method for the Preparation of Diaryltellurium Dicarboxylates," Journal of Organometallic Chemistry, 1976, vol. 120, pp. 375-380.

Breslow et al., "Multi-sulfur and sulfer oxygen five and six membered heterocycles, Part two," Interscience publishers, 1966, p. 1384 (part of the subject index).

Gioabă et al., "Electron Spin Resonance Spectra and Electronic Structure of Nitro-phenoxatellurin Anion-radicals," Journal of the Chemical Society Perkin II, 1977, pp. 529-532.

Irgolic, "Polymeric Organic Tellurium Compounds," Organotellurium Compounds, 1990, Houben-Weyl Methods of Organic Chemistry, vol. E 12b, pp. 721-725.

Kudo, "Synthesis and property of novel tellurium containing polymers," 2013 Fiscal Year Final Research Report (6 pages).

Sadekov et al., "Organotellurium Compounds in Organic Synthesis," Russian Chemical Reviews, 1987, vol. 56, No. 4, pp. 343-354.

Sato et al., "X-ray Crystallographic Analysis of the Oxytellurium Compunds [10-Te-4(C3O)] and Solvent Effect on the Hypervalency," Organometallics, 1995, vol. 14, No. 11, pp. 5393-5398.

Kudo, Hiroto, "Synthesis and property of novel tellurium containing polymers," 2013 Fiscal Year Final Research Report (6 pages).

Huaping et al., "Dendritic tellurides acting as antioxidants", Chinese Science Bulletin, vol. 51, No. 19 (2006), pp. 2315-2321.

* cited by examiner

MATERIAL FOR LITHOGRAPHY, PRODUCTION METHOD THEREFOR, COMPOSITION FOR LITHOGRAPHY, PATTERN FORMATION METHOD, COMPOUND, RESIN, AND METHOD FOR PURIFYING THE COMPOUND OR THE RESIN

CROSS-REFERENCE TO RELATED APPLICATIONS

This application is a U.S. national phase application filed under 35 U.S.C. § 371 of International Application PCT/JP2016/074563, filed on Aug. 23, 2016, designating the United States, which claims priority from Japanese Application Number 2015-165305, filed Aug. 24, 2015.

Field of the Invention

The present invention relates to a material for lithography, a production method therefor, a composition for lithography, and a pattern formation method. Also, the present invention relates to a compound and a resin which can be used in the resist composition, etc. Moreover, the present invention relates to a method for purifying the compound and the resin.

Background of the Invention

Conventional typical resist materials are polymer based resist materials capable of forming amorphous thin films. Examples include polymer based resist materials such as polymethyl methacrylate, polyhydroxy styrene with an acid dissociation reactive group, and polyalkyl methacrylate. A line pattern of about 45 to 100 nm is formed by irradiating a resist thin film made by coating a substrate with a solution of such a polymer based resist material with ultraviolet, far ultraviolet, electron beam, extreme ultraviolet (EUV), and X-ray or the like.

However, polymer based resist materials have a molecular weight as large as about 10,000 to 100,000 and also wide molecular weight distribution. Therefore, in lithography using a polymer based resist material, roughness occurs on a fine pattern surface; the pattern dimension becomes difficult to be controlled; and the yield decreases. Therefore, there is a limitation in miniaturization with lithography using a conventional polymer based resist material. In order to make a finer pattern, various low molecular weight resist materials have been proposed.

For example, an alkaline development type negative type radiation-sensitive composition (see, for example, Patent Literature 1 (Japanese Patent Application Laid-Open No. 2005-326838) and Patent Literature 2 (Japanese Patent Application Laid-Open No. 2008-145539)) using a low molecular weight polynuclear polyphenolic compound as a main component has been suggested. As a candidate of a low molecular weight resist material having high heat resistance, an alkaline development type negative type radiation-sensitive composition (see, for example, Patent Literature 3 (Japanese Patent Application Laid-Open No. 2009-173623) and Non Patent Literature 1 (T. Nakayama, M. Nomura, K. Haga, M. Ueda: Bull. Chem. Soc. Jpn., 71, 2979 (1998)) using a low molecular weight cyclic polyphenolic compound as a main component has been suggested as well. Moreover, as a base compound of a resist material, a polyphenol compound is known to be capable of imparting high heat resistance despite a low molecular weight and useful for improving the resolution and roughness of a resist pattern (see, for example, Non Patent Literature 2 (Shinji Okazaki et al., "New Trends of Photoresists", CMC Publishing Co., Ltd., September 2009, pp. 211-259)).

Also, lithography with electron beam or extreme ultraviolet (hereinafter, also referred to as "EUV") differ in reaction mechanism from general photolithography. Moreover, lithography with electron beam or EUV aims at forming fine patterns of tens of nm. Accordingly, there is a demand for a resist material having higher sensitivity for an exposing source with decrease in resist pattern dimension. Particularly, lithography with EUV needs to achieve higher sensitivity of a resist composition in terms of throughput.

As resist materials that solve these problems, inorganic resist materials having titanium, hafnium, or zirconium have been proposed (see, for example, Patent Literature 4 (Japanese Patent Application Laid-Open No. 2015-75500) to Patent Literature 5 (Japanese Patent Application Laid-Open No. 2015-108781)).

CITATION LIST

Patent Literature

Patent Literature 1: Japanese Patent Application Laid-Open No. 2005-326838
Patent Literature 2: Japanese Patent Application Laid-Open No. 2008-145539
Patent Literature 3: Japanese Patent Application Laid-Open No. 2009-173623
Patent Literature 4: Japanese Patent Application Laid-Open No. 2015-75500
Patent Literature 5: Japanese Patent Application Laid-Open No. 2015-108781

Non Patent Literature

Non Patent Literature 1: T. Nakayama, M. Nomura, K. Haga, M. Ueda: Bull. Chem. Soc. Jpn., 71, 2979 (1998)
Non Patent Literature 2: Shinji Okazaki et al., "New Trends of Photoresists", CMC Publishing Co., Ltd., September 2009, pp. 211-259

SUMMARY OF INVENTION

However, the heat resistances of the compositions described in Patent Literatures 1 and 2 are not sufficient, and the shapes of the obtained resist patterns are likely to be poor. The solubilities of the compositions described in Patent Literature 3 and Non Patent Literature 1 in safe solvents used in a semiconductor production process are not sufficient. Also, the sensitivities of the compositions described in Patent Literature 3 and Non Patent Literature 1 are not sufficient, the shapes of the obtained resist patterns in some cases are poor, and thus a further improvement of low molecular weight resist materials is desired. Non Patent Literature 2 is silent on solubility, the heat resistances of the described compounds are still not sufficient, and a further improvement of heat resistance is required.

Although the resist materials described in Patent Literatures 4 and 5 have relatively high sensitivity, their sensitivities are still not sufficient. Moreover, the resist materials have disadvantages such as low solubility in safe solvents, poor storage stability, and many defects in films.

An object of the present invention is to provide a material for lithography which can be used in a resist composition, etc. which is capable of reducing film defects (thin film formability), has good storage stability and high sensitivity, and can impart a good shape to a resist pattern, a production method therefor, and a material composition for lithography and a pattern formation method using the material for lithography.

Another object of the present invention is to provide a compound and a resin (for example, a tellurium-containing polyphenol derivative) which have high sensitivity and high solubility in a safe solvent, and a method for purifying the compound or the resin.

The inventors have, as a result of devoted examinations to solve the above problems, found out that a compound and a resin having a specific structure have high solubility in a safe solvent and that a material for lithography containing the compound or the resin, when used as a resist composition, etc. has high sensitivity and can impart a shape to a resist pattern, and reached the present invention.

More specifically, the present invention is as follows.

<1> A material for lithography comprising a tellurium-containing compound or a tellurium-containing resin.

<2> The material for lithography according to <1>, wherein the tellurium-containing compound is represented by the following formula (A-1):

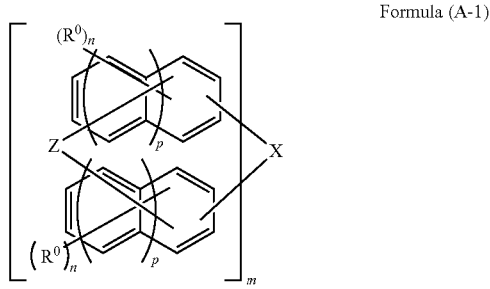

Formula (A-1)

wherein X is a 2m-valent group of 0 to 60 carbon atoms containing tellurium; Z is an oxygen atom, a sulfur atom, or non-crosslinked state; each $R^0$ is independently selected from the group consisting of a monovalent group containing an oxygen atom, a monovalent group containing a sulfur atom, a monovalent group containing a nitrogen atom, a hydrocarbon group, a halogen atom, and a combination thereof; m is an integer of 1 to 4; each p is independently an integer of 0 to 2; and each n is independently an integer of 0 to (5+2×p).

<3> The material for lithography according to <2>, wherein the tellurium-containing compound is represented by the following formula (A-2):

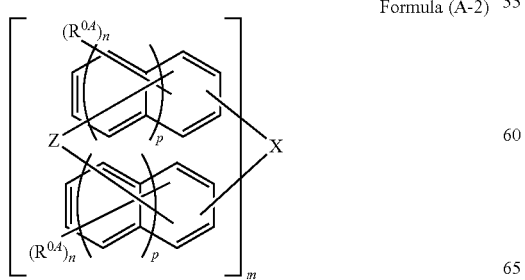

Formula (A-2)

wherein X is a 2m-valent group of 0 to 60 carbon atoms containing tellurium; Z is an oxygen atom, a sulfur atom, a single bond, or non-crosslinked state; each $R^{0A}$ is independently selected from the group consisting of a hydrocarbon group, a halogen atom, a cyano group, a nitro group, an amino group, an alkyl group of 1 to 30 carbon atoms, an alkenyl group of 2 to 30 carbon atoms, an aryl group of 6 to 40 carbon atoms, a hydroxy group or a group in which a hydrogen atom of a hydroxy group is substituted with an acid crosslinking reactive group or an acid dissociation reactive group, and a combination thereof, wherein the alkyl group, the alkenyl group, and the aryl group each optionally have an ether bond, a ketone bond, or an ester bond; m is an integer of 1 to 4; each p is independently an integer of 0 to 2; and each n is independently an integer of 0 to (5+2×p).

<4> The material for lithography according to <2>, wherein the tellurium-containing compound is represented by the following formula (A-3):

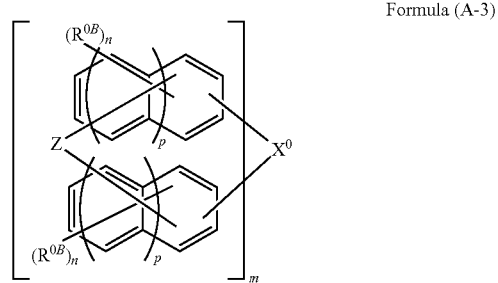

Formula (A-3)

wherein $X^0$ is a 2m-valent group of 0 to 30 carbon atoms containing tellurium; Z is an oxygen atom, a sulfur atom, or non-crosslinked state; each $R^{0B}$ is independently a monovalent group containing an oxygen atom, a monovalent group containing a sulfur atom, a monovalent group containing a nitrogen atom, a hydrocarbon group, or a halogen atom; m is an integer of 1 to 4; each p is independently an integer of 0 to 2; and each n is independently an integer of 0 to (5+2×p).

<5> The material for lithography according to <2>, wherein the tellurium-containing compound is represented by the following formula (1A):

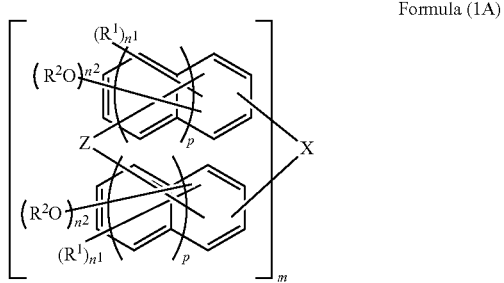

Formula (1A)

wherein X, Z, m, and p are as defined in the above formula (A-1); each $R^1$ is independently selected from the group consisting of a hydrocarbon group, a halogen atom, a cyano group, a nitro group, an amino group, an alkyl group of 1 to 30 carbon atoms, an alkenyl group of 2 to 30 carbon atoms, an aryl group of 6 to 40 carbon atoms, and a combination thereof, wherein the alkyl group, the alkenyl group, and the aryl group each optionally have an ether bond, a ketone bond, or an ester bond; each $R^2$ is independently a hydrogen atom, an acid crosslinking reactive group, or an acid dissociation reactive group; each $n^1$ is independently an integer of 0 to (5+2×p); and each $n^2$ is independently an integer of 0 to (5+2×p), provided that at least one $n^2$ is an integer of 1 to (5+2×p).

<6> The material for lithography according to <4>, wherein the tellurium-containing compound is represented by the following formula (1B):

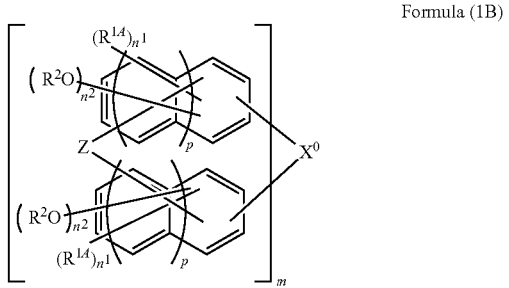

Formula (1B)

wherein $X^0$, Z, m, and p are as defined in the above formula (A-3); each $R^{14}$ is independently an alkyl group, an aryl group, an alkenyl group, or a halogen atom; each $R^2$ is independently a hydrogen atom, an acid crosslinking reactive group, or an acid dissociation reactive group; each $n^1$ is independently an integer of 0 to (5+2×p); and each $n^2$ is independently an integer of 0 to (5+2×p), provided that at least one $n^2$ is an integer of 1 to (5+2×p).

<7> The material for lithography according to <6>, wherein the tellurium-containing compound is represented by the following formula (2A):

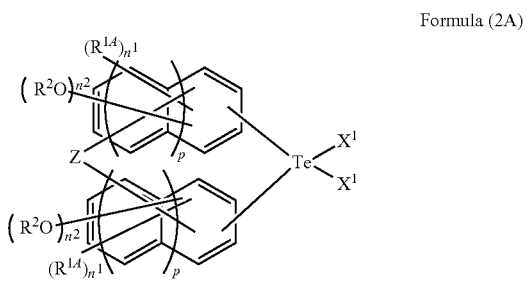

Formula (2A)

wherein Z, $R^{14}$, $R^2$, p, $n^1$, and $n^2$ are as defined in the above formula (1B); and each $X^1$ is independently a monovalent group containing an oxygen atom, a monovalent group containing a sulfur atom, a monovalent group containing a nitrogen atom, a hydrocarbon group, a hydrogen atom, or a halogen atom.

<8> The material for lithography according to [7], wherein the tellurium-containing compound is represented by the following formula (3A):

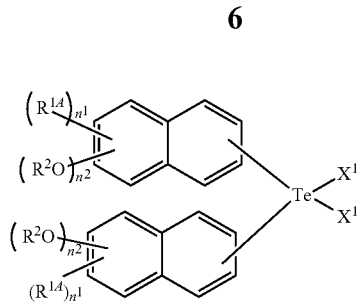

Formula (3A)

wherein $R^{14}$, $R^2$, $X^1$, $n^1$, and $n^2$ are as defined in the above formula (2A).

[9] The material for lithography according to [8], wherein the tellurium-containing compound is represented by the following formula (4A):

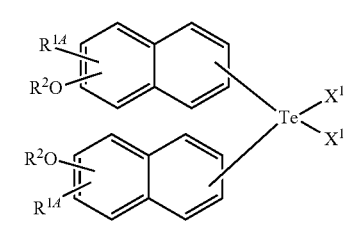

Formula (4A)

wherein $R^{14}$, $R^2$, and $X^1$ are as defined in the above formula (3A).

<10> The material for lithography according to <6>, wherein the tellurium-containing compound is represented by the following formula (2B):

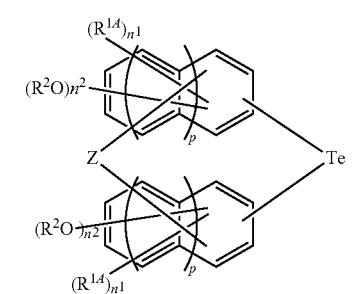

Formula (2B)

wherein Z, $R^{14}$, $R^2$, p, $n^1$, and $n^2$ are as defined in the above formula (1B).

<11> The material for lithography according to <10>, wherein the tellurium-containing compound is represented by the following formula (3B):

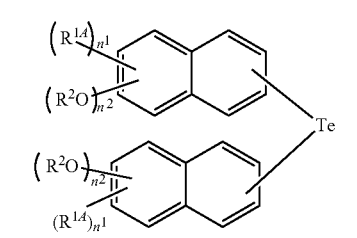

Formula (3B)

wherein $R^{1A}$, $R^2$, $n^1$, and $n^2$ are as defined in the above formula (2B).

<12> The material for lithography according to <11>, wherein the tellurium-containing compound is represented by the following formula (4B):

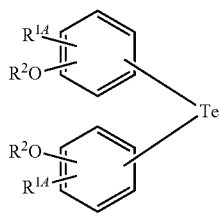

Formula (4B)

wherein $R^1$, $R^2$, and $X^1$ are as defined in the above formula (3B).

<13> The material for lithography according to any of <5> to <12>, wherein the tellurium-containing compound has at least one acid dissociation reactive group as the $R^2$.

<14> The material for lithography according to any of <5> to <12>, wherein all of the $R^2$ in the tellurium-containing compound are hydrogen atoms.

<15> The material for lithography according to <1>, wherein the tellurium-containing resin is a resin comprising a constitutional unit derived from a compound represented by the following formula (A-1):

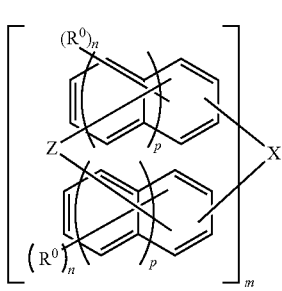

Formula (A-1)

wherein X is a 2m-valent group of 0 to 60 carbon atoms containing tellurium; Z is an oxygen atom, a sulfur atom, or non-crosslinked state; each $R^0$ is independently selected from the group consisting of a monovalent group containing an oxygen atom, a monovalent group containing a sulfur atom, a monovalent group containing a nitrogen atom, a hydrocarbon group, a halogen atom, and a combination thereof; m is an integer of 1 to 4; each p is independently an integer of 0 to 2; and each n is independently an integer of 0 to (5+2×p).

<16> The material for lithography according to <1>, wherein the tellurium-containing resin is a resin comprising a constitutional unit derived from a compound represented by the following formula (A-2):

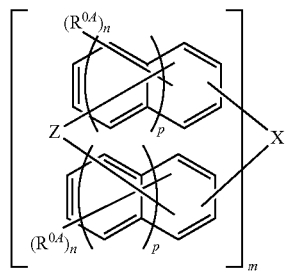

Formula (A-2)

wherein X is a 2m-valent group of 0 to 60 carbon atoms containing tellurium; Z is an oxygen atom, a sulfur atom, a single bond, or non-crosslinked state; each $R^{0A}$ is independently selected from the group consisting of a hydrocarbon group, a halogen atom, a cyano group, a nitro group, an amino group, an alkyl group of 1 to 30 carbon atoms, an alkenyl group of 2 to 30 carbon atoms, an aryl group of 6 to 40 carbon atoms, a hydroxy group or a group in which a hydrogen atom of a hydroxy group is substituted with an acid crosslinking reactive group or an acid dissociation reactive group, and a combination thereof, wherein the alkyl group, the alkenyl group, and the aryl group each optionally have an ether bond, a ketone bond, or an ester bond; m is an integer of 1 to 4; each p is independently an integer of 0 to 2; and each n is independently an integer of 0 to (5+2×p).

<17> The material for lithography according to any of <1> to <14>, wherein the tellurium-containing resin is a resin comprising a constitutional unit derived from a compound represented by the following formula (A-3):

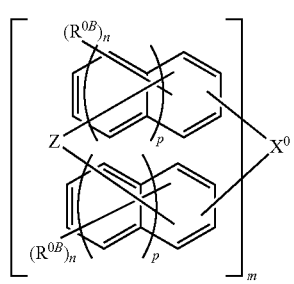

Formula (A-3)

wherein $X^0$ is a 2m-valent group of 0 to 30 carbon atoms containing tellurium; Z is an oxygen atom, a sulfur atom, or non-crosslinked state; each $R^{0B}$ is independently a monovalent group containing an oxygen atom, a monovalent group containing a sulfur atom, a monovalent group containing a nitrogen atom, a hydrocarbon group, or a halogen atom; m is an integer of 1 to 4; each p is independently an integer of 0 to 2; and each n is independently an integer of 0 to (5+2×p).

<18> The material for lithography according to <1>, wherein the tellurium-containing resin is a resin comprising a constitutional unit represented by the following formula (B1-M):

Formula (B1-M)

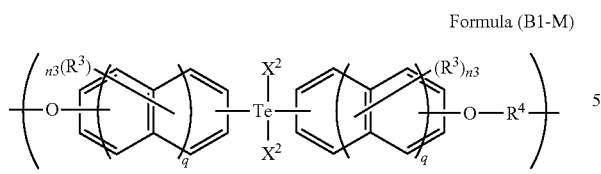

wherein each $X^2$ is independently a monovalent group containing an oxygen atom, a monovalent group containing a sulfur atom, a monovalent group containing a nitrogen atom, a hydrocarbon group, a hydrogen atom, or a halogen atom; each $R^3$ is independently a monovalent group containing an oxygen atom, a monovalent group containing a sulfur atom, a monovalent group containing a nitrogen atom, a hydrocarbon group, or a halogen atom; q is an integer of 0 to 2; $n^3$ is an integer of 0 to (4+2×q); and $R^4$ is a single bond or any structure represented by the following general formula (5):

General formula (5)

Formula (5')

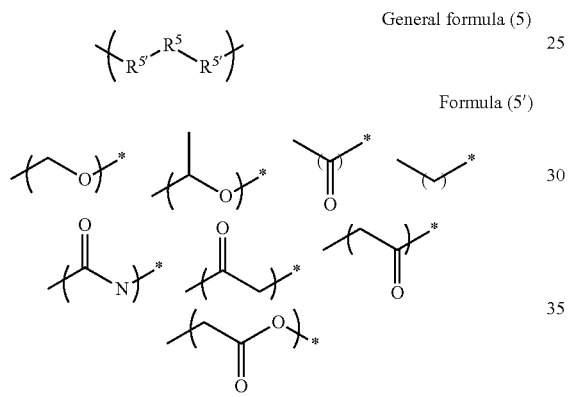

wherein $R^5$ is a substituted or unsubstituted linear alkylene group of 1 to 20 carbon atoms, branched alkylene group of 3 to 20 carbon atoms, or cyclic alkylene group of 3 to 20 carbon atoms, or a substituted or unsubstituted arylene group of 6 to 20 carbon atoms; and each $R^{5'}$ is independently any structure of the above formula (5') wherein * indicates that this portion is connected to $R^5$.

<19> The material for lithography according to <18>, wherein the $R^4$ in the tellurium-containing resin is any structure represented by the above general formula (5).

<20> The material for lithography according to <18>, wherein the tellurium-containing resin is a resin comprising a constitutional unit represented by the following formula (B2-M'):

Formula (B2-M')

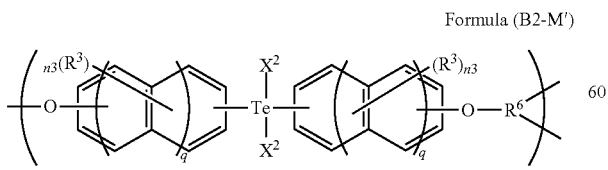

wherein $X^2$, $R^3$, q, and $n^3$ are as defined in the formula (B1-M); and $R^6$ is any structure represented by the following general formula (6):

General formula (6)

Formula (6')

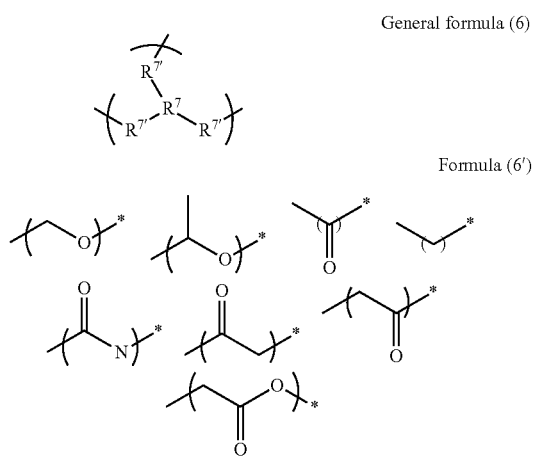

wherein $R^7$ is a substituted or unsubstituted linear alkylene group of 1 to 20 carbon atoms, branched alkylene group of 3 to 20 carbon atoms, or cyclic alkylene group of 3 to 20 carbon atoms, or a substituted or unsubstituted arylene group of 6 to 20 carbon atoms; each $R^{7'}$ is independently any structure of the above formula (6') wherein * indicates that this portion is connected to $R^7$.

<21> The material for lithography according to <1>, wherein the tellurium-containing resin is a resin comprising a constitutional unit represented by the following formula (C1):

Formula (C1)

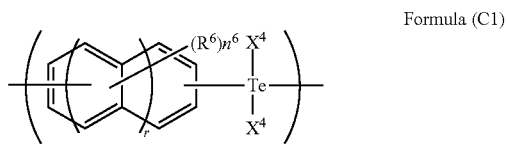

wherein each $X^4$ is independently a monovalent group containing an oxygen atom, a monovalent group containing a sulfur atom, a monovalent group containing a nitrogen atom, a hydrocarbon group, a hydrogen atom, or a halogen atom; each $R^6$ is independently a monovalent group containing an oxygen atom, a monovalent group containing a sulfur atom, a monovalent group containing a nitrogen atom, a hydrocarbon group, or a halogen atom; r is an integer of 0 to 2; and $n^6$ is an integer of 2 to (4+2×r).

<22> The material for lithography according to <1>, wherein the tellurium-containing resin is a resin comprising a constitutional unit represented by the following formula (B3-M):

Formula (B3-M)

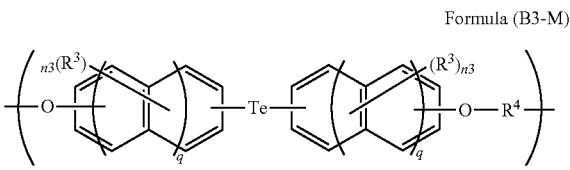

wherein each $R^3$ is independently a monovalent group containing an oxygen atom, a monovalent group containing a sulfur atom, a monovalent group containing a nitrogen atom, a hydrocarbon group, or a halogen atom; q is an integer of 0 to 2; $n^3$ is an integer of 0 to (4+2×q); and $R^4$ is a single bond or any structure represented by the following general formula (5):

General formula (5)

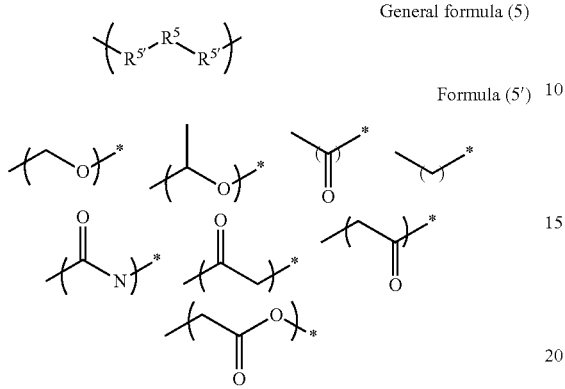

Formula (5')

wherein $R^5$ is a substituted or unsubstituted linear alkylene group of 1 to 20 carbon atoms, branched alkylene group of 3 to 20 carbon atoms, or cyclic alkylene group of 3 to 20 carbon atoms, or a substituted or unsubstituted arylene group of 6 to 20 carbon atoms; each $R^{5'}$ is independently any structure of the above formula (5') wherein * indicates that this portion is connected to $R^5$.

<23> The material for lithography according to <22>, wherein the $R^4$ in the tellurium-containing resin is any structure represented by the above general formula (5).

<24> The material for lithography according to <22>, wherein the tellurium-containing resin is a resin comprising a constitutional unit represented by the following formula (B4-M'):

Formula (B4-M')

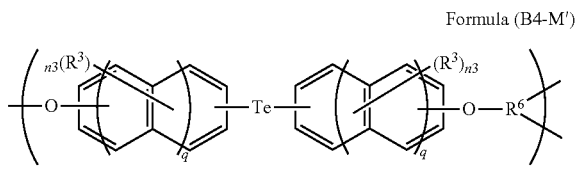

wherein $R^3$, q, and $n^3$ are as defined in the formula (B3-M); and $R^6$ is any structure represented by the following general formula (6):

General formula (6)

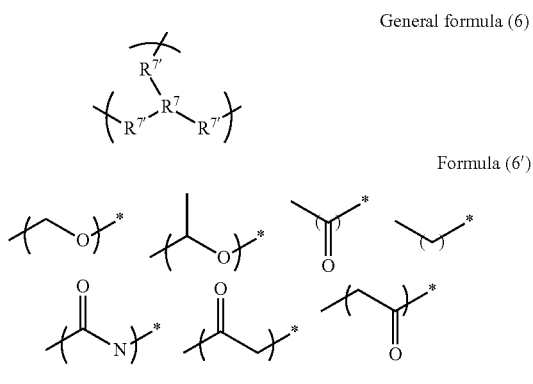

Formula (6')

-continued

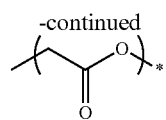

wherein $R^7$ is a substituted or unsubstituted linear alkylene group of 1 to 20 carbon atoms, branched alkylene group of 3 to 20 carbon atoms, or cyclic alkylene group of 3 to 20 carbon atoms, or a substituted or unsubstituted arylene group of 6 to 20 carbon atoms; and each $R^{7'}$ is independently any structure of the above formula (6') wherein * indicates that this portion is connected to $R^7$.

<25> The material for lithography according to <1>, wherein the tellurium-containing resin is a resin comprising a constitutional unit represented by the following formula (C2):

Formula (C2)

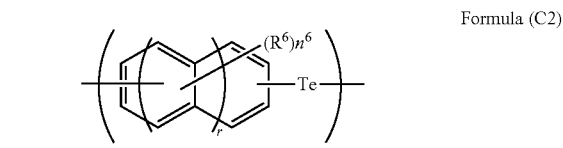

wherein each $R^6$ is independently a monovalent group containing an oxygen atom, a monovalent group containing a sulfur atom, a monovalent group containing a nitrogen atom, a hydrocarbon group, or a halogen atom; r is an integer of 0 to 2; and $n^6$ is an integer of 2 to (4+2×r).

<26> A method for producing the material for lithography according to any of <1> to <25>, comprising the step of reacting tellurium tetrachloride with a substituted or unsubstituted phenol derivative in the presence of a basic catalyst to synthesize the tellurium-containing compound.

<27> A material composition for lithography comprising the material for lithography according to any of <1> to <25> and a solvent.

<28> The material composition for lithography according to <27>, further comprising an acid generating agent.

<29> The material composition for lithography according to <27> or <28>, further comprising an acid crosslinking agent.

<30> The material composition for lithography according to any of <27> to <29>, further comprising an optically active diazonaphthoquinone compound.

<31> The material for lithography according to any of <1> to <25> for use in a resist composition.

<32> A method for forming a pattern, comprising:
a film formation step of forming a film on a substrate using the material for lithography according to any of <1> to <25> and <31> or the material composition for lithography according to any of <27> to <30>;
an exposure step of exposing the film; and
a development step of developing the film exposed in the exposure step, thereby forming a pattern.

<33> A compound represented by the following formula (A-1):

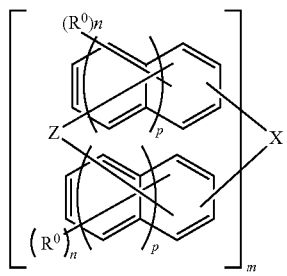

Formula (A-1)

wherein X is a 2m-valent group of 0 to 60 carbon atoms containing tellurium; Z is an oxygen atom, a sulfur atom, or non-crosslinked state; each $R^0$ is independently selected from the group consisting of a monovalent group containing an oxygen atom, a monovalent group containing a sulfur atom, a monovalent group containing a nitrogen atom, a hydrocarbon group, a halogen atom, and a combination thereof; m is an integer of 1 to 4; each p is independently an integer of 0 to 2; and each n is independently an integer of 0 to (5+2×p).

<34> A compound represented by the following formula (A-2):

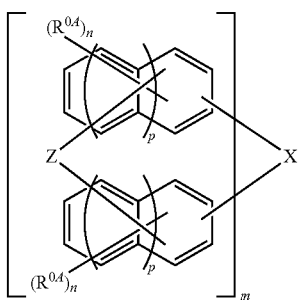

Formula (A-2)

wherein X is a 2m-valent group of 0 to 60 carbon atoms containing tellurium; Z is an oxygen atom, a sulfur atom, a single bond, or non-crosslinked state; each $R^{0A}$ is independently selected from the group consisting of a hydrocarbon group, a halogen atom, a cyano group, a nitro group, an amino group, an alkyl group of 1 to 30 carbon atoms, an alkenyl group of 2 to 30 carbon atoms, an aryl group of 6 to 40 carbon atoms, a hydroxy group or a group in which a hydrogen atom of a hydroxy group is substituted with an acid crosslinking reactive group or an acid dissociation reactive group, and a combination thereof, wherein the alkyl group, the alkenyl group, and the aryl group each optionally have an ether bond, a ketone bond, or an ester bond; m is an integer of 1 to 4; each p is independently an integer of 0 to 2; each n is independently an integer of 0 to (5+2×p).

<35> A compound represented by the following formula (1A'):

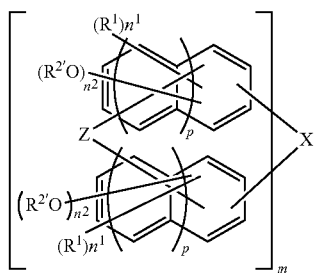

Formula (1A')

wherein X is a 2m-valent group of 0 to 60 carbon atoms containing tellurium; Z is an oxygen atom, a sulfur atom, or non-crosslinked state; each $R^1$ is independently selected from the group consisting of a hydrocarbon group, a halogen atom, a cyano group, a nitro group, an amino group, an alkyl group of 1 to 30 carbon atoms, an alkenyl group of 2 to 30 carbon atoms, an aryl group of 6 to 40 carbon atoms, and a combination thereof, wherein the alkyl group, the alkenyl group, and the aryl group each optionally have an ether bond, a ketone bond, or an ester bond; each $R^{2'}$ is independently a hydrogen atom, an acid crosslinking reactive group, or an acid dissociation reactive group, and at least one $R^{2'}$ is an acid dissociation reactive group; m is an integer of 1 to 4; each p is independently an integer of 0 to 2; each $n^1$ is independently an integer of 0 to (5+2×p); and each $n^2$ is independently an integer of 0 to (5+2×p), provided that at least one $n^2$ is an integer of 1 to (5+2×p).

<36> A compound represented by the following formula (1B'):

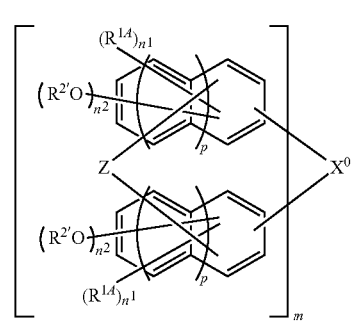

Formula (1B')

wherein $X^0$ is a 2m-valent group of 0 to 30 carbon atoms containing tellurium; Z is an oxygen atom, a sulfur atom, or non-crosslinked state; each $R^{1A}$ is independently an alkyl group, an aryl group, an alkenyl group, or a halogen atom; each $R^{2'}$ is independently a hydrogen atom or an acid dissociation reactive group, and at least one $R^{2'}$ is an acid dissociation reactive group; m is an integer of 1 to 4; each p is independently an integer of 0 to 2; each $n^1$ is independently an integer of 0 to (5+2×p); and each $n^2$ is independently an integer of 0 to (5+2×p), provided that at least one $n^2$ is an integer of 1 to (5+2×p).

<37> A resin comprising a constitutional unit derived from a compound represented by the formula (A-1):

Formula (A-1)

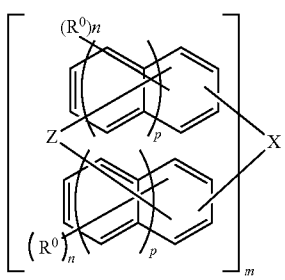

wherein X is a 2m-valent group of 0 to 60 carbon atoms containing tellurium; Z is an oxygen atom, a sulfur atom, or non-crosslinked state; each $R^0$ is independently selected from the group consisting of a monovalent group containing an oxygen atom, a monovalent group containing a sulfur atom, a monovalent group containing a nitrogen atom, a hydrocarbon group, a halogen atom, and a combination thereof; m is an integer of 1 to 4; each p is independently an integer of 0 to 2; and each n is independently an integer of 0 to $(5+2\times p)$.

<38> The resin according to <37> obtained by reacting the compound represented by the above formula (A-1) with a crosslinking compound.

<39> The resin according to <38>, wherein the crosslinking compound is an aldehyde, a ketone, a carboxylic acid, a carboxylic acid halide, a halogen-containing compound, an amino compound, an imino compound, an isocyanate, or an unsaturated hydrocarbon group-containing compound.

<40> A resin comprising a constitutional unit represented by the following formula (B1-M'):

Formula (B1-M')

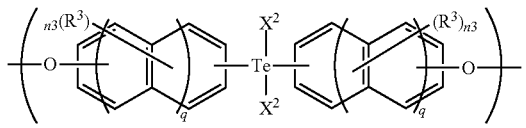

wherein each $X^2$ is independently a monovalent group containing an oxygen atom, a monovalent group containing a sulfur atom, a monovalent group containing a nitrogen atom, a hydrocarbon group, a hydrogen atom, or a halogen atom; each $R^3$ is independently a monovalent group containing an oxygen atom, a monovalent group containing a sulfur atom, a monovalent group containing a nitrogen atom, a hydrocarbon group, or a halogen atom; q is an integer of 0 to 2; and $n^3$ is an integer of 0 to $(4+2\times q)$.

<41> A resin comprising a constitutional unit represented by the following formula (B2-M):

Formula (B2-M)

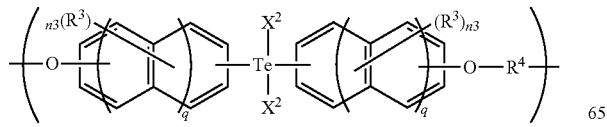

wherein each $X^2$ is independently a monovalent group containing an oxygen atom, a monovalent group containing a sulfur atom, a monovalent group containing a nitrogen atom, a hydrocarbon group, a hydrogen atom, or a halogen atom; each $R^3$ is independently a monovalent group containing an oxygen atom, a monovalent group containing a sulfur atom, a monovalent group containing a nitrogen atom, a hydrocarbon group, or a halogen atom; q is an integer of 0 to 2; $n^3$ is an integer of 0 to $(4+2\times q)$; and $R^4$ is any structure represented by the following general formula (5):

General formula (5)

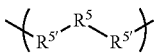

Formula (5')

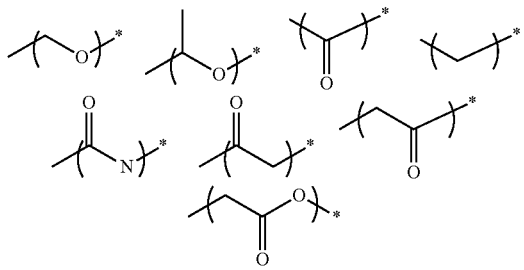

wherein $R^5$ is a substituted or unsubstituted linear alkylene group of 1 to 20 carbon atoms, branched alkylene group of 3 to 20 carbon atoms, or cyclic alkylene group of 3 to 20 carbon atoms, or a substituted or unsubstituted arylene group of 6 to 20 carbon atoms; each $R^{5'}$ is independently any structure of the above formula (5') wherein * indicates that this portion is connected to $R^5$.

<42> A resin comprising a constitutional unit represented by the following formula (B2-M'):

Formula (B2-M')

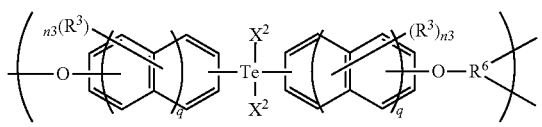

wherein each $X^2$ is independently a monovalent group containing an oxygen atom, a monovalent group containing a sulfur atom, a monovalent group containing a nitrogen atom, a hydrocarbon group, a hydrogen atom, or a halogen atom; each $R^3$ is independently a monovalent group containing an oxygen atom, a monovalent group containing a sulfur atom, a monovalent group containing a nitrogen atom, a hydrocarbon group, or a halogen atom; q is an integer of 0 to 2; $n^3$ is an integer of 0 to $(4+2\times q)$; and $R^6$ is any structure represented by the following general formula (6):

General formula (6)

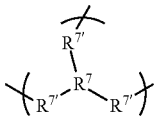

Formula (6')

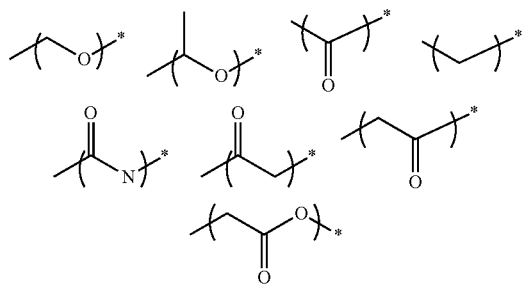

wherein $R^7$ is a substituted or unsubstituted linear alkylene group of 1 to 20 carbon atoms, branched alkylene group of 3 to 20 carbon atoms, or cyclic alkylene group of 3 to 20 carbon atoms, or a substituted or unsubstituted arylene group of 6 to 20 carbon atoms; each $R^{7'}$ is independently any structure of the above formula (6') wherein * indicates that this portion is connected to $R^7$.

<43> A resin comprising a constitutional unit represented by the following formula (C1):

Formula (C1)

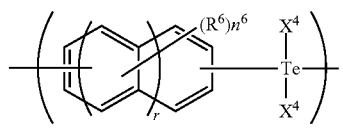

wherein each $X^4$ is independently a monovalent group containing an oxygen atom, a monovalent group containing a sulfur atom, a monovalent group containing a nitrogen atom, a hydrocarbon group, a hydrogen atom, or a halogen atom; each $R^6$ is independently a monovalent group containing an oxygen atom, a monovalent group containing a sulfur atom, a monovalent group containing a nitrogen atom, a hydrocarbon group, or a halogen atom; r is an integer of 0 to 2; and $n^6$ is an integer of 2 to $(4+2\times r)$.

<44> A resin comprising a constitutional unit represented by the following formula (B3-M'):

Formula (B3-M')

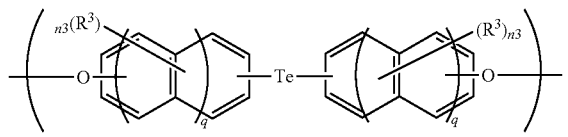

wherein each $R^3$ is independently a monovalent group containing an oxygen atom, a monovalent group containing a sulfur atom, a monovalent group containing a nitrogen atom, a hydrocarbon group, or a halogen atom; q is an integer of 0 to 2; and $n^3$ is an integer of 0 to $(4+2\times q)$.

<45> A resin comprising a constitutional unit represented by the following formula (B4-M):

Formula (B4-M)

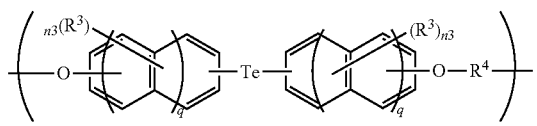

wherein $R^3$, q, and $n^3$ are as defined in the formula (B3-M); and $R^4$ is any structure represented by the following general formula (5):

General formula (5)

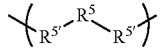

Formula (5')

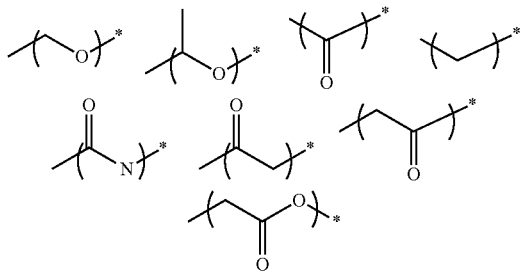

wherein $R^5$ is a substituted or unsubstituted linear alkylene group of 1 to 20 carbon atoms, branched alkylene group of 3 to 20 carbon atoms, or cyclic alkylene group of 3 to 20 carbon atoms, or a substituted or unsubstituted arylene group of 6 to 20 carbon atoms; each $R^{5'}$ is independently any structure of the above formula (5') wherein * indicates that this portion is connected to $R^5$.

<46> A resin comprising a constitutional unit represented by the following formula (B4-M'):

Formula (B4-M')

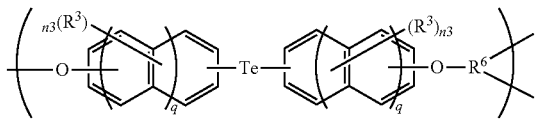

wherein each $R^3$ is independently a monovalent group containing an oxygen atom, a monovalent group containing a sulfur atom, a monovalent group containing a nitrogen atom, a hydrocarbon group, or a halogen atom; q is an integer of 0 to 2; $n^3$ is an integer of 0 to $(4+2\times q)$; and $R^6$ is any structure represented by the following general formula (6):

General formula (6)

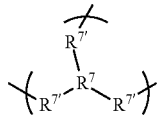

-continued

Formula (6')

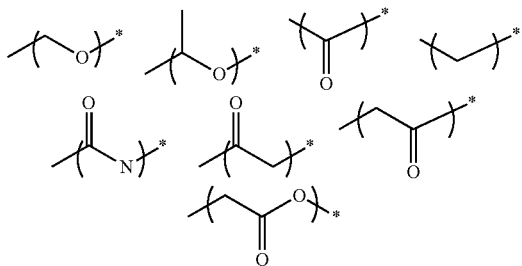

wherein $R^7$ is a substituted or unsubstituted linear alkylene group of 1 to 20 carbon atoms, branched alkylene group of 3 to 20 carbon atoms, or cyclic alkylene group of 3 to 20 carbon atoms, or a substituted or unsubstituted arylene group of 6 to 20 carbon atoms; each $R^{7'}$ is independently any structure of the above formula (6') wherein * indicates that this portion is connected to $R^7$.

<47> A resin comprising a constitutional unit represented by the following formula (C2):

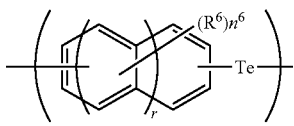

Formula (C2)

wherein each $R^6$ is independently a monovalent group containing an oxygen atom, a monovalent group containing a sulfur atom, a monovalent group containing a nitrogen atom, a hydrocarbon group, or a halogen atom; r is an integer of 0 to 2; and $n^6$ is an integer of 2 to $(4+2 \times r)$.

<48> A purification method comprising:
obtaining a solution (A) by dissolving a compound represented by the following formula (A-1) or the resin according to any of <37> to <47> in a solvent comprising an organic solvent that does not inadvertently mix with water; and
a first extraction step that extracts impurities in the compound or the resin by bringing the obtained solution (A) into contact with an acidic aqueous solution:

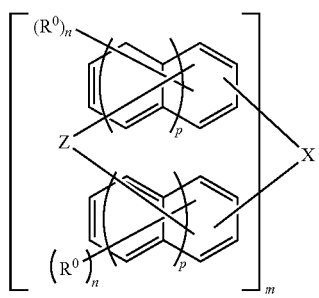

Formula (A-1)

wherein X is a 2m-valent group of 0 to 60 carbon atoms containing tellurium; Z is an oxygen atom, a sulfur atom, or non-crosslinked state; each $R^0$ is independently selected from the group consisting of a monovalent group containing an oxygen atom, a monovalent group containing a sulfur atom, a monovalent group containing a nitrogen atom, a hydrocarbon group, a halogen atom, and a combination thereof; m is an integer of 1 to 4; each p is independently an integer of 0 to 2; and each n is independently an integer of 0 to $(5+2 \times p)$.

<49> The purification method according to <48>, wherein the acidic aqueous solution is one or more aqueous mineral acid solutions selected from the group consisting of hydrochloric acid, sulfuric acid, nitric acid, and phosphoric acid; or one or more aqueous organic acid solutions selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid.

<50> The purification method according to <48> or <49>, wherein the organic solvent that does not inadvertently mix with water is one or more organic solvents selected from the group consisting of toluene, 2-heptanone, cyclohexanone, cyclopentanone, methyl isobutyl ketone, propylene glycol monomethyl ether acetate, and ethyl acetate.

<51> The purification method according to any of <48> to <50>, comprising a second extraction step that extracts impurities in the compound or the resin by further bringing a solution phase comprising the compound or the resin into contact with water after the first extraction step.

The present invention can provide a material for lithography which can be used in a resist composition, etc. which is capable of reducing film defects (thin film formability), has good storage stability and high sensitivity, and can impart a good shape to a resist pattern, a production method therefor, and a material composition for lithography and a pattern formation method using the material for lithography.

Also, the present invention can provide a compound and a resin (for example, a tellurium-containing polyphenol derivative) which have high sensitivity and high solubility in a safe solvent, and a method for purifying the compound or the resin.

DESCRIPTION OF EMBODIMENTS

Hereinafter, an embodiment of the present invention will be described (hereinafter, also referred to as "present embodiment"). The present embodiment is given in order to illustrate the present invention. The present invention is not limited to only the present embodiment.

The material for lithography of the present invention is a material that can be used in lithography technology, and is not particularly limited. The material for lithography of the present invention can be used as, for example, a material composition for lithography together with a solvent and the like and can be further used for the purpose of, for example, preparing a resist (i.e., a resist composition), forming an intermediate layer (i.e., a composition for intermediate layer formation), and forming an underlayer film (i.e., a composition for underlayer film formation).

[Material for Lithography]

The material for lithography of the present embodiment is a material for lithography comprising a tellurium-containing compound or resin. By containing the tellurium-containing compound or resin, the material for lithography of the present embodiment can be expected to produce a sensitizing effect, particularly, in lithography with EUV. Tellurium has the second highest sensitizing effect following xenon, among all elements.

From the viewpoint of storage stability, it is preferable that the material for lithography of the present embodiment is not a metallic tellurium, a tellurium oxide, or an ionic tellurium compound or resin.

The material for lithography contains one or more selected from, for example, a compound represented by the formula (A-1) mentioned later and a resin obtained using this compound as a monomer (i.e., comprising a constitutional unit derived from the compound represented by the formula (A-1)).

(Tellurium-Containing Compound Represented by Formula (A-1))

According to the first embodiment, the material for lithography of the present embodiment can contain a tellurium-containing compound represented by the following formula (A-1):

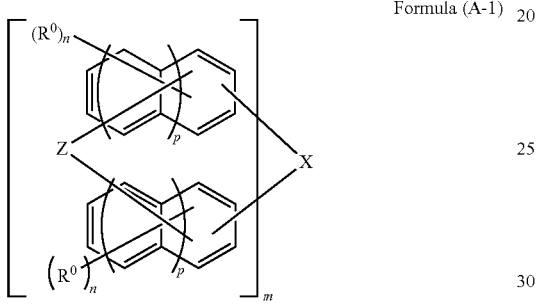

Formula (A-1)

(In the formula (A-1), X is a 2m-valent group of 0 to 60 carbon atoms containing tellurium; Z is an oxygen atom, a sulfur atom, or non-crosslinked state; each $R^0$ is independently selected from the group consisting of a monovalent group containing an oxygen atom, a monovalent group containing a sulfur atom, a monovalent group containing a nitrogen atom, a hydrocarbon group, a halogen atom, and a combination thereof; m is an integer of 1 to 4; each p is independently an integer of 0 to 2; and each n is independently an integer of 0 to (5+2×p).)

The chemical structure of the compound contained in the material for lithography of the present embodiment can be determined by 1H-NMR analysis.

The compound contained in the material for lithography of the present embodiment contains tellurium as shown in the above formula (A-1) and can therefore be expected to produce a sensitizing effect, particularly, in lithography with EUV. Also, the compound has a benzene skeleton or a naphthalene skeleton or the like and is therefore excellent in heat resistance.

In the above formula (A-1), m is an integer of 1 to 4. When m is an integer of 2 or larger, the structural formulae of m repeat units may be the same or different. In the above formula (A-1), m is preferably 1 to 3 from the viewpoint of resist properties such as heat resistance, resolution, and roughness.

Although the compound of the present embodiment is not a polymer, the structure indicated within the parentheses [ ] bonded to X in the above formula (A-1) is referred to as "structural formula of a repeat unit (the same holds true for formulae given below) for the sake of convenience.

In the above formula (A-1), each p is independently an integer of 0 to 2 and is a value that determines the structure of the accompanying ring structure (a ring structure represented by naphthalene in the formula (A-1) (hereinafter, the ring structure is also simply referred to as "ring structure A")). Specifically, as shown below, in the formula (A-1), the ring structure A refers to a benzene structure (p=0), a naphthalene structure (p=1), or a tricyclic structure such as anthracene or phenanthrene (p=2). The ring structure A is not particularly limited, but is preferably a benzene structure or a naphthalene structure from the viewpoint of solubility. In the formula (A-1), X, Z, and $R^0$ are bonded to any possible site on the ring structure A.

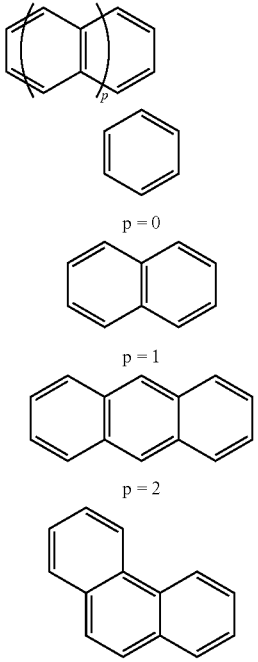

Ring structure A

In the above formula (A-1), X is a 2m-valent group of 0 to 60 carbon atoms containing tellurium. X is a single bond containing tellurium or a 2m-valent hydrocarbon group of 0 to 60 carbon atoms containing tellurium.

The 2m-valent group refers to an alkylene group of 1 to 60 carbon atoms (m=1), an alkanetetrayl group of 1 to 60 carbon atoms (m=2), an alkanehexayl group of 2 to 60 carbon atoms (m=3), or an alkaneoctayl group of 3 to 60 carbon atoms (m=4). Examples of the 2m-valent group include groups having a linear, branched, or cyclic structure.

Also, the 2m-valent hydrocarbon group may have an alicyclic hydrocarbon group, a double bond, a hetero atom, or an aromatic group of 6 to 60 carbon atoms. Herein, the alicyclic hydrocarbon group also includes bridged alicyclic hydrocarbon groups.

X preferably has a condensed polycyclic aromatic group (particularly, a bicyclic to tetracyclic condensed ring structure) from the viewpoint of heat resistance and preferably has a polyphenyl group such as a biphenyl group from the viewpoint of solubility in a safe solvent and heat resistance.

Specific examples of the 2m-valent group of 0 to 60 carbon atoms containing tellurium, represented by X include the following groups:

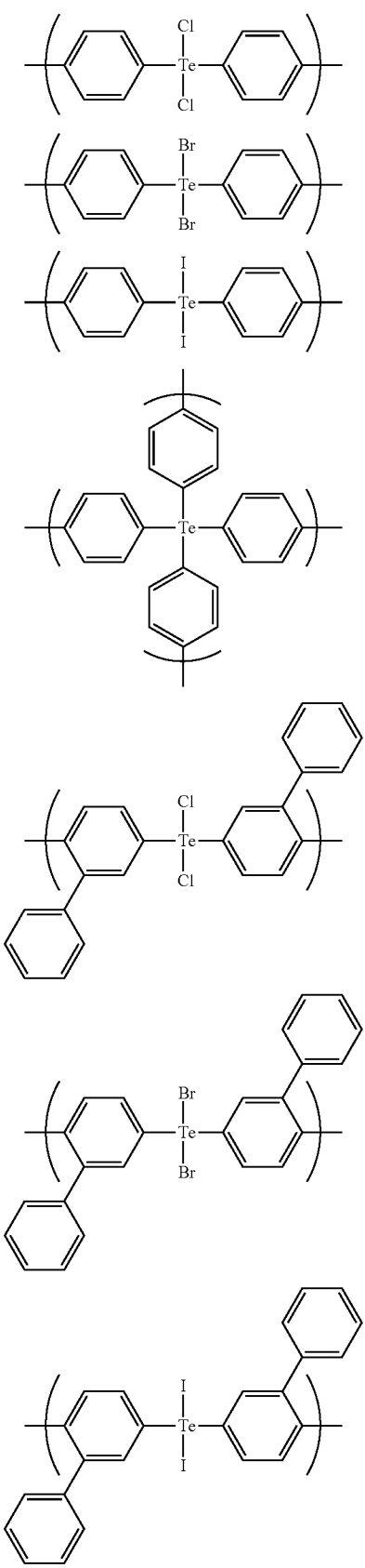

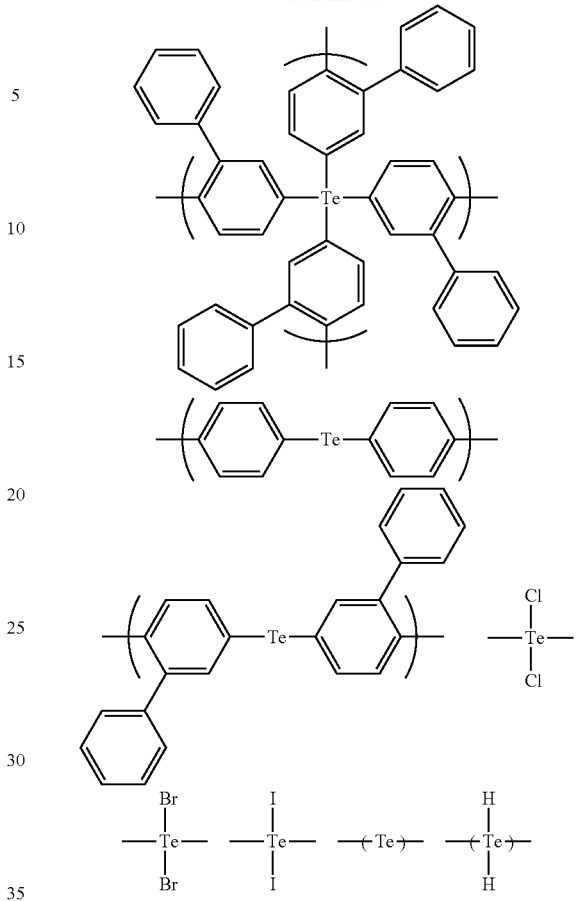

In the above formula (A-1), Z is an oxygen atom, a sulfur atom, or non-crosslinked state. When m is 2 or larger, Z may be the same or different. Also, when m is 2 or larger, the structural formulae of different repeat units may be bonded via Z. For example, when m is 2 or larger, the structural formulae of different repeat units may be bonded via Z and the structural formulae of a plurality of repeat units may constitute a cup like structure or the like. Z is not particularly limited, but is preferably an oxygen atom or a sulfur atom from the viewpoint of heat resistance.

In the above formula (A-1), $R^0$ is a monovalent group containing an oxygen atom, a monovalent group containing a sulfur atom, a monovalent group containing a nitrogen atom, a halogen atom, or a combination thereof.

Herein, examples of the monovalent group containing an oxygen atom include, but not limited to, acyl groups of 1 to 20 carbon atoms, alkoxycarbonyl groups of 2 to 20 carbon atoms, linear alkyloxy groups of 1 to 6 carbon atoms, branched alkyloxy groups of 3 to 20 carbon atoms, cyclic alkyloxy groups of 3 to 20 carbon atoms, linear alkenyloxy groups of 2 to 6 carbon atoms, branched alkenyloxy groups of 3 to 6 carbon atoms, cyclic alkenyloxy groups of 3 to 10 carbon atoms, aryloxy groups of 6 to 10 carbon atoms, acyloxy groups of 1 to 20 carbon atoms, alkoxycarbonyloxy groups of 2 to 20 carbon atoms, alkoxycarbonylalkyl groups of 2 to 20 carbon atoms, 1-substituted alkoxymethyl groups of 2 to 20 carbon atoms, cyclic ether oxy groups of 2 to 20 carbon atoms, alkoxyalkyloxy groups of 2 to 20 carbon atoms, a glycidyloxy group, allyloxy groups, (meth)acryl groups, a glycidyl acrylate group, a glycidyl methacrylate group, and a hydroxy group.

Examples of the acyl groups of 1 to 20 carbon atoms include, but not limited to, a methanoyl group (a formyl group), an ethanoyl group (an acetyl group), a propanoyl group, a butanoyl group, a pentanoyl group, a hexanoyl group, an octanoyl group, a decanoyl group, and a benzoyl group.

Examples of the alkoxycarbonyl groups of 2 to 20 carbon atoms include, but not limited to, a methoxycarbonyl group, an ethoxycarbonyl group, a propoxycarbonyl group, a butoxycarbonyl group, a pentyloxycarbonyl group, a hexyloxycarbonyl group, an octyloxycarbonyl group, and a decyloxycarbonyl group.

Examples of the linear alkyloxy groups of 1 to 6 carbon atoms include, but not limited to, a methoxy group, an ethoxy group, a n-propoxy group, a n-butoxy group, a n-pentyloxy group, and a n-hexyloxy group.

Examples of the branched alkyloxy groups of 3 to 20 carbon atoms include, but not limited to, an isopropoxy group, an isobutoxy group, and a tert-butoxy group.

Examples of the cyclic alkyloxy groups of 3 to 20 carbon atoms include, but not limited to, a cyclopropoxy group, a cyclobutoxy group, a cyclopentyloxy group, a cyclohexyloxy group, a cyclooctyloxy group, and a cyclodecyloxy group.

Examples of the linear alkenyloxy groups of 2 to 6 carbon atoms include, but not limited to, a vinyloxy group, a 1-propenyloxy group, a 2-propenyloxy group, a 1-butenyloxy group, and a 2-butenyloxy group.

Examples of the branched alkenyloxy groups of 3 to 6 carbon atoms include, but not limited to, an isopropenyloxy group, an isobutenyloxy group, an isopentenyloxy group, and an isohexenyloxy group.

Examples of the cyclic alkenyloxy groups of 3 to 10 carbon atoms include, but not limited to, a cyclopropenyloxy group, a cyclobutenyloxy group, a cyclopentenyloxy group, a cyclohexenyloxy group, a cyclooctenyloxy group, and a cyclodecynyloxy group.

Examples of the aryloxy groups of 6 to 10 carbon atoms include, but not limited to, a phenyloxy group (a phenoxy group), a 1-naphthyloxy group, and a 2-naphthyloxy group.

Examples of the acyloxy groups of 1 to 20 carbon atoms include, but not limited to, a formyloxy group, an acetyloxy group, a propionyloxy group, a butyryloxy group, an isobutyryloxy group, and a benzoyloxy group.

Examples of the alkoxycarbonyloxy groups of 2 to 20 carbon atoms include, but not limited to, a methoxycarbonyloxy group, an ethoxycarbonyloxy group, a propoxycarbonyloxy group, a butoxycarbonyloxy group, an octyloxycarbonyloxy group, and a decyloxycarbonyloxy group.

Examples of the alkoxycarbonylalkyl groups of 2 to 20 carbon atoms include, but not limited to, a methoxycarbonylmethyl group, an ethoxycarbonylmethyl group, a n-propoxycarbonylmethyl group, an isopropoxycarbonylmethyl group, and a n-butoxycarbonylmethyl group.

Examples of the 1-substituted alkoxymethyl groups of 2 to 20 carbon atoms include, but not limited to, a 1-cyclopentylmethoxymethyl group, a 1-cyclopentylethoxymethyl group, a 1-cyclohexylmethoxymethyl group, a 1-cyclohexylethoxymethyl group, a 1-cyclooctylmethoxymethyl group, and a 1-adamantylmethoxymethyl group.

Examples of the cyclic ether oxy groups of 2 to 20 carbon atoms include, but not limited to, a tetrahydropyranyloxy group, a tetrahydrofuranyloxy group, a tetrahydrothiopyranyloxy group, a tetrahydrothiofuranyloxy group, a 4-methoxytetrahydropyranyloxy group, and a 4-methoxytetrahydrothiopyranyloxy group.

Examples of the alkoxyalkyloxy groups of 2 to 20 carbon atoms include, but not limited to, a methoxymethoxy group, an ethoxyethoxy group, a cyclohexyloxymethoxy group, a cyclohexyloxyethoxy group, a phenoxymethoxy group, and a phenoxyethoxy group.

Examples of the (meth)acryl groups include, but not limited to, an acryloyloxy group and a methacryloyloxy group. The glycidyl acrylate group is not particularly limited as long as it can be obtained by reacting a glycidyloxy group with acrylic acid. The glycidyl methacrylate group is not particularly limited as long as it can be obtained by reacting a glycidyloxy group with methacrylic acid.

Examples of the monovalent group containing a sulfur atom include, but not limited to, a thiol group. The monovalent group containing a sulfur atom is preferably a group in which a sulfur atom is directly bonded to a carbon atom constituting the ring structure (A) in the formula (A-1).

Examples of the monovalent group containing a nitrogen atom include, but not limited to, a nitro group, an amino group, and a diazo group. The monovalent group containing a nitrogen atom is preferably a group in which a nitrogen atom is directly bonded to a carbon atom constituting the ring structure (A-1) in the formula (A-1).

Examples of the hydrocarbon group include, but not limited to, linear alkyl groups of 1 to 6 carbon atoms, branched alkyl groups of 3 to 6 carbon atoms, cyclic alkyl groups of 3 to 10 carbon atoms, linear alkenyl groups of 2 to 6 carbon atoms, branched alkenyl groups of 3 to 6 carbon atoms, cyclic alkenyl groups of 3 to 10 carbon atoms, and aryl groups of 6 to 10 carbon atoms.

Examples of the linear alkyl groups of 1 to 6 carbon atoms include, but not limited to, a methyl group, an ethyl group, a n-propyl group, a n-butyl group, a n-pentyl group, and a n-hexyl group.

Examples of the branched alkyl groups of 3 to 6 carbon atoms include, but not limited to, an isopropyl group, an isobutyl group, a tert-butyl group, a neopentyl group, and a 2-hexyl group.

Examples of the cyclic alkyl groups of 3 to 10 carbon atoms include, but not limited to, a cyclopropyl group, a cyclobutyl group, a cyclopentyl group, a cyclohexyl group, a cyclooctyl group, and a cyclodecyl group.

Examples of the linear alkenyl groups of 2 to 6 carbon atoms include, but not limited to, a vinyl group, a 1-propenyl group, a 2-propenyl group (an allyl group), a 1-butenyl group, a 2-butenyl group, a 2-pentenyl group, and a 2-hexenyl group.

Examples of the branched alkenyl groups of 3 to 6 carbon atoms include, but not limited to, an isopropenyl group, an isobutenyl group, an isopentenyl group, and an isohexenyl group.

Examples of the cyclic alkenyl groups of 3 to 10 carbon atoms include, but not limited to, a cyclopropenyl group, a cyclobutenyl group, a cyclopentenyl group, a cyclohexenyl group, a cyclohexenyl group, a cyclooctenyl group, and a cyclodecynyl group.

Examples of the aryl groups of 6 to 10 carbon atoms include, but not limited to, a phenyl group and a naphthyl group.

Examples of the halogen atom include, but not limited to, a fluorine atom, a chlorine atom, a bromine atom, and an iodine atom.

In the above formula (A-1), each n is independently an integer of 0 to $(5+2\times p)$. In the present embodiment, at least one n in the above formula (A-1) is preferably an integer of 1 to 4 from the viewpoint of solubility in a solvent.

In the present embodiment, at least one $R^O$ in the above formula (A-1) is preferably a monovalent group containing an oxygen atom from the viewpoint of solubility in a solvent and the introduction of crosslinkability.

The tellurium-containing compound represented by the above formula (A-1) is preferably a tellurium-containing compound represented by the following formula (A-2) from the viewpoint of curability:

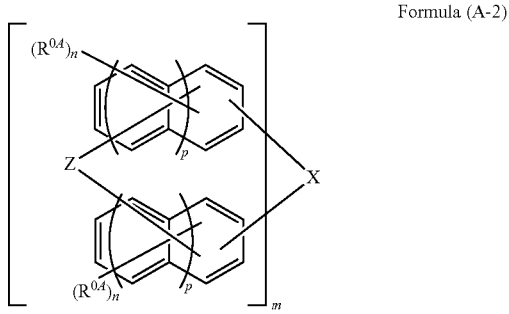

Formula (A-2)

(In the formula (A-2), X is a 2m-valent group of 0 to 60 carbon atoms containing tellurium; Z is an oxygen atom, a sulfur atom, a single bond, or non-crosslinked state; each $R^{OA}$ is independently selected from the group consisting of a hydrocarbon group, a halogen atom, a cyano group, a nitro group, an amino group, an alkyl group of 1 to 30 carbon atoms, an alkenyl group of 2 to 30 carbon atoms, an aryl group of 6 to 40 carbon atoms, a hydroxy group or a group in which a hydrogen atom of a hydroxy group is substituted with an acid crosslinking reactive group or an acid dissociation reactive group, and a combination thereof, wherein the alkyl group, the alkenyl group, and the aryl group each optionally have an ether bond, a ketone bond, or an ester bond; m is an integer of 1 to 4; each p is independently an integer of 0 to 2; and each n is independently an integer of 0 to (5+2×p).)

The "acid crosslinking reactive group" and the "acid dissociation reactive group" in $R^{OA}$ will be mentioned later.

The tellurium-containing compound represented by the above formula (A-1) is preferably a tellurium-containing compound represented by the following formula (A-3) from the viewpoint of solubility in a safe solvent:

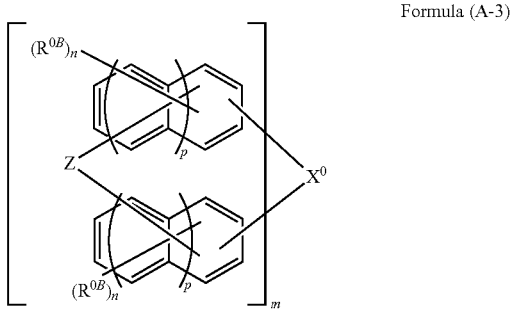

Formula (A-3)

(In the formula (A-3), $X^O$ is a 2m-valent group of 0 to 30 carbon atoms containing tellurium; Z is an oxygen atom, a sulfur atom, or non-crosslinked state; each $R^{OB}$ is independently a monovalent group containing an oxygen atom, a monovalent group containing a sulfur atom, a monovalent group containing a nitrogen atom, a hydrocarbon group, or a halogen atom; m is an integer of 1 to 4; each p is independently an integer of 0 to 2; and each n is independently an integer of 0 to (5+2×p).)

In the present embodiment, the tellurium-containing compound represented by the above formula (A-1) is preferably a compound other than BMPT, BHPT, and TDP mentioned later from the viewpoint of the pattern shape of the resulting resist.

—Tellurium-Containing Compound Represented by Formula (1A)—

The tellurium-containing compound represented by the above formula (A-1) is preferably a tellurium-containing compound represented by the following formula (1A):

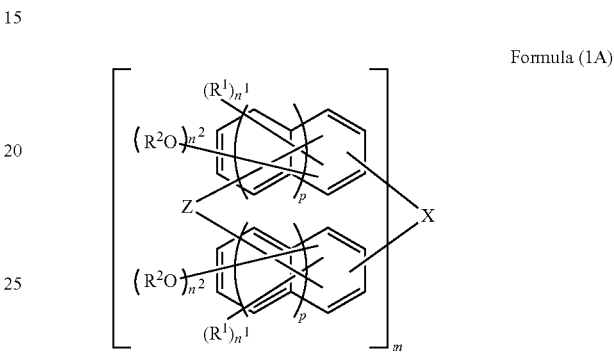

Formula (1A)

(In the formula (1A), X, Z, m, and p are as defined in the above formula (A-1); each $R^1$ is independently selected from the group consisting of a hydrocarbon group, a halogen atom, a cyano group, a nitro group, an amino group, an alkyl group of 1 to 30 carbon atoms, an alkenyl group of 2 to 30 carbon atoms, an aryl group of 6 to 40 carbon atoms, and a combination thereof, wherein the alkyl group, the alkenyl group, and the aryl group each optionally have an ether bond, a ketone bond, or an ester bond; each $R^2$ is independently a hydrogen atom, an acid crosslinking reactive group, or an acid dissociation reactive group; each $n^1$ is independently an integer of 0 to (5+2×p); and each $n^2$ is independently an integer of 0 to (5+2×p), provided that at least one $n^2$ is an integer of 1 to (5+2×p).)

In the formula (1A), each $n^1$ is independently an integer of 0 to (5+2×p), and each $n^2$ is independently an integer of 0 to (5+2×p). At least one $n^2$ is an integer of 1 to (5+2×p). Specifically, the tellurium-containing compound of the general formula (1A) has at least one "—$OR^2$" per ring structure A. In the formula (1), X, Z, $R^1$, and —$OR^2$ are bonded to any possible site on the ring structure A. Therefore, the upper limit of $n^1+n^2$ in one ring structure A corresponds to the upper limit of the number of possible bonding sites on the ring structure A also taking X and Z and the bonding sites into consideration.

Each $R^1$ is independently selected from the group consisting of a hydrocarbon group, a halogen atom, a cyano group, a nitro group, an amino group, an alkyl group of 1 to 30 carbon atoms, an alkenyl group of 2 to 30 carbon atoms, an aryl group of 6 to 40 carbon atoms, and a combination thereof. Herein, the alkyl group, the alkenyl group, and the aryl group each optionally have an ether bond, a ketone bond, or an ester bond.

As mentioned above, the hydrocarbon group represented by $R^1$ is a substituted or unsubstituted linear, substituted or unsubstituted branched, or substituted or unsubstituted cyclic hydrocarbon group.

Examples of the linear, branched, or cyclic hydrocarbon group include, but not limited to, linear alkyl groups of 1 to 30 carbon atoms, branched alkyl groups of 3 to 30 carbon atoms, and cyclic alkyl groups of 3 to 30 carbon atoms.

Examples of the linear alkyl groups of 1 to 30 carbon atoms include, but not limited to, a methyl group, an ethyl group, a n-propyl group, a n-butyl group, a n-pentyl group, and a n-hexyl group.

Examples of the branched alkyl groups of 3 to 30 carbon atoms include, but not limited to, an isopropyl group, an isobutyl group, a tert-butyl group, a neopentyl group, and a 2-hexyl group.

Examples of the cyclic alkyl groups of 3 to 30 carbon atoms include, but not limited to, a cyclopropyl group, a cyclobutyl group, a cyclopentyl group, a cyclohexyl group, a cyclooctyl group, and a cyclodecyl group.

As mentioned above, the aryl group represented by $R^1$ is, but not limited to, an aryl group of 6 to 40 carbon atoms. Examples thereof include a phenyl group and a naphthyl group.

As mentioned above, the alkenyl group represented by $R^1$ is, but not limited to a substituted or unsubstituted alkenyl group. Examples thereof include linear alkenyl groups of 2 to 30 carbon atoms, branched alkenyl groups of 3 to 30 carbon atoms, and cyclic alkenyl groups of 3 to 30 carbon atoms.

Examples of the linear alkenyl groups of 2 to 30 carbon atoms include, but not limited to, a vinyl group, a 1-propenyl group, a 2-propenyl group (an allyl group), a 1-butenyl group, a 2-butenyl group, a 2-pentenyl group, and a 2-hexenyl group.

Examples of the branched alkenyl groups of 3 to 30 carbon atoms include, but not limited to, an isopropenyl group, an isobutenyl group, an isopentenyl group, and an isohexenyl group.

Examples of the cyclic alkenyl groups of 3 to 30 carbon atoms include, but not limited to, a cyclopropenyl group, a cyclobutenyl group, a cyclopentenyl group, a cyclohexenyl group, a cyclohexenyl group, a cyclooctenyl group, and a cyclodecynyl group.

Examples of the halogen atom include a fluorine atom, a chlorine atom, a bromine atom, and an iodine atom.

In the present specification, the term "substituted" means that one or more hydrogen atoms in a functional group are substituted with a halogen atom, a hydroxy group, a cyano group, a nitro group, a heterocyclic group, a linear aliphatic hydrocarbon group of 1 to 20 carbon atoms, a branched aliphatic hydrocarbon group of 3 to 20 carbon atoms, a cyclic aliphatic hydrocarbon group of 3 to 20 carbon atoms, an aryl group of 6 to 20 carbon atoms, an aralkyl group of 7 to 30 carbon atoms, an alkoxy group of 1 to 20 carbon atoms, an amino group of 0 to 20 carbon atoms, an alkenyl group of 2 to 20 carbon atoms, an acyl group of 1 to 20 carbon atoms, an alkoxycarbonyl group of 2 to 20 carbon atoms, an alkyloyloxy group of 1 to 20 carbon atoms, an aryloyloxy group of 7 to 30 carbon atoms, or an alkylsilyl group of 1 to 20 carbon atoms, unless otherwise defined.

Examples of the unsubstituted linear aliphatic hydrocarbon group of 1 to 20 carbon atoms include a methyl group, an ethyl group, a propyl group, a butyl group, a pentyl group, a hexyl group, an octyl group, a decyl group, a dodecyl group, a hexadecyl group, and an octadecyl group.

Examples of the substituted linear aliphatic hydrocarbon group of 1 to 20 carbon atoms include a fluoromethyl group, a 2-hydroxyethyl group, a 3-cyanopropyl group, and a 20-nitrooctadecyl group.

Examples of the unsubstituted branched aliphatic hydrocarbon group of 3 to 20 carbon atoms include an isopropyl group, an isobutyl group, a tertiary butyl group, a neopentyl group, a 2-hexyl group, a 2-octyl group, a 2-decyl group, a 2-dodecyl group, a 2-hexadecyl group, and a 2-octadecyl group.

Examples of the substituted branched aliphatic hydrocarbon group of 3 to 20 carbon atoms include a 1-fluoroisopropyl group and a 1-hydroxy-2-octadecyl group.

Examples of the unsubstituted cyclic aliphatic hydrocarbon group of 3 to 20 carbon atoms include a cyclopropyl group, a cyclobutyl group, a cyclopentyl group, a cyclohexyl group, a cyclooctyl group, a cyclodecyl group, a cyclododecyl group, a cyclohexadecyl group, and a cyclooctadecyl group.

Examples of the substituted cyclic aliphatic hydrocarbon group of 3 to 20 carbon atoms include a 2-fluorocyclopropyl group and a 4-cyanocyclohexyl group.

Examples of the unsubstituted aryl group of 6 to 20 carbon atoms include a phenyl group and a naphthyl group.

Examples of the substituted aryl group of 6 to 20 carbon atoms include a 4-isopropylphenyl group, a 4-cyclohexylphenyl group, a 4-methylphenyl group, and a 6-fluoronaphthyl group.

Examples of the unsubstituted alkenyl group of 2 to 20 carbon atoms include a vinyl group, a propynyl group, a butynyl group, a pentynyl group, a hexynyl group, an octynyl group, a decynyl group, a dodecynyl group, a hexadecynyl group, and an octadecynyl group.

Examples of the substituted alkenyl group of 2 to 20 carbon atoms include a chloropropynyl group.

Examples of the halogen atom include a fluorine atom, a chlorine atom, a bromine atom, and an iodine atom.

In the formula (1A), each $R^2$ is independently a hydrogen atom, an acid crosslinking reactive group, or an acid dissociation reactive group.

In the present embodiment, the "acid crosslinking reactive group" refers to a characteristic group that reacts in the presence of a radical or an acid or an alkali and varies in solubility in an acid, an alkali, or an organic solvent for use in a coating solvent or a developing solution. Examples of the acid crosslinking reactive group include allyl groups, (meth)acryloyl groups, a vinyl group, an epoxy group, alkoxymethyl groups, and a cyanato group. The acid crosslinking reactive group is not limited thereto as long as it reacts in the presence of a radical or an acid or an alkali. The acid crosslinking reactive group preferably has the property of causing chained cleavage reaction in the presence of an acid, from the viewpoint of improvement in productivity.

In the present embodiment, the "acid dissociation reactive group" refers to a characteristic group that is cleaved in the presence of an acid to cause a change such as an alkali soluble group. Examples of the alkali soluble group include, but not particularly limited to, a phenolic hydroxy group, a carboxyl group, a sulfonic acid group, and a hexafluoroisopropanol group. A phenolic hydroxy group and a carboxyl group are preferable, and a phenolic hydroxy group is particularly preferable. The acid dissociation reactive group is not particularly limited, but can be arbitrarily selected for use from among, for example, those proposed in hydroxystyrene based resins, (meth)acrylic acid based resins, and the like for use in chemically amplified resist compositions for KrF or ArF.

Preferable examples of the acid dissociation reactive group include a group selected from the group consisting of a substituted methyl group, a 1-substituted ethyl group, a 1-substituted n-propyl group, a 1-branched alkyl group, a silyl group, an acyl group, a 1-substituted alkoxymethyl group, a cyclic ether group, an alkoxycarbonyl group, and an alkoxycarbonylalkyl group which have the property of being dissociated by an acid. It is preferable that the acid dissociation reactive group has no crosslinkable functional group.

The substituted methyl group is not particularly limited, but can be usually a substituted methyl group of 2 to 20 carbon atoms and is preferably a substituted methyl group of 4 to 18 carbon atoms and more preferably a substituted methyl group of 6 to 16 carbon atoms. Specific examples of the substituted methyl group can include, but not limited to, a methoxymethyl group, a methylthiomethyl group, an ethoxymethyl group, a n-propoxymethyl group, an iso-propoxymethyl group, a n-butoxymethyl group, a t-butoxymethyl group, a 2-methylpropoxymethyl group, an ethylthiomethyl group, a methoxyethoxymethyl group, a phenyloxymethyl group, a 1-cyclopentyloxymethyl group, a 1-cyclohexyloxymethyl group, a benzylthiomethyl group, a phenacyl group, a 4-bromophenacyl group, a 4-methoxyphenacyl group, a piperonyl group, and a substituent group represented by the following formula (13-1). Specific examples of $R^2$ in the following formula (13-1) include, but not limited to, a methyl group, an ethyl group, an isopropyl group, a n-propyl group, a t-butyl group, and a n-butyl group.

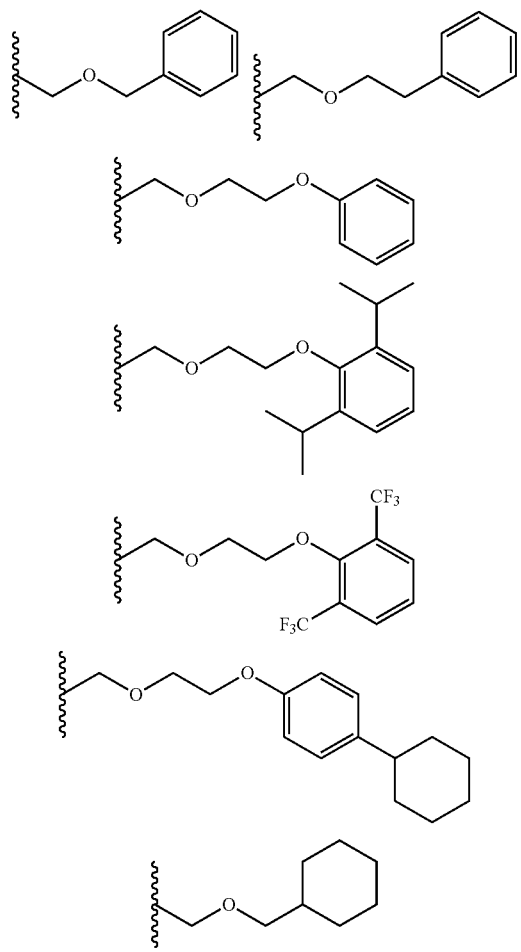

(13-1)

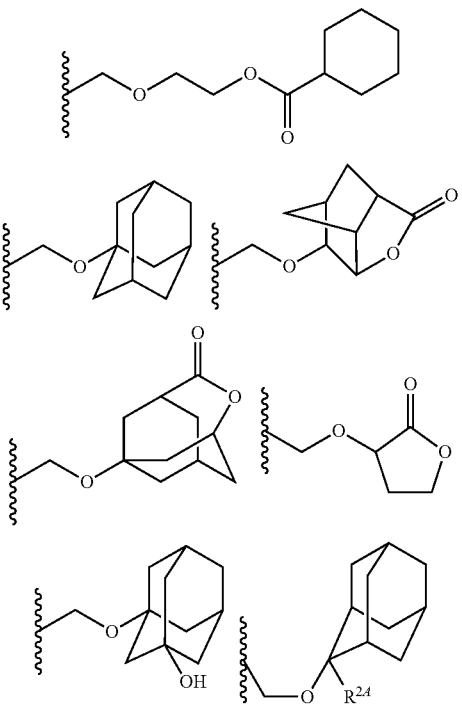

In the above formula (13-1), $R^{24}$ is an alkyl group of 1 to 4 carbon atoms.

The 1-substituted ethyl group is not particularly limited, but can be usually a 1-substituted ethyl group of 3 to 20 carbon atoms and is preferably a 1-substituted ethyl group of 5 to 18 carbon atoms and more preferably a substituted ethyl group of 7 to 16 carbon atoms. Specific examples of the 1-substituted ethyl group can include, but not limited to, a 1-methoxyethyl group, 1-methylthioethyl group, a 1,1-dimethoxyethyl group, a 1-ethoxyethyl group, a 1-ethylthioethyl group, a 1,1-diethoxyethyl group, a n-propoxyethyl group, an diethoxyethyl group, a n-propoxyethyl group, an isopropoxyethyl group, a n-butoxyethyl group, a t-butoxyethyl group, a 2-methylpropoxyethyl group, a 1-phenoxyethyl group, a 1-phenylthioethyl group, a 1,1-diphenoxyethyl group, a 1-cyclopentyloxyethyl group, a 1-cyclohexyloxyethyl group, a 1-phenylethyl group, a 1,1-diphenylethyl group, and a substituent group represented by the following formula (13-2):

Formula (13-2)

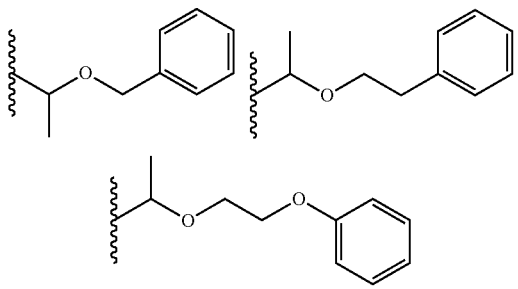

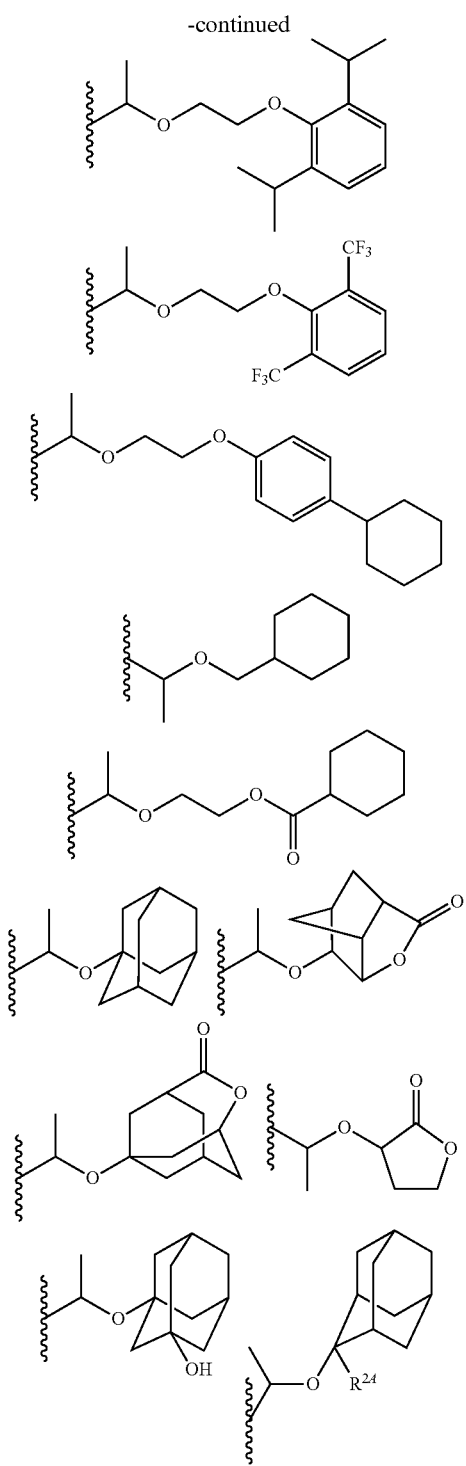

In the above formula (13-2), $R^{24}$ is as defined in the above formula (13-1).

The 1-substituted n-propyl group is not particularly limited, but can be usually a 1-substituted n-propyl group of 4 to 20 carbon atoms and is preferably a 1-substituted n-propyl group of 6 to 18 carbon atoms and more preferably a 1-substituted n-propyl group of 8 to 16 carbon atoms. Specific examples of the 1-substituted n-propyl group can include, but not limited to, a 1-methoxy-n-propyl group and a 1-ethoxy-n-propyl group.

The 1-branched alkyl group is not particularly limited, but can be usually a 1-branched alkyl group of 3 to 20 carbon atoms and is preferably a 1-branched alkyl group of 5 to 18 carbon atoms and more preferably a branched alkyl group of 7 to 16 carbon atoms. Specific examples of the 1-branched alkyl group can include, but not limited to, an isopropyl group, a sec-butyl group, a tert-butyl group, a 1,1-dimethylpropyl group, a 1-methylbutyl group, a 1,1-dimethylbutyl group, a 2-methyladamantyl group, and a 2-ethyladamantyl group.

The silyl group is not particularly limited, but can be usually a silyl group of 1 to 20 carbon atoms and is preferably a silyl group of 3 to 18 carbon atoms and more preferably a silyl group of 5 to 16 carbon atoms. Specific examples of the silyl group can include, but not limited to, a trimethylsilyl group, an ethyldimethylsilyl group, a methyldiethylsilyl group, a triethylsilyl group, a tert-butyldimethylsilyl group, a tert-butyldiethylsilyl group, a tert-butyldiphenylsilyl group, a tri-tert-butylsilyl group, and a triphenylsilyl group.

The acyl group is not particularly limited, but can be usually an acyl group of 2 to 20 carbon atoms and is preferably an acyl group of 4 to 18 carbon atoms and more preferably an acyl group of 6 to 16 carbon atoms. Specific examples of the acyl group can include, but not limited to, an acetyl group, a phenoxyacetyl group, a propionyl group, a butyryl group, a heptanoyl group, a hexanoyl group, a valeryl group, a pivaloyl group, an isovaleryl group, a lauroyl group, an adamantylcarbonyl group, a benzoyl group, and a naphthoyl group.

The 1-substituted alkoxymethyl group is not particularly limited, but can be usually a 1-substituted alkoxymethyl group of 2 to 20 carbon atoms and is preferably a 1-substituted alkoxymethyl group of 4 to 18 carbon atoms and more preferably a 1-substituted alkoxymethyl group of 6 to 16 carbon atoms. Specific examples of the 1-substituted alkoxymethyl group can include, but not limited to, a 1-cyclopentylmethoxymethyl group, a 1-cyclopentylethoxymethyl group, a 1-cyclohexylmethoxymethyl group, a 1-cyclohexylethoxymethyl group, a 1-cyclooctylmethoxymethyl group, and a 1-adamantylmethoxymethyl group.

The cyclic ether group is not particularly limited, but can be usually a cyclic ether group of 2 to 20 carbon atoms and is preferably a cyclic ether group of 4 to 18 carbon atoms and more preferably a cyclic ether group of 6 to 16 carbon atoms. Specific examples of the cyclic ether group can include, but not limited to, a tetrahydropyranyl group, a tetrahydrofuranyl group, a tetrahydrothiopyranyl group, a tetrahydrothiofuranyl group, a 4-methoxytetrahydropyranyl group, and a 4-methoxytetrahydrothiopyranyl group.

The alkoxycarbonyl group can be usually an alkoxycarbonyl group of 2 to 20 carbon atoms and is preferably an alkoxycarbonyl group of 4 to 18 carbon atoms and more preferably an alkoxycarbonyl group of 6 to 16 carbon atoms. Specific examples of the alkoxycarbonyl group can include, but not limited to, a methoxycarbonyl group, an ethoxycarbonyl group, a n-propoxycarbonyl group, an isopropoxycarbonyl group, a n-butoxycarbonyl group, a tert-butoxycarbonyl group, and a group of acid dissociation reactive groups represented by the following formula (13-3) wherein n=0.

The alkoxycarbonylalkyl group is not particularly limited, but can be usually an alkoxycarbonylalkyl group of 2 to 20 carbon atoms and is preferably an alkoxycarbonylalkyl group of 4 to 18 carbon atoms and more preferably an alkoxycarbonylalkyl group of 6 to 16 carbon atoms. Specific examples of the alkoxycarbonylalkyl group can include, but not limited to, a methoxycarbonylmethyl group, an ethoxycarbonylmethyl group, a n-propoxycarbonylmethyl group, an isopropoxycarbonylmethyl group, a n-butoxycarbonylmethyl group, and a group of acid dissociation reactive groups represented by the following formula (13-3) wherein n=1 to 4:

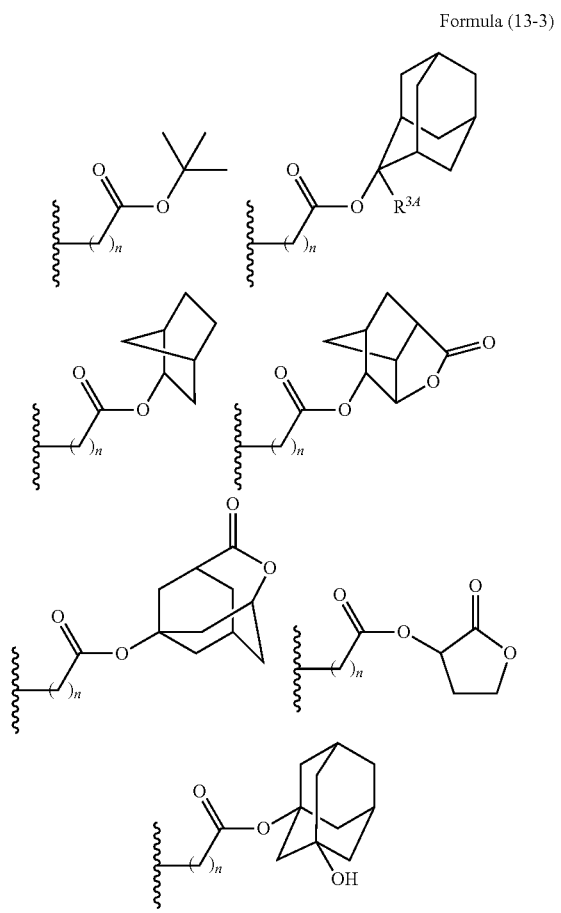

Formula (13-3)

In the above formula (13-3), $R^{3A}$ is a hydrogen atom or a linear or branched alkyl group of 1 to 4 carbon atoms; and n is an integer of 0 to 4.

Among these acid dissociation reactive groups, a substituted methyl group, a 1-substituted ethyl group, a 1-substituted alkoxymethyl group, a cyclic ether group, an alkoxycarbonyl group, and an alkoxycarbonylalkyl group are preferable. From the viewpoint of exerting higher sensitivity, a substituted methyl group, a 1-substituted ethyl group, an alkoxycarbonyl group, and an alkoxycarbonylalkyl group are more preferable, and an acid dissociation reactive group having a structure selected from a cycloalkane of 3 to 12 carbon atoms, a lactone, and an aromatic ring of 6 to 12 carbon atoms is further preferable. The cycloalkane of 3 to 12 carbon atoms may be monocyclic or polycyclic and is preferably polycyclic. Specific examples of the cycloalkane of 3 to 12 carbon atoms include, but not limited to, monocycloalkanes, bicycloalkanes, tricycloalkanes, and tetracycloalkanes. More specific examples thereof include, but not limited to: monocycloalkanes such as cyclopropane, cyclobutane, cyclopentane, and cyclohexane; and polycycloalkanes such as adamantane, norbornane, isobornane, tricyclodecane, and tetracyclodecane. Among them, adamantane, tricyclodecane, and tetracyclodecane are preferable, and adamantane and tricyclodecane are more preferable. The cycloalkane of 3 to 12 carbon atoms may have a substituent group. Examples of the lactone include, but not limited to, cycloalkane groups of 3 to 12 carbon atoms having a butyrolactone or lactone group. Examples of the aromatic ring of 6 to 12 carbon atoms include, but not limited to, a benzene ring, a naphthalene ring, an anthracene ring, a phenanthrene ring, and a pyrene ring. A benzene ring and a naphthalene ring are preferable, and a naphthalene ring is more preferable.

Particularly, a group of acid dissociation reactive groups selected from the group consisting of groups represented by the following formula (13-4) is preferable because of high resolution:

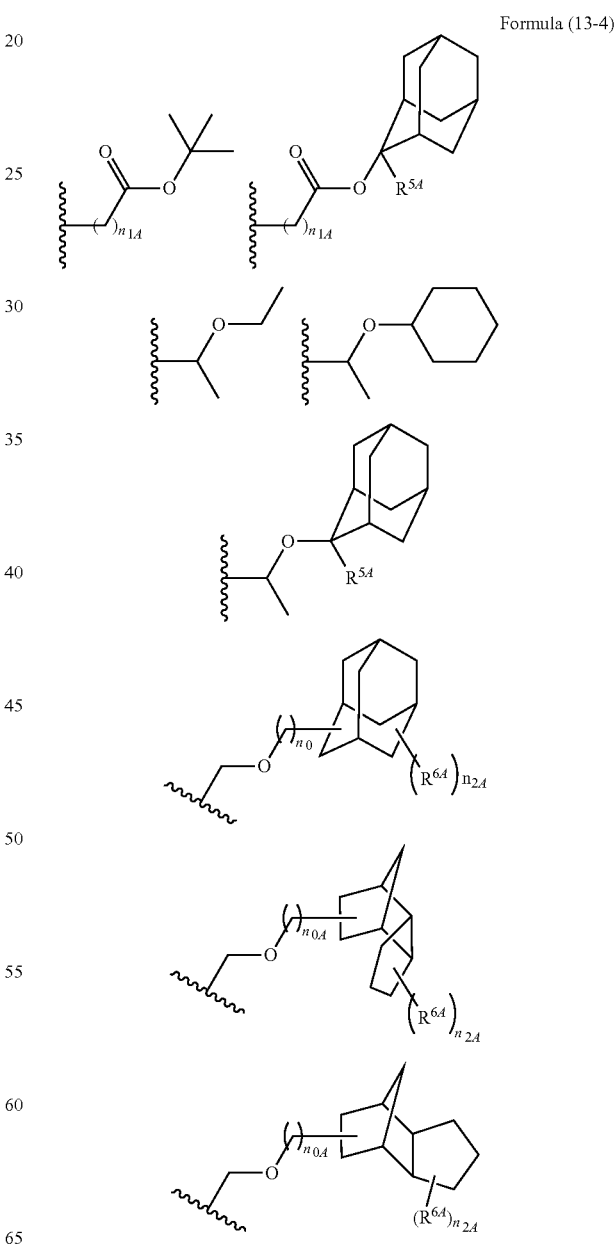

Formula (13-4)

-continued

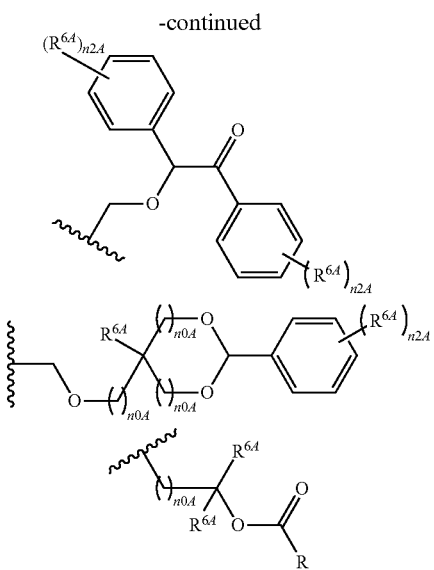

In the above formula (13-4), $R^{54}$ is a hydrogen atom or a linear or branched alkyl group of 1 to 4 carbon atoms; $R^{64}$ is a hydrogen atom, a linear or branched alkyl group of 1 to 4 carbon atoms, a cyano group, a nitro group, a heterocyclic group, a halogen atom, or a carboxyl group; $n_{1A}$ is an integer of 0 to 4; $n_{2A}$ is an integer of 1 to 5; and $n_{0A}$ is an integer of 0 to 4.

Owing to the structural features mentioned above, the compound represented by the above formula (1A) has high heat resistance attributed to its rigidity despite a low molecular weight and can be used even under high temperature baking conditions. Also, the material for lithography of the present embodiment has such a low molecular weight and can be baked at a high temperature, while the material for lithography of the present embodiment has high sensitivity and can further impart a good shape to a resist pattern, because of comprising the tellurium-containing compound.

In the present embodiment, the compound represented by the above formula (1A) is preferably a compound represented by the following formula (1B) from the viewpoint of solubility in a safe solvent:

Formula (1B)

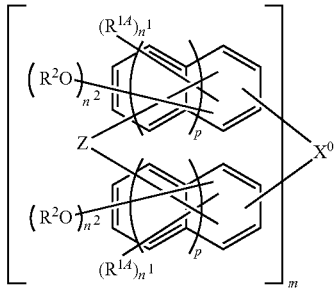

(In the formula (1B), $X^0$, Z, m, and p are as defined in the above formula (A-3); each $R^{14}$ is independently an alkyl group, an aryl group, an alkenyl group, or a halogen atom; each $R^2$ is independently a hydrogen atom, an acid cross-linking reactive group, or an acid dissociation reactive group; each $n^1$ is independently an integer of 0 to (5+2×p); and each $n^2$ is independently an integer of 0 to (5+2×p), provided that at least one $n^2$ is an integer of 1 to (5+2×p).)

In the present embodiment, the compound represented by the above formula (1B) is preferably a compound represented by the following formula (2A) from the viewpoint of solubility in a safe solvent and the properties of a resist pattern:

Formula (2A)

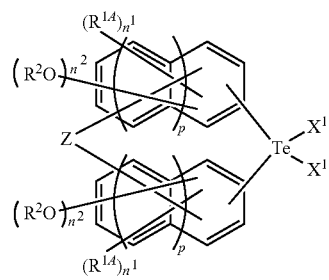

(In the formula (2A), Z, $R^1$, $R^2$, p, $n^1$, and $n^2$ are as defined in the above formula (1B); and each $X^1$ is independently a monovalent group containing an oxygen atom, a monovalent group containing a sulfur atom, a monovalent group containing a nitrogen atom, a hydrocarbon group, a hydrogen atom, or a halogen atom.)

In the present embodiment, the compound represented by the above formula (2A) is preferably a compound represented by the following formula (3A) from the viewpoint of heat resistance:

Formula (3A)

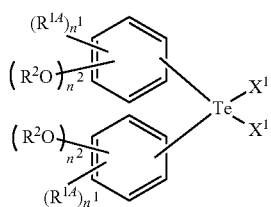

(In the formula (3A), $R^{14}$, $R^2$, $X^1$, $n^1$, and $n^2$ are as defined in the above formula (2A).)

In the present embodiment, the compound represented by the above formula (3A) is preferably a compound represented by the following general formula (4A) from the viewpoint of easy production:

Formula (4A)

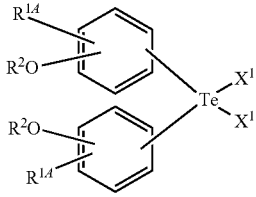

(In the formula (4A), $R^1$, $R^2$, and $X^1$ are as defined above.)

In the present embodiment, $X^1$ in the formulae (2A), (3A), and (4A) is more preferably a halogen atom from the viewpoint of easy production.

In the present embodiment, the compound represented by the above formula (1B) is preferably a compound represented by the following formula (2B) from the viewpoint of solubility in a safe solvent and the properties of a resist pattern:

Formula (2B)

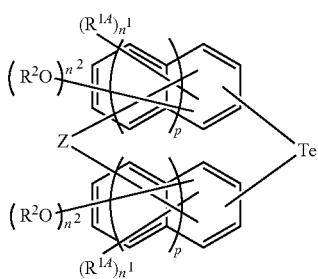

(In the formula (2B), Z, $R^{1A}$, $R^2$, p, $n^1$, and $n^2$ are as defined in the above formula (1B).)

In the present embodiment, the compound represented by the above formula (2B) is preferably a compound represented by the following formula (3B) from the viewpoint of heat resistance:

Formula (3B)

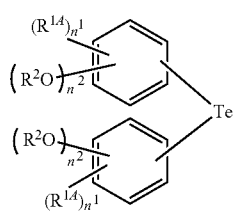

(In the formula (3B), $R^{1A}$, $R^2$, $n^1$, and $n^2$ are as defined in the above formula (2B).)

In the present embodiment, the compound represented by the above formula (3B) is preferably a compound represented by the following general formula (4B) from the viewpoint of easy production:

Formula (4B)

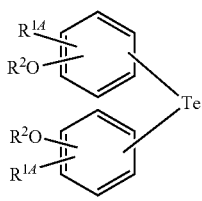

(In the formula (4B), $R^1$, $R^2$, and $X^1$ are as defined in the above formula (3B).)

In the present embodiment, in the case of forming a positive type pattern by alkaline development or in the case of forming a negative type pattern by organic development, the compound represented by the above formula (1A) preferably has at least one acid dissociation reactive group as $R^{2'}$. Such a tellurium-containing compound having at least one acid dissociation reactive group can be a tellurium-containing compound represented by the following formula (1A'):

Formula (1A')

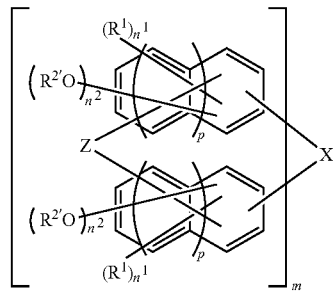

(In the formula (1A'), X, Z, m, p, $R^1$, $n^1$, and $n^2$ are as defined in the above formula (1A); and each $R^{2'}$ is independently a hydrogen atom, an acid crosslinking reactive group, or an acid dissociation reactive group, and at least one $R^{2'}$ is an acid dissociation reactive group.)

In the present embodiment, in the case of forming a negative type pattern by alkaline development, a tellurium-containing compound wherein all of $R^2$ are hydrogen atoms can be used as the compound represented by the above formula (1A). Such a compound can be a compound represented by the following general formula (1A").

Formula (1A")

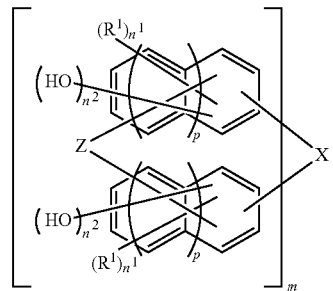

(In the above formula (1A"), X, Z, $R^1$, m, p, $n^1$, and $n^2$ are as defined in the formula (1A).)

In the present embodiment, in the case of forming a positive type pattern by alkaline development or in the case of forming a negative type pattern by organic development, the compound represented by the above formula (1B) preferably has at least one acid dissociation reactive group as $R^{2'}$. Such a tellurium-containing compound having at least one acid dissociation reactive group can be a tellurium-containing compound represented by the following formula (1B'):

Formula (1B')

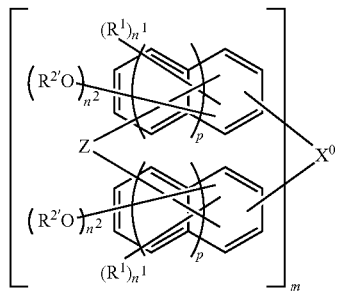

(In the formula (1B'), $X^0$, Z, m, p, $R^{14}$, $n^1$, and $n^2$ are as defined in the above formula (1B); and each $R^{2'}$ is independently a hydrogen atom or an acid dissociation reactive group, and at least one $R^{2'}$ is an acid dissociation reactive group.)

In the present embodiment, in the case of forming a negative type pattern by alkaline development, a tellurium-containing compound wherein all of $R^2$ are hydrogen atoms can be used as the compound represented by the above formula (1B). Such a compound can be a compound represented by the following general formula (1B"):

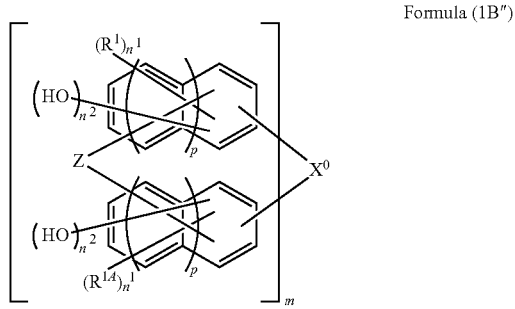

Formula (1B")

(In the formula (1B""), $X^0$, Z, m, p, $R^{14}$, $n^1$, and $n^2$ are as defined in the above formula (1B).)

In the present embodiment, a method for producing the compound represented by the above formula (A-1) is not particularly limited, and the compound represented by the above formula (A-1) can be obtained, for example, by reacting an alkoxybenzene with a corresponding tellurium halide to obtain a polyalkoxybenzene compound, subsequently performing reduction reaction with a reducing agent such as boron tribromide to obtain a polyphenol compound, and introducing an acid dissociation reactive group to at least one phenolic hydroxy group of the obtained polyphenol compound by a publicly known method.

Also, the compound represented by the above formula (A-1) can be obtained by reacting a phenol or a thiophenol with a corresponding tellurium halide to obtain a polyphenol compound, and introducing an acid dissociation reactive group to at least one phenolic hydroxy group of the obtained polyphenol compound by a publicly known method.

Further, the compound represented by the above formula (A-1) can be obtained by reacting a phenol or a thiophenol with a corresponding aldehyde containing tellurium or ketone containing tellurium in the presence of an acid or basic catalyst to obtain a polyphenol compound, and introducing an acid dissociation reactive group to at least one phenolic hydroxy group of the obtained polyphenol compound by a publicly known method.

The tellurium-containing compound can be synthesized, for example, by reacting tellurium tetrachloride (tellurium (IV) tetrachloride) with a substituted or unsubstituted phenol derivative in the presence of a basic catalyst, as mentioned later, though the synthesis method is not particularly limited thereto. Specifically, the material for lithography of the present embodiment can be produced by a method for producing the material for lithography, comprising the step of reacting tellurium tetrachloride with a substituted or unsubstituted phenol derivative in the presence of a basic catalyst to synthesize the tellurium-containing compound.

Examples of the tellurium halide include, but not particularly limited to, tellurium(IV) tetrafluoride, tellurium(IV) tetrachloride, tellurium(IV) tetrabromide, and tellurium(IV) tetraiodide.

Examples of the alkoxybenzene include, but not particularly limited to, methoxybenzene, dimethoxybenzene, methylmethoxybenzene, methyldimethoxybenzene, phenylmethoxybenzene, phenyldimethoxybenzene, methoxynaphthalene, dimethoxynaphthalene, ethoxybenzene, diethoxybenzene, methylethoxybenzene, methyldiethoxybenzene, phenylethoxybenzene, phenyldiethoxybenzene, ethoxynaphthalene, and diethoxynaphthalene.

Upon producing the polyalkoxybenzene compound, a reaction solvent may be used. The reaction solvent is not particularly limited as long as the reaction of the alkoxybenzene used with the corresponding tellurium halide proceeds. For example, water, methylene chloride, methanol, ethanol, propanol, butanol, tetrahydrofuran, dioxane, dimethylacetamide, N-methylpyrrolidone, or a mixed solvent thereof can be used.

The amount of the solvent is not particularly limited and can be in the range of, for example, 0 to 2000 parts by mass based on 100 parts by mass of the reaction raw materials.

Upon producing the polyphenol compound containing tellurium, the reaction temperature is not particularly limited and can be arbitrarily selected according to the reactivity of the reaction raw materials, but is preferably in the range of 10 to 200° C.

Examples of a method for producing the polyalkoxybenzene include, but not particularly limited to, a method of charging the alkoxybenzene and the corresponding tellurium halide in one portion, and a method of dropping the alkoxybenzene and the corresponding tellurium halide. After the reaction terminates, the temperature of the reaction vessel can be elevated to 130 to 230° C. in order to remove unreacted raw materials, etc. present in the system, and volatile portions can be removed at about 1 to 50 mmHg.

The amounts of the raw materials upon producing the polyalkoxybenzene compound are not particularly limited. The reaction can be proceeded by using, for example, 1 mol to an excess of the alkoxybenzene based on 1 mol of the tellurium halide, and reacting them at 20 to 150° C. at normal pressure for about 20 minutes to 100 hours.

Upon producing the polyalkoxybenzene compound, the target component can be isolated by a publicly known method after the reaction terminates. Examples of the method for isolating the target component include, but not particularly limited to, a method which involves concentrating the reaction solution, precipitating the reaction product by the addition of pure water, cooling the reaction solution to room temperature, then separating the precipitates by filtration, filtering and drying the obtained solid matter, then separating and purifying the solid matter from by-products by column chromatography, and distilling off the solvent, followed by filtration and drying to obtain the target compound.

The polyphenol compound can be obtained by reducing the polyalkoxybenzene compound. The reduction reaction can be performed using a reducing agent such as boron tribromide. Upon producing the polyphenol compound, a reaction solvent may be used. The reaction time, the reaction temperature, the amounts of raw materials, and an isolation method are not particularly limited as long as the polyphenol compound is obtained.

A publicly known method can be used as a method for introducing an acid dissociation reactive group to at least one phenolic hydroxy group of the polyphenol compound. An acid dissociation reactive group can be introduced to at least one phenolic hydroxy group of the polyphenol compound, for example, as described below. A compound for introducing the acid dissociation reactive group can be synthesized by a publicly known method or easily obtained. Examples thereof include, but not particularly limited to, acid chlorides, acid anhydrides, active carboxylic acid derivative compounds such as dicarbonate, alkyl halides, vinyl alkyl ethers, dihydropyran, and halocarboxylic acid alkyl esters.

For example, the polyphenol compound is dissolved or suspended in an aprotic solvent such as acetone, tetrahydrofuran (THF), propylene glycol monomethyl ether acetate, dimethylacetamide, or N-methylpyrrolidone. Subsequently, a vinyl alkyl ether such as ethyl vinyl ether, or dihydropyran is added to the solution or the suspension, and the mixture is reacted at 20 to 60° C. at normal pressure for 6 to 72 hours in the presence of an acid catalyst such as pyridinium p-toluenesulfonate. The reaction solution is neutralized with an alkali compound and added to distilled water to precipitate a white solid. Then, the separated white solid can be washed with distilled water and dried to obtain the compound represented by the above formula (A).

The acid catalyst is not particularly limited. Inorganic acids and organic acids are widely known as well-known acid catalysts, and examples include, but not particularly limited to, inorganic acids such as hydrochloric acid, sulfuric acid, phosphoric acid, hydrobromic acid, and hydrofluoric acid; organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, and naphthalenedisulfonic acid; Lewis acids such as zinc chloride, aluminum chloride, iron chloride, and boron trifluoride; and solid acids such as tungstosilicic acid, tungstophosphoric acid, silicomolybdic acid, and phosphomolybdic acid. Among them, organic acids and solid acids are preferable from the viewpoint of production, and hydrochloric acid or sulfuric acid is preferably used from the viewpoint of production such as easy availability and handleability. The acid catalysts can be used alone as one kind, or can be used in combination of two or more kinds.

Also, for example, the polyphenol compound is dissolved or suspended in an aprotic solvent such as acetone, THF, propylene glycol monomethyl ether acetate, dimethylacetamide, or N-methylpyrrolidone. Subsequently, an alkyl halide such as ethyl chloromethyl ether or a halocarboxylic acid alkyl ester such as methyladamantyl bromoacetate is added to the solution or the suspension, and the mixture is reacted at 20 to 110° C. at normal pressure for 6 hours to 72 hours in the presence of an alkali catalyst such as potassium carbonate. The reaction solution is neutralized with an acid such as hydrochloric acid and added to distilled water to precipitate a white solid. Then, the separated white solid can be washed with distilled water and dried to obtain the compound represented by the above formula (A).

The basic catalyst is not particularly limited and can be arbitrarily selected from well-known basic catalysts, and examples include: inorganic bases such as metal hydrides (alkali metal hydrides such as sodium hydride and potassium hydride, etc.), metal alcohol salts (alcohol salts of alkali metals such as sodium methoxide and potassium ethoxide), metal hydroxides (alkali metal or alkaline earth metal hydroxides such as sodium hydroxide and potassium hydroxide, etc.), metal carbonates (alkali metal or alkaline earth metal carbonates such as sodium carbonate and potassium carbonate, etc.), and alkali metal or alkaline earth metal bicarbonates such as sodium bicarbonate and potassium bicarbonate; and organic bases such as amines (for example, tertiary amines (trialkylamines such as triethylamine, aromatic tertiary amines such as N,N-dimethylaniline, and heterocyclic tertiary amines such as 1-methylimidazole), and carboxylic acid metal salts (acetic acid alkali metal or alkaline earth metal salts such as sodium acetate and calcium acetate, etc.). Sodium carbonate or potassium carbonate is preferable from the viewpoint of production such as easy availability and handleability. One kind or two or more kinds of the basic catalysts can be used.

The acid dissociation reactive group preferably has the property of causing chained cleavage reaction in the presence of an acid, for achieving pattern formation with higher sensitivity and higher resolution.

Specific examples of the tellurium-containing compound represented by the formula (A-1) can include the following:

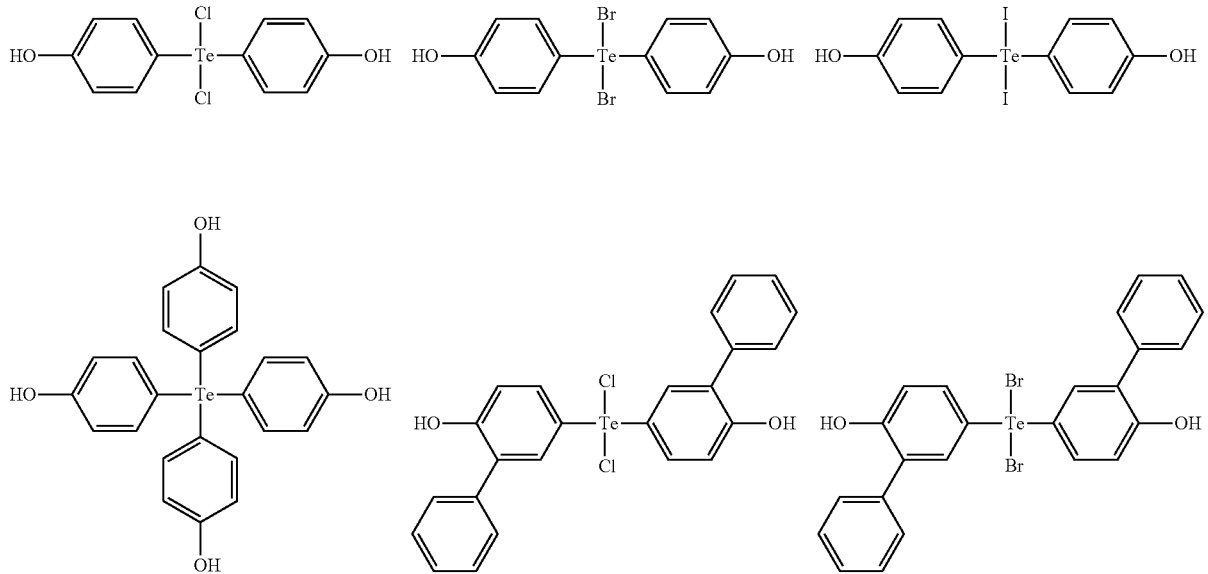

-continued
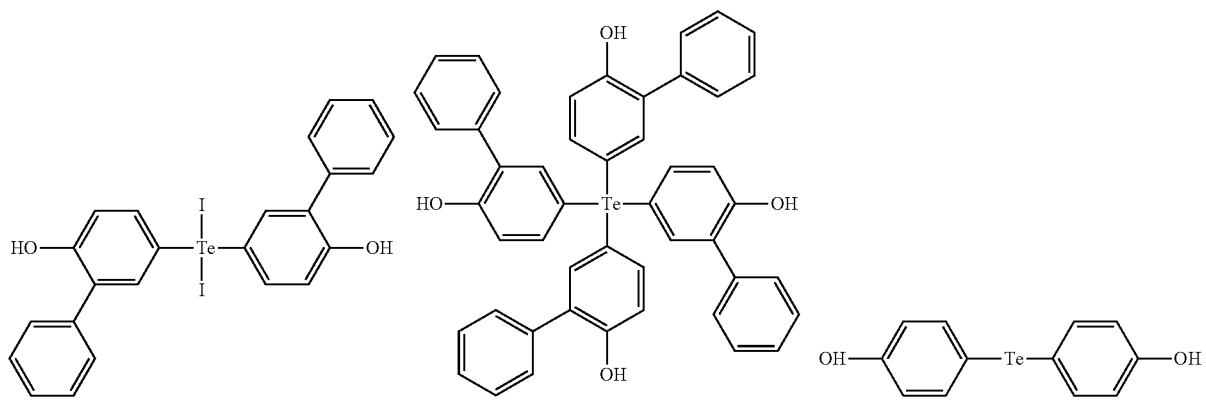
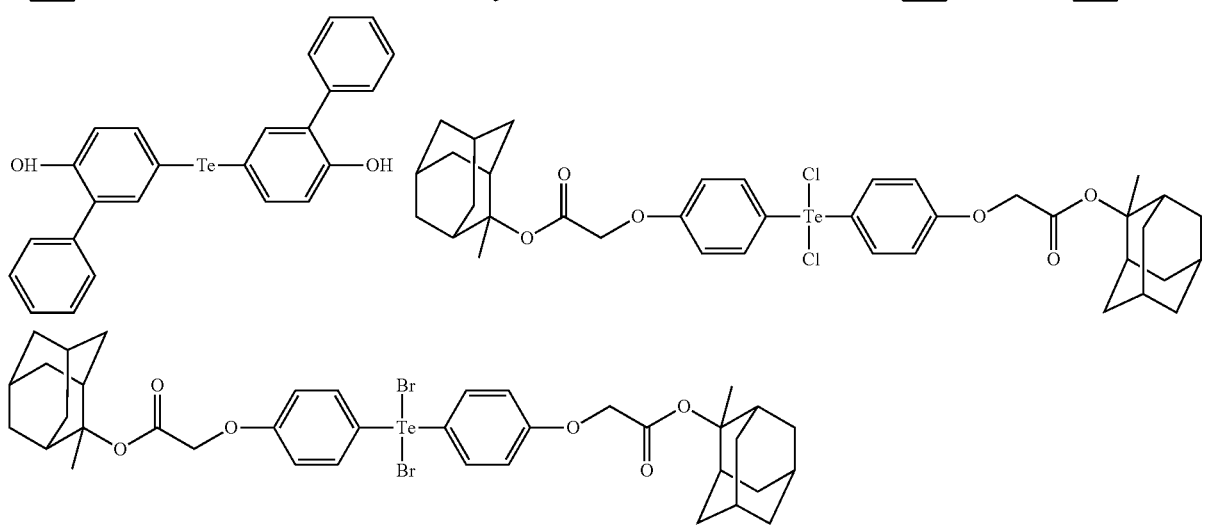
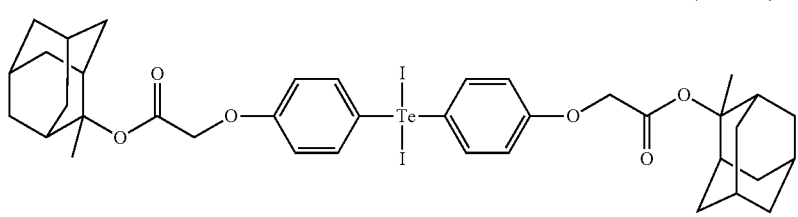
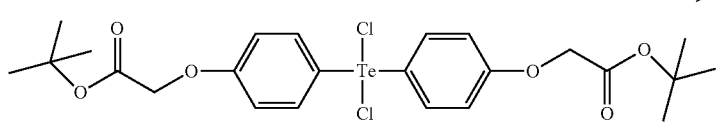
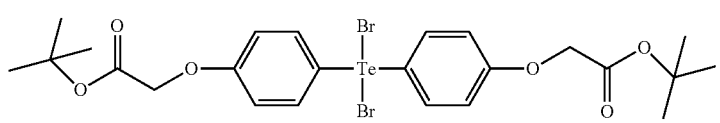
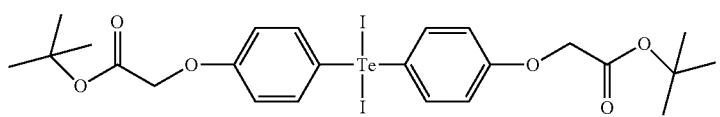

-continued
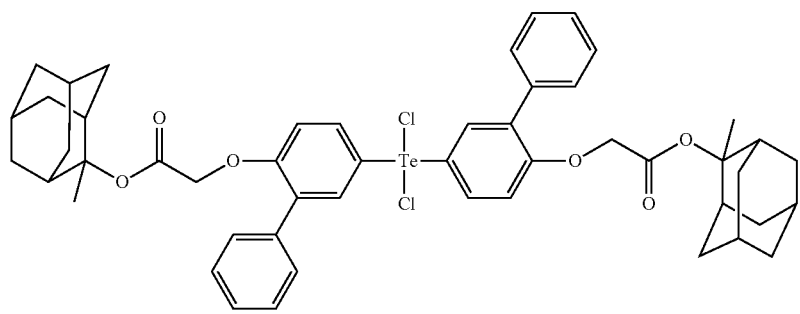
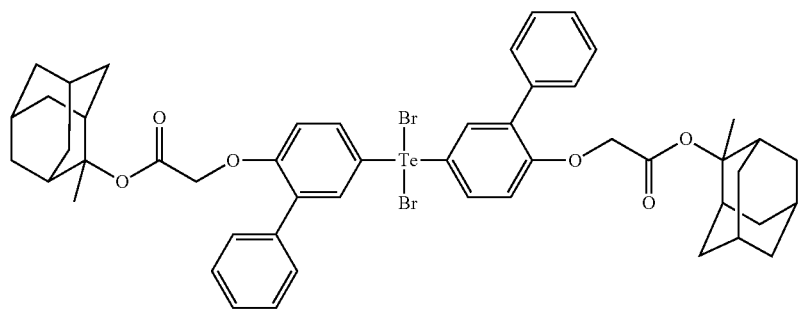
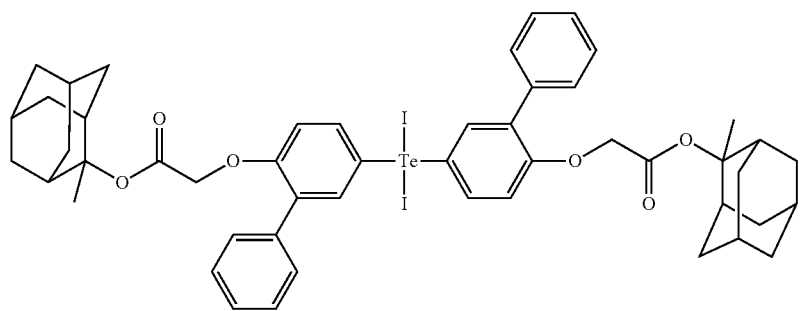
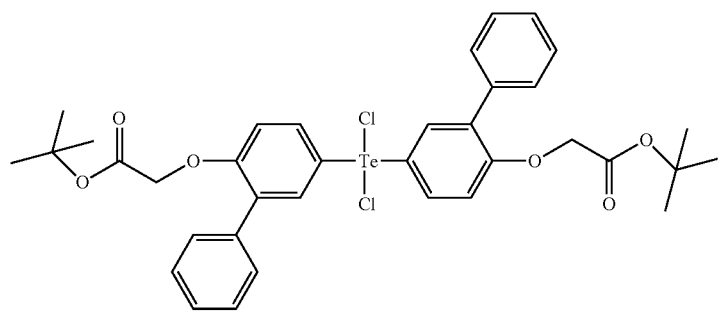
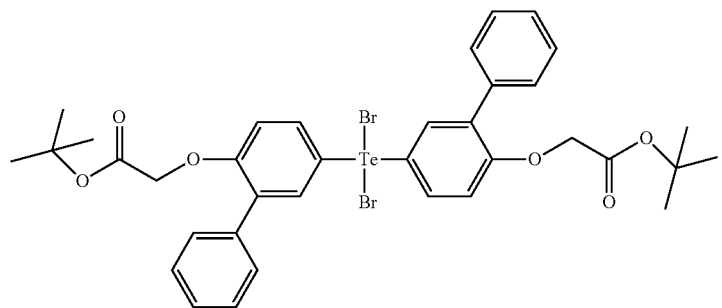

-continued
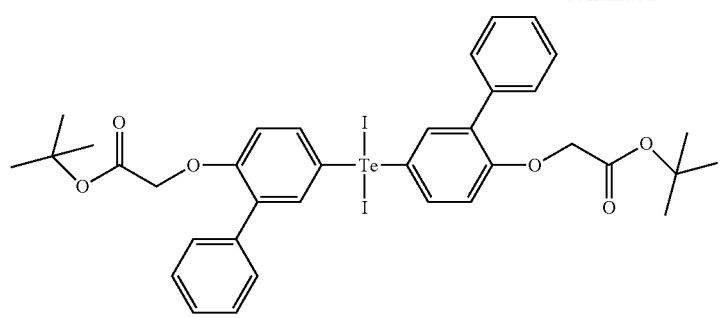
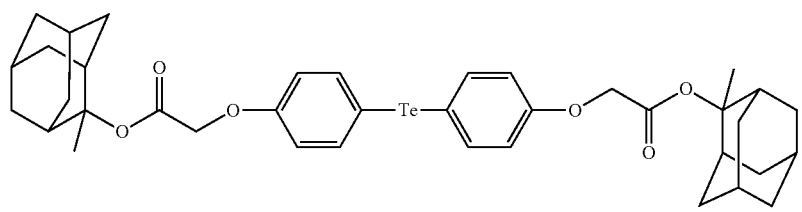
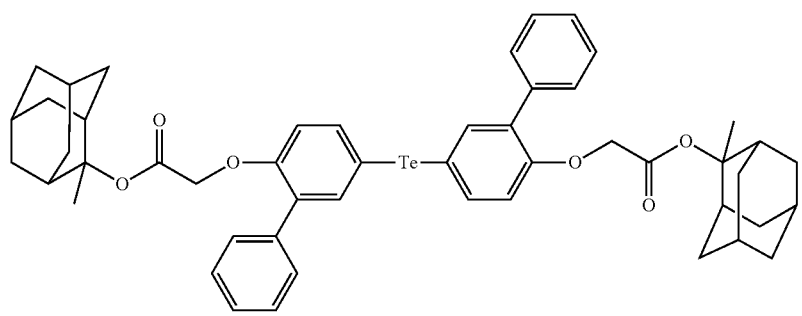
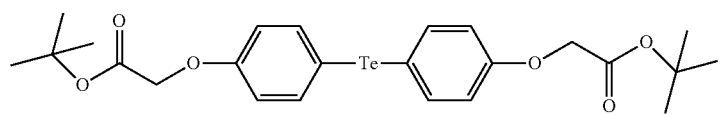
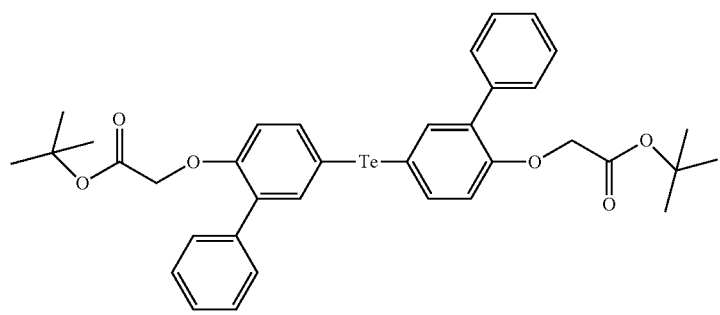

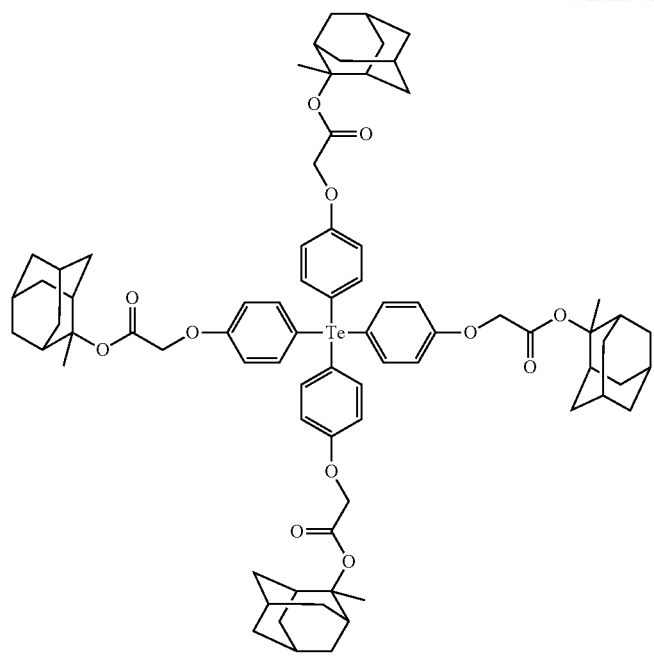
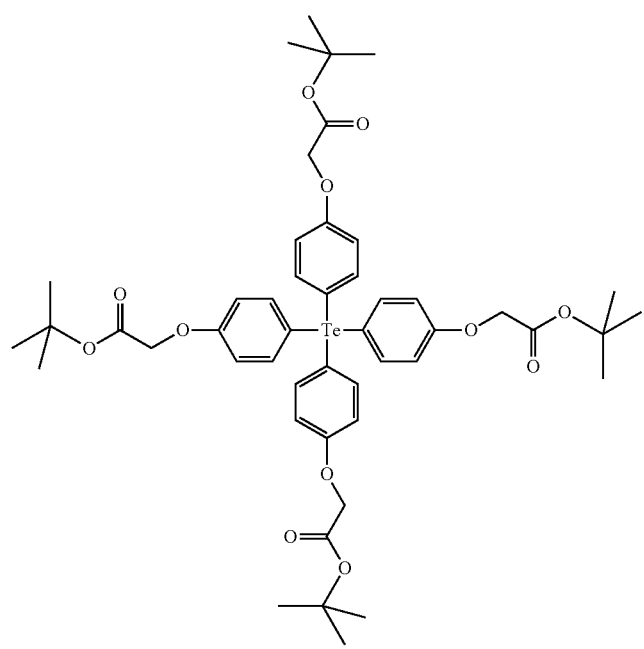

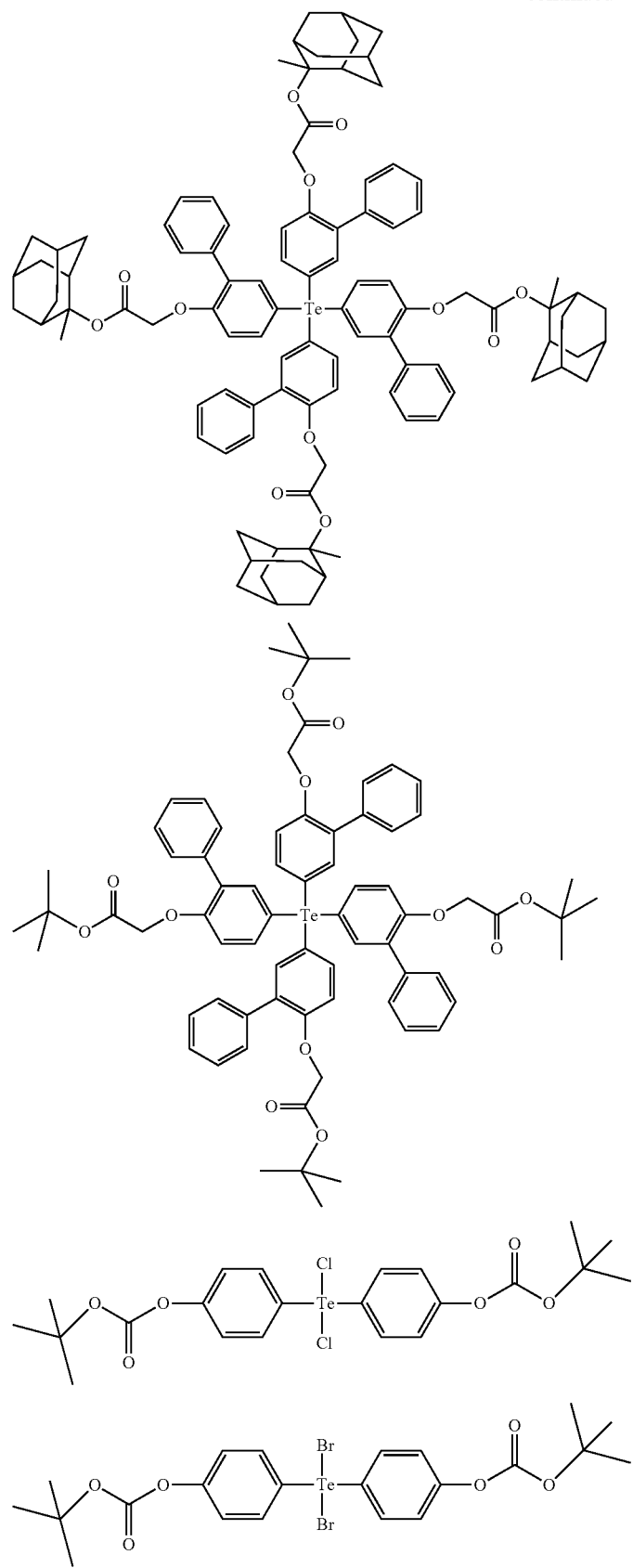

-continued
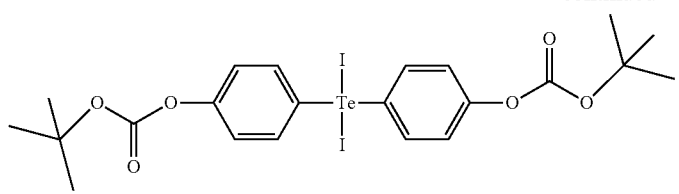
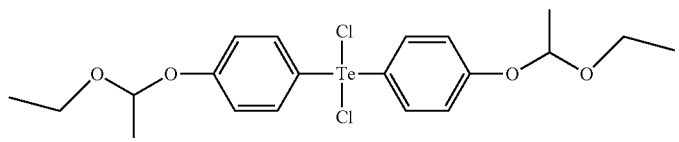
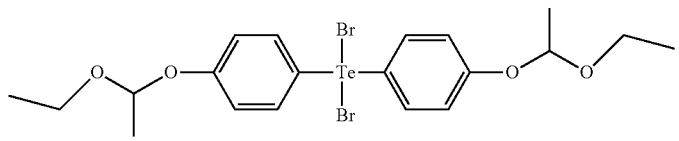
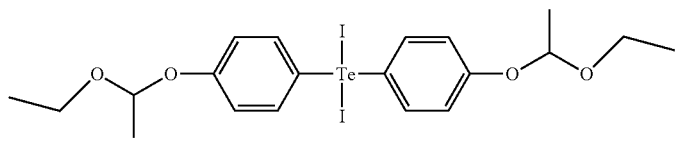
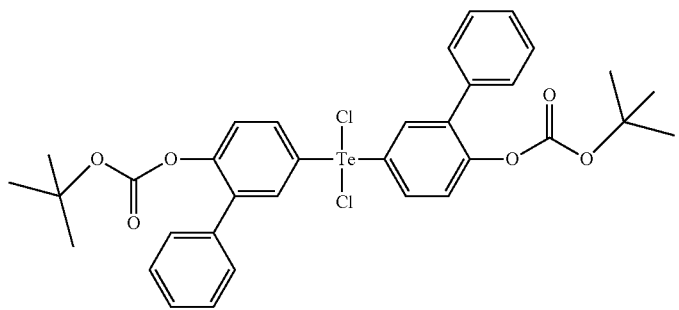
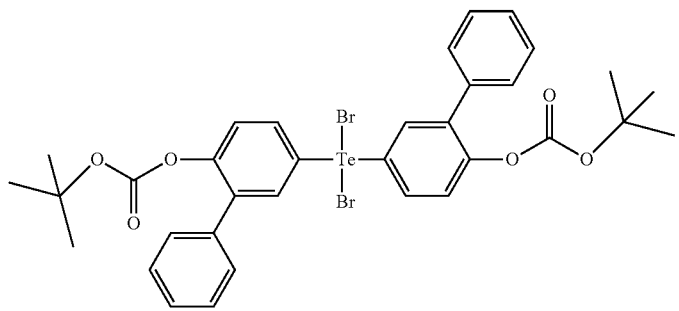
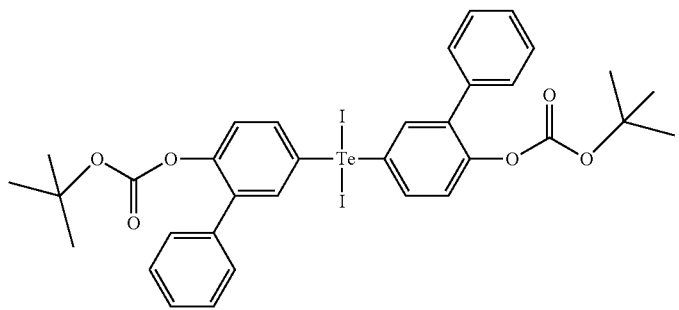

-continued
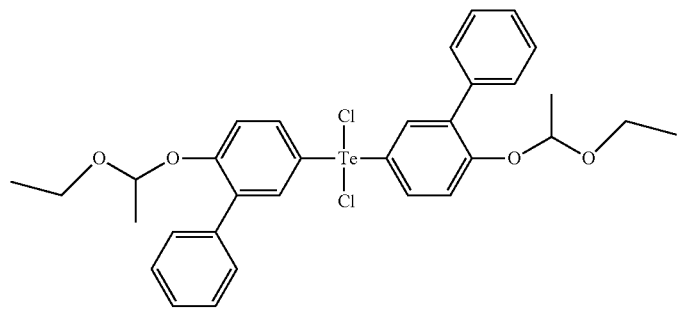
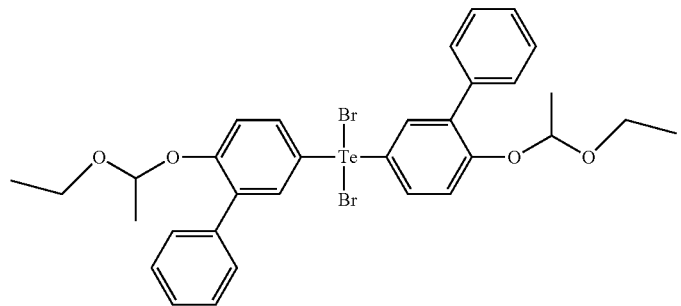
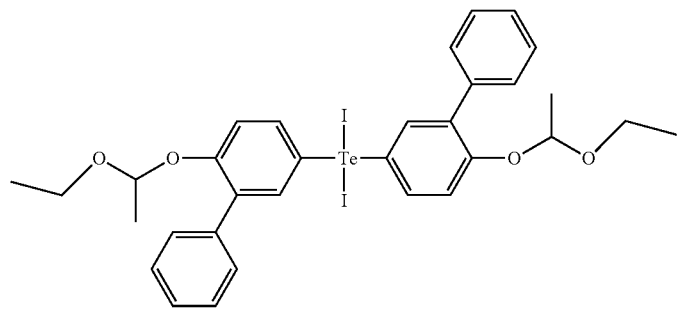
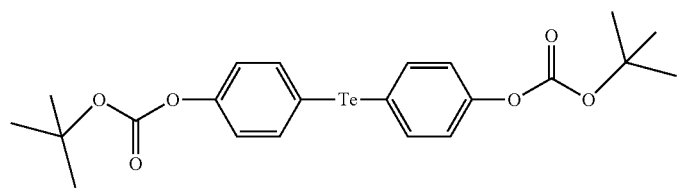
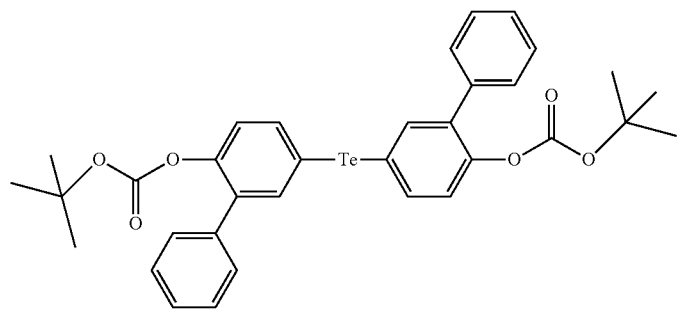
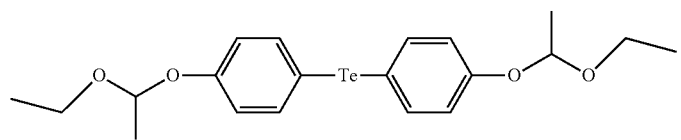

-continued
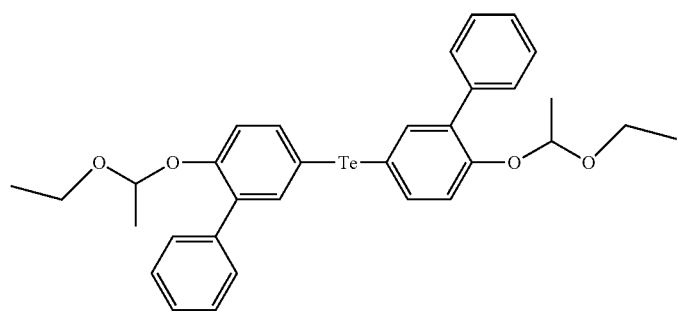
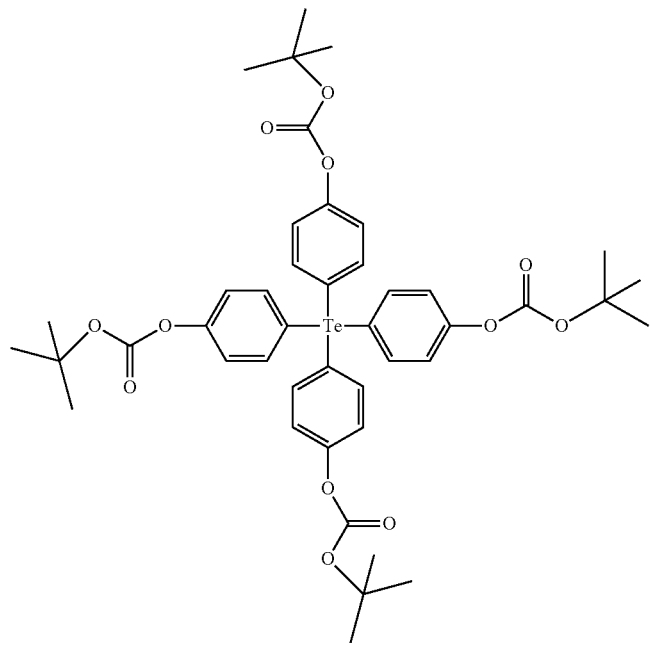
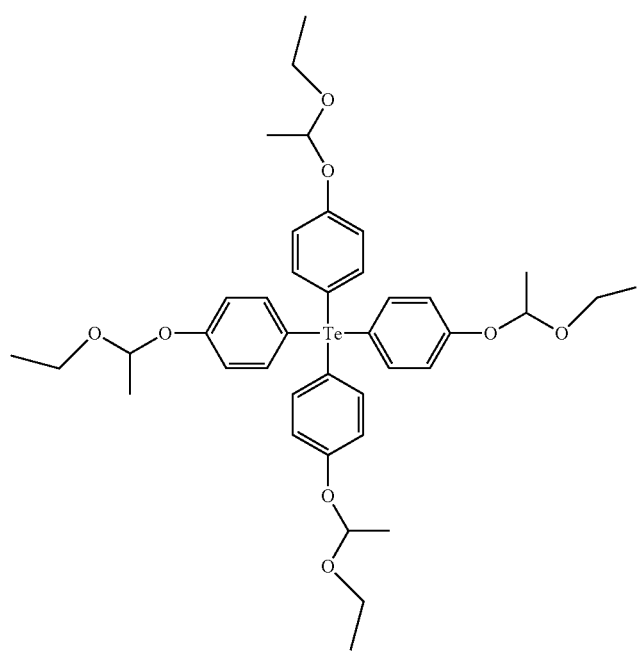

-continued

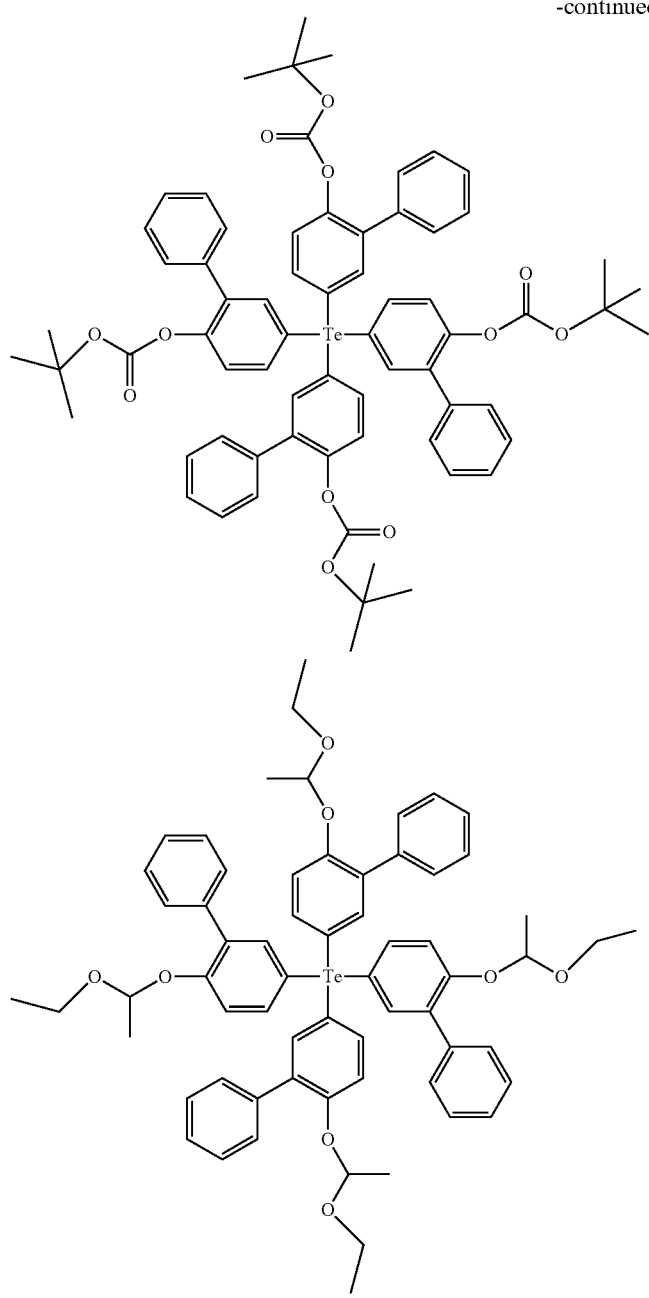

(Resin Comprising Constitutional Unit Derived from Formula (A-1))

The material for lithography of the present embodiment may contain a resin comprising a constitutional unit derived from the formula (A-1), instead of or together with the tellurium-containing compound represented by the formula (A-1). In other words, the material for lithography of the present embodiment can contain a resin obtained using the compound represented by the formula (A-1) as a monomer.

Also, the resin of the present embodiment can be obtained, for example, by reacting the compound represented by the formula (A-1) with a crosslinking compound.

As the crosslinking compound, a publicly known compound can be used without particular limitations as long as it can oligomerize or polymerize the compound represented by the formula (A-1). Specific examples thereof include, but not particularly limited to, aldehydes, ketones, carboxylic acids, carboxylic acid halides, halogen-containing compounds, amino compounds, imino compounds, isocyanates, and unsaturated hydrocarbon group-containing compounds.

As the tellurium-containing resin, for example, a resin comprising a compound derived from the compound represented by the above formula (A-1) (including, for example, a resin comprising a compound derived from the compound represented by the above formula (A-2), and a resin comprising a compound derived from the compound represented by the above formula (A-3)) as well as a resin comprising a constitutional unit represented by any of the following formulae may be used.

A resin comprising a constitutional unit represented by the following formula (B1-M):

Formula (B1-M)

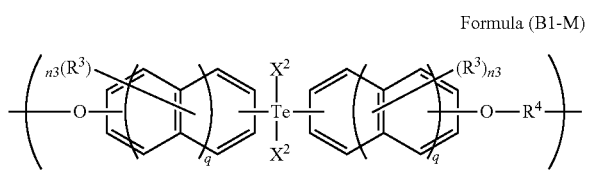

(In the formula (B1-M), each $X^2$ is independently a monovalent group containing an oxygen atom, a monovalent group containing a sulfur atom, a monovalent group containing a nitrogen atom, a hydrocarbon group, a hydrogen atom, or a halogen atom; each $R^3$ is independently a monovalent group containing an oxygen atom, a monovalent group containing a sulfur atom, a monovalent group containing a nitrogen atom, a hydrocarbon group, or a halogen atom; q is an integer of 0 to 2; $n^3$ is an integer of 0 to (4+2×q); and $R^4$ is a single bond or any structure represented by the following general formula (5).)

General formula (5)

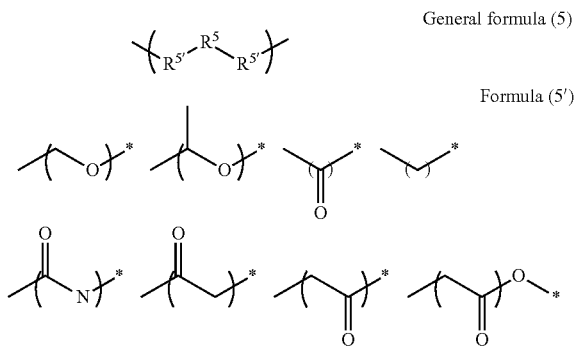

Formula (5')

(In the general formula (5), $R^5$ is a substituted or unsubstituted linear alkylene group of 1 to 20 carbon atoms, branched alkylene group of 3 to 20 carbon atoms, or cyclic alkylene group of 3 to 20 carbon atoms, or a substituted or unsubstituted arylene group of 6 to 20 carbon atoms; and each $R^{5'}$ is independently any structure of the above formula (5'). In the formula (5'), * indicates that this portion is connected to $R^5$.)

A resin comprising a constitutional unit represented by the following formula (B1-M') (a resin wherein the $R^4$ in the formula (B1-M) is a single bond):

Formula (B1-M')

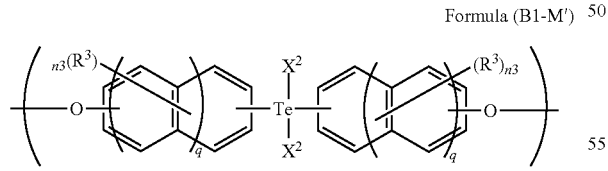

(In the formula (B1-M'), each $X^2$ is independently a monovalent group containing an oxygen atom, a monovalent group containing a sulfur atom, a monovalent group containing a nitrogen atom, a hydrocarbon group, a hydrogen atom, or a halogen atom; each $R^3$ is independently a monovalent group containing an oxygen atom, a monovalent group containing a sulfur atom, a monovalent group containing a nitrogen atom, a hydrocarbon group, or a halogen atom; q is an integer of 0 to 2; and $n^3$ is an integer of 0 to (4+2×q).)

A resin comprising a constitutional unit represented by the following formula (B2-M) (a resin comprising a constitutional unit wherein the $R^4$ in the formula (B1-M) is any structure represented by the above general formula (5)):

Formula (B2-M)

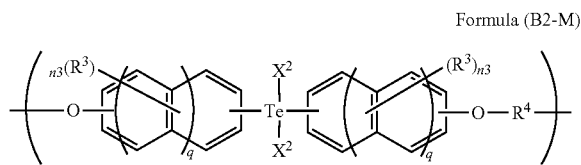

(In the formula (B2-M), $X^2$, $R^3$, q, and $n^3$ are as defined in the formula (B1-M); and $R^4$ is any structure represented by the above general formula (5).)

A resin comprising a constitutional unit represented by the following formula (B2-M'):

Formula (B2-M')

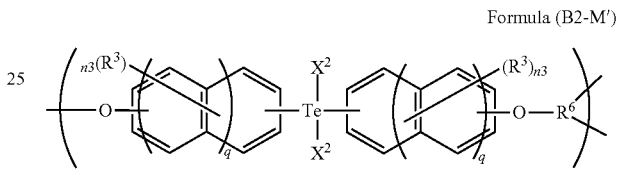

(In the formula (B2-M'), $X^2$, $R^3$, q, and $n^3$ are as defined in the formula (B1-M); and $R^6$ is any structure represented by the following general formula (6).)

General formula (6)

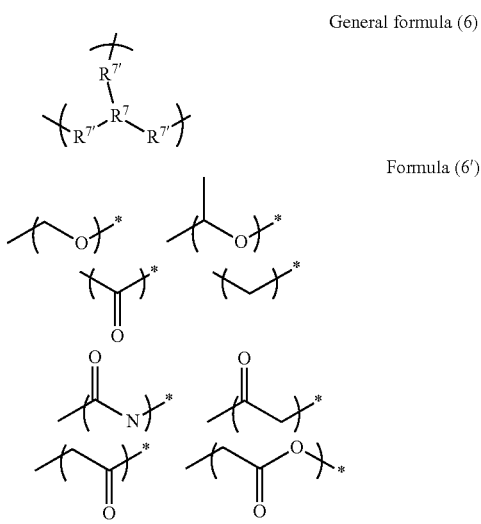

Formula (6')

(In the general formula (6), $R^7$ is a substituted or unsubstituted linear alkylene group of 1 to 20 carbon atoms, branched alkylene group of 3 to 20 carbon atoms, or cyclic alkylene group of 3 to 20 carbon atoms, or a substituted or unsubstituted arylene group of 6 to 20 carbon atoms; and each $R^{7'}$ is independently any structure of the above formula (6'). In the formula (6'), * indicates that this portion is connected to $R^7$.)

A resin comprising a constitutional unit represented by the following formula (C1):

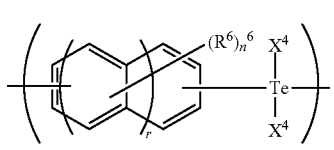

Formula (C1)

(In the formula (C1), each $X^4$ is independently a monovalent group containing an oxygen atom, a monovalent group containing a sulfur atom, a monovalent group containing a nitrogen atom, a hydrocarbon group, a hydrogen atom, or a halogen atom; each $R^6$ is independently a monovalent group containing an oxygen atom, a monovalent group containing a sulfur atom, a monovalent group containing a nitrogen atom, a hydrocarbon group, or a halogen atom; r is an integer of 0 to 2; and $n^6$ is an integer of 2 to (4+2×r).)

A resin comprising a constitutional unit represented by the following formula (B3-M):

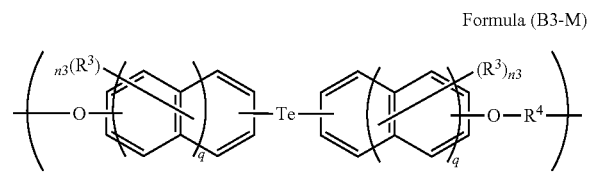

Formula (B3-M)

(In the formula (B3-M), each $R^3$ is independently a monovalent group containing an oxygen atom, a monovalent group containing a sulfur atom, a monovalent group containing a nitrogen atom, a hydrocarbon group, or a halogen atom; q is an integer of 0 to 2; $n^3$ is an integer of 0 to (4+2×q); and $R^4$ is a single bond or any structure represented by the following general formula (5).)

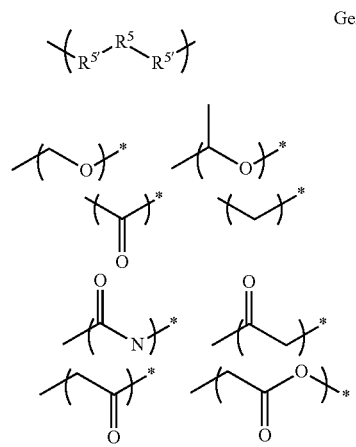

General formula (5)

Formula (5')

(In the general formula (5), $R^5$ is a substituted or unsubstituted linear alkylene group of 1 to 20 carbon atoms, branched alkylene group of 3 to 20 carbon atoms, or cyclic alkylene group of 3 to 20 carbon atoms, or a substituted or unsubstituted arylene group of 6 to 20 carbon atoms; and each $R^{5'}$ is independently any structure of the above formula (5'). In the formula (5'), * indicates that this portion is connected to $R^5$.)

A resin comprising a constitutional unit represented by the following formula (B3-M') (a resin wherein the $R^4$ in the formula (B3-M) is a single bond):

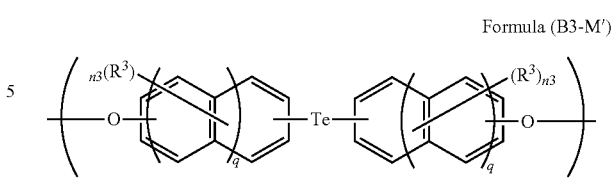

Formula (B3-M')

(In the formula (B3-M'), each $R^3$ is independently a monovalent group containing an oxygen atom, a monovalent group containing a sulfur atom, a monovalent group containing a nitrogen atom, a hydrocarbon group, or a halogen atom; q is an integer of 0 to 2; and $n^3$ is an integer of 0 to (4+2×q).)

A resin comprising a constitutional unit represented by the following formula (B4-M) (a resin comprising a constitutional unit wherein the $R^4$ in the formula (B3-M) is any structure represented by the above general formula (5)):

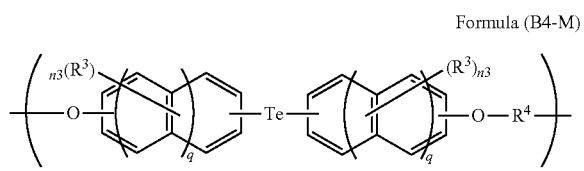

Formula (B4-M)

(In the formula (B4-M), $R^3$, q, and $n^3$ are as defined in the formula (B3-M); and $R^4$ is any structure represented by the above general formula (5).)

A resin comprising a constitutional unit represented by the following formula (B4-M'):

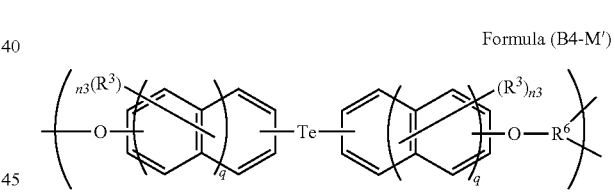

Formula (B4-M')

(In the formula (B4-M'), $R^3$, q, and $n^3$ are as defined in the formula (B3-M); and $R^6$ is any structure represented by the following general formula (6).)

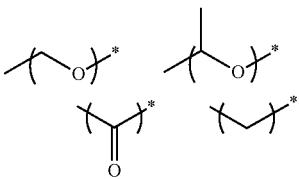

General formula (6)

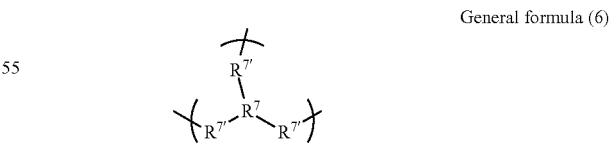

Formula (6')

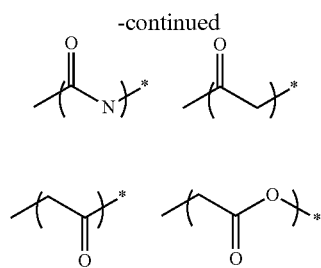

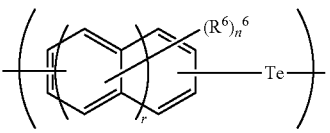

(In the general formula (6), $R^7$ is a substituted or unsubstituted linear alkylene group of 1 to 20 carbon atoms, branched alkylene group of 3 to 20 carbon atoms, or cyclic alkylene group of 3 to 20 carbon atoms, or a substituted or unsubstituted arylene group of 6 to 20 carbon atoms; and each $R^{7'}$ is independently any structure of the above formula (6'). In the formula (6'), * indicates that this portion is connected to $R^7$.)

A resin comprising a constitutional unit represented by the following formula (C2):

(In the formula (C2), each $R^6$ is independently a monovalent group containing an oxygen atom, a monovalent group containing a sulfur atom, a monovalent group containing a nitrogen atom, a hydrocarbon group, or a halogen atom; r is an integer of 0 to 2; and $n^6$ is an integer of 2 to $(4+2\times r)$.)

The resin comprising each of the constitutional units mentioned above may differ in each substituent group among the constitutional units. For example, $R^5$ in the general formula (5) for $R^4$ in the formula (B1-M) or (B3-M), or $R^6$ in the general formula (6) for the formula (B2-M') or (B4-M') may be the same or different among the constitutional units.

Specific examples of the constitutional unit derived from the formula (A-1) can include the following:

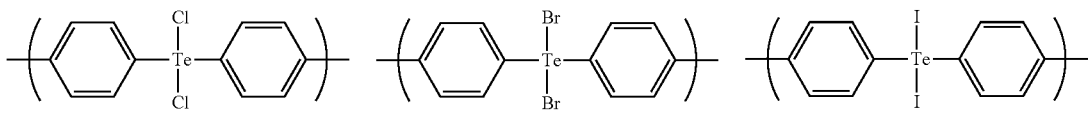

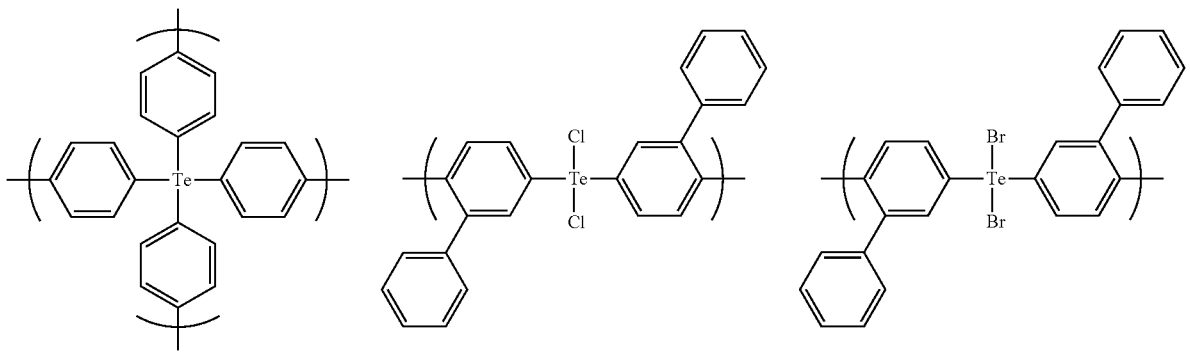

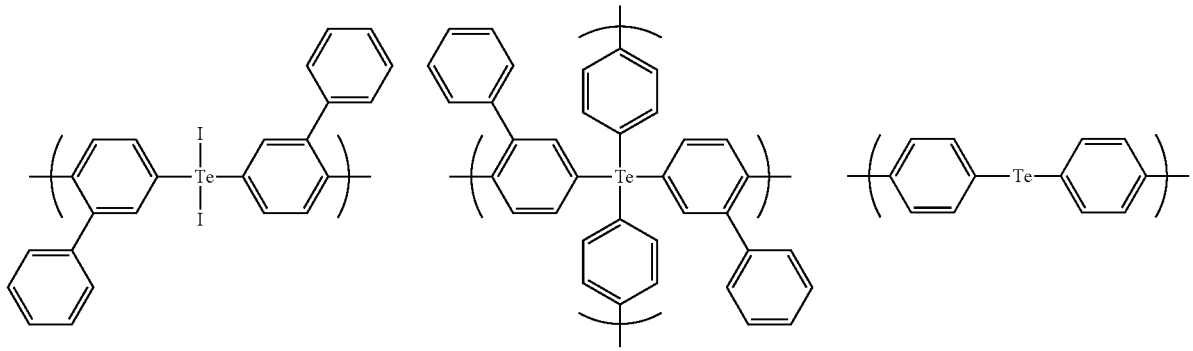

-continued
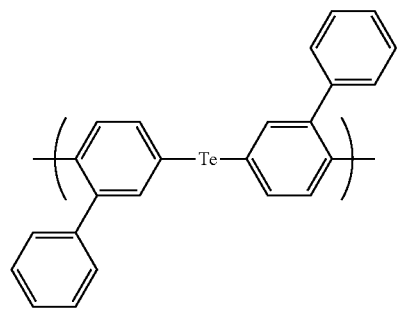
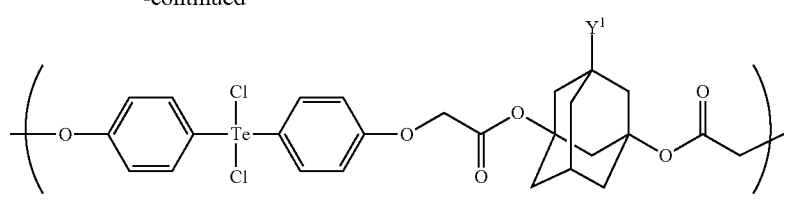
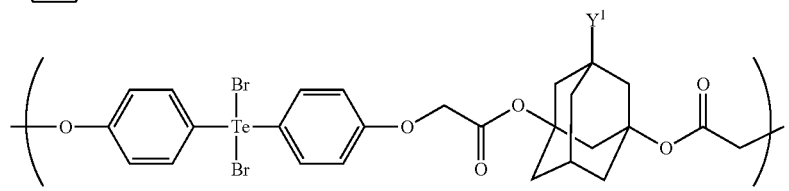
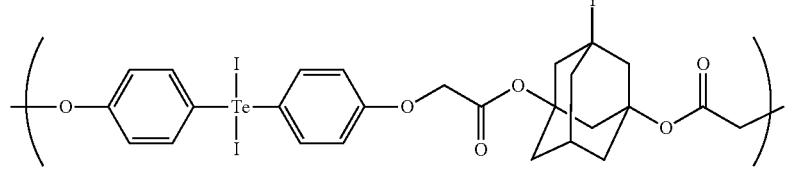
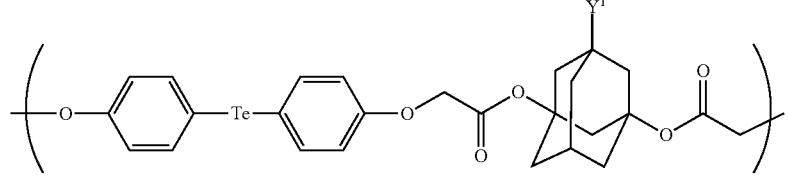
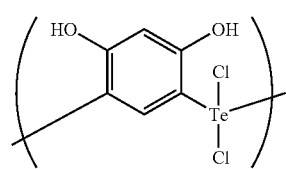
Y¹ = 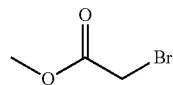
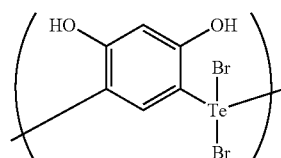 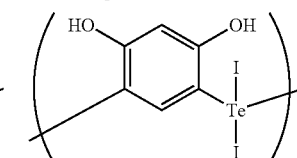 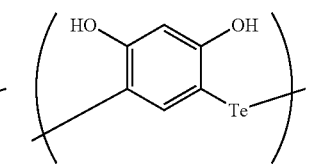 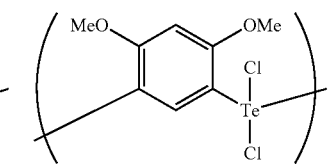
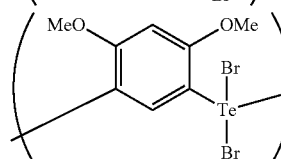 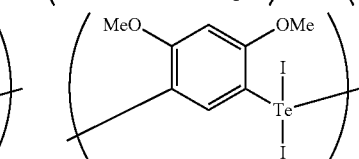 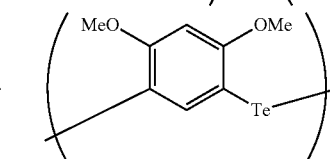
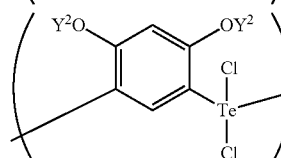 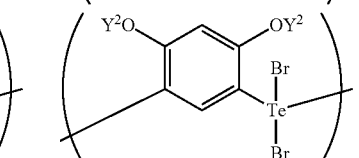 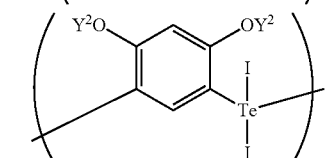
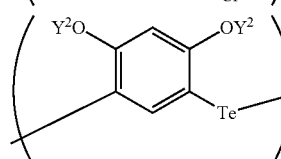 Y² = 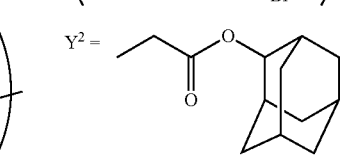 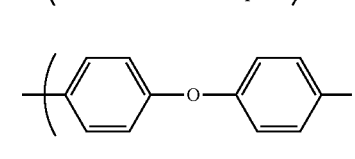
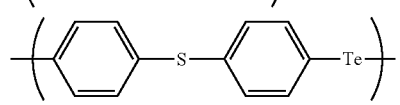

[Method for Purifying Compound or Resin]

The compound or the resin of the present embodiment can be purified by a purification method comprising the following steps.

Specifically, the purification method comprises the steps of: obtaining a solution (A-1) by dissolving the compound represented by the formula (A-1) or the resin comprising a constitutional unit derived from the formula (A-1) in a solvent comprising an organic solvent that does not inadvertently mix with water; and extracting impurities in the compound represented by the above formula (A-1) or the resin by bringing the obtained solution (A-1) into contact with an acidic aqueous solution (a first extraction step).

In the case of using the purification method of the present embodiment, the resin is preferably a resin obtained by reacting the compound represented by the formula (A-1) with a crosslinking compound.

According to the purification method of the present embodiment, the contents of various metals that may be contained as impurities in the compound or the resin having a specific structure described above can be effectively reduced.

Metals contained in the solution (A) containing the compound represented by the formula (A-1) or the resin comprising a constitutional unit derived from the compound represented by the formula (A-1) are transferred to the aqueous phase, then the organic phase and the aqueous phase are separated, and thus the compound represented by the formula (A-1) or the resin comprising a constitutional unit derived from the compound represented by the formula (A-1) having a reduced metal content can be obtained.

The compound represented by the formula (A-1) or the resin comprising a constitutional unit derived from the compound represented by the formula (A-1) used in the purification method of the present embodiment may be alone, or may be a mixture of two or more kinds. Also, the compound represented by the formula (A-1) or the resin comprising a constitutional unit derived from the compound represented by the formula (A-1) may be applied to the production method of the present embodiment together with various surfactants, various crosslinking agents, various acid generators, various stabilizers, and the like.

The "organic solvent that does not inadvertently mix with water" used in the purification method of the present embodiment means an organic solvent that does not uniformly mix with water at any ratio. Such an organic solvent is not particularly limited, but is preferably an organic solvent that is safely applicable to semiconductor manufacturing processes, and specifically it is an organic solvent having a solubility in water at room temperature of less than 30%, and more preferably is an organic solvent having a solubility of less than 20% and particularly preferably less than 10%. The amount of the organic solvent used is preferably 1 to 100 parts by mass based on 100 parts by mass of the compound represented by the formula (A-1) and the resin comprising a constitutional unit derived from the compound represented by the formula (A-1) used.

Specific examples of the organic solvent that does not inadvertently mix with water include, but not limited to, ethers such as diethyl ether and diisopropyl ether; esters such as ethyl acetate, n-butyl acetate, and isoamyl acetate; ketones such as methyl ethyl ketone, methyl isobutyl ketone, ethyl isobutyl ketone, cyclohexanone (CHN), cyclopentanone, 2-heptanone, and 2-pentanone; glycol ether acetates such as ethylene glycol monoethyl ether acetate, ethylene glycol monobutyl ether acetate, propylene glycol monomethyl ether acetate (PGMEA), and propylene glycol monoethyl ether acetate; aliphatic hydrocarbons such as n-hexane and n-heptane; aromatic hydrocarbons such as toluene and xylene; and halogenated hydrocarbons such as methylene chloride and chloroform. Among these, one or more organic solvents selected from the group consisting of toluene, 2-heptanone, cyclohexanone, cyclopentanone, methyl isobutyl ketone, propylene glycol monomethyl ether acetate, ethyl acetate, and the like are preferable, methyl isobutyl ketone, ethyl acetate, cyclohexanone, and propylene glycol monomethyl ether acetate are more preferable, and methyl isobutyl ketone and ethyl acetate are still more preferable. Methyl isobutyl ketone, ethyl acetate, and the like have relatively high saturation solubility for the compound represented by the formula (A) or the resin comprising a constitutional unit derived from the compound represented by the formula (A) and a relatively low boiling point, and it is thus possible to reduce the load in the case of industrially distilling off the solvent and in the step of removing the solvent by drying.

These organic solvents can be each used alone, and can be used as a mixture of two or more kinds.

The "acidic aqueous solution" used in the purification method of the present embodiment is arbitrarily selected from aqueous solutions in which generally known organic compounds or inorganic compounds are dissolved in water. Examples of the acidic aqueous solution include, but not limited to, aqueous mineral acid solutions in which mineral acids such as hydrochloric acid, sulfuric acid, nitric acid, and phosphoric acid are dissolved in water; and aqueous organic acid solutions in which organic acids such as acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid are dissolved in water. These acidic aqueous solutions can be each used alone, and can be also used as a combination of two or more kinds. Among these acidic aqueous solutions, aqueous solutions of one or more mineral acids selected from the group consisting of hydrochloric acid, sulfuric acid, nitric acid, and phosphoric acid, or aqueous solutions of one or more organic acids selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid are preferable, aqueous solutions of sulfuric acid, nitric acid, and carboxylic acids such as acetic acid, oxalic acid, tartaric acid, and citric acid are more preferable, aqueous solutions of sulfuric acid, oxalic acid, tartaric acid, and citric acid are still more preferable, and an aqueous solution of oxalic acid is further preferable. It is considered that polyvalent carboxylic acids such as oxalic acid, tartaric acid, and citric acid coordinate with metal ions and provide a chelating effect, and thus tend to be capable of more effectively removing metals. As for water used herein, it is preferable to use water, the metal content of which is small, such as ion exchanged water, according to the purpose of the purification method of the present embodiment.

The pH of the acidic aqueous solution used in the purification method of the present embodiment is not particularly limited, but it is preferable to regulate the acidity of the aqueous solution in consideration of an influence on the compound represented by the formula (A-1) or the resin comprising a constitutional unit derived from the compound represented by the formula (A-1). Normally, the pH range of the acidic aqueous solution is about 0 to 5, and is preferably about pH 0 to 3.

The amount of the acidic aqueous solution used in the purification method of the present embodiment is not particularly limited, but it is preferable to regulate the amount from the viewpoint of reducing the number of extraction operations for removing metals and from the viewpoint of ensuring operability in consideration of the overall amount of fluid. From the above viewpoints, the amount of the acidic aqueous solution used is preferably 10 to 200% by mass, more preferably 20 to 100% by mass, based on 100% by mass of the solution (A).

In the purification method of the present embodiment, by bringing an acidic aqueous solution as described above into contact with the solution (A) containing one or more selected from the compound represented by the formula (A-1) and the resin comprising a constitutional unit derived from the compound represented by the formula (A-1) and the organic solvent that does not inadvertently mix with water, metals can be extracted from the compound or the resin in the solution (A).

When an organic solvent that advertently mixes with water is contained, there is a tendency that the amount of the compound represented by the formula (A-1) or the resin comprising a constitutional unit derived from the compound represented by the formula (A-1) charged can be increased, also the fluid separability is improved, and purification can be carried out at a high reaction vessel efficiency. The method for adding the organic solvent that advertently mixes with water is not particularly limited. For example, any of a method involving adding it to the organic solvent-containing solution in advance, a method involving adding it to water or the acidic aqueous solution in advance, and a method involving adding it after bringing the organic solvent-containing solution into contact with water or the acidic aqueous solution. Among these, the method involving adding it to the organic solvent-containing solution in advance is preferable in terms of the workability of operations and the ease of managing the amount.

The organic solvent that inadvertently mixes with water used in the purification method of the present embodiment is not particularly limited, but is preferably an organic solvent that is safely applicable to semiconductor manufacturing processes. The amount of the organic solvent used that inadvertently mixes with water is not particularly limited as long as the solution phase and the aqueous phase separate, but is preferably 0.1 to 100 parts by mass, more preferably 0.1 to 50 parts by mass, and further preferably 0.1 to 20 parts by mass based on 100 parts by mass of the compound represented by the formula (A-1) and the resin comprising a constitutional unit derived from the compound represented by the formula (A-1).

Specific examples of the organic solvent used in the purification method of the present embodiment that inadvertently mixes with water include, but not limited to, ethers such as tetrahydrofuran and 1,3-dioxolane; alcohols such as methanol, ethanol, and isopropanol; ketones such as acetone and N-methylpyrrolidone; aliphatic hydrocarbons such as glycol ethers such as ethylene glycol monoethyl ether, ethylene glycol monobutyl ether, propylene glycol monomethyl ether (PGME), and propylene glycol monoethyl ether. Among these, N-methylpyrrolidone, propylene glycol monomethyl ether, and the like are preferable, and N-methylpyrrolidone and propylene glycol monomethyl ether are more preferable. These solvents can be each used alone, and can be used as a mixture of two or more kinds.

In the purification method of the present embodiment, the temperature when the solution (A) and the acidic aqueous solution are brought into contact, i.e., when extraction treatment is carried out, is preferably in the range of 20 to 90° C., and more preferably 30 to 80° C. The extraction operation is not particularly limited, and is carried out, for example, by thoroughly mixing the solution (A) and the acidic aqueous solution by stirring or the like and then leaving the obtained mixed solution to stand still. Thereby, metals contained in the solution (A) containing one or more selected from the compound represented by the formula (A-1) and the resin comprising a constitutional unit derived from the compound represented by the formula (A-1) and the organic solvents are transferred to the aqueous phase. Also, by this operation, the acidity of the solution (A) is lowered, and the degradation of the compound represented by the formula (A-1) and the resin comprising a constitutional unit derived from the compound represented by the formula (A-1) can be suppressed.

By being left to stand still, the mixed solution is separated into an aqueous phase and a solution phase containing one or more selected from the compound represented by the formula (A-1) and the resin comprising a constitutional unit derived from the compound represented by the formula (A-1) and the organic solvents, and thus the solution phase containing one or more selected from the compound represented by the formula (A-1) and the resin comprising a constitutional unit derived from the compound represented by the formula (A-1) and the organic solvents can be recovered by decantation. The time for leaving the mixed solution to stand still is not particularly limited, but it is preferable to regulate the time for leaving the mixed solution to stand still from the viewpoint of attaining good separation of the solution phase containing the organic solvents and the aqueous phase. Normally, the time for leaving the mixed solution to stand still is 1 minute or longer, preferably 10 minutes or longer, and more preferably 30 minutes or longer. While the extraction treatment may be carried out once, it is effective to repeat mixing, leaving-to-stand-still, and separating operations multiple times.

It is preferable that the purification method of the present embodiment includes the step of extracting impurities in the compound or the resin by further bringing the solution phase containing the compound or the resin into contact with water after the first extraction step (the second extraction step).

Specifically, for example, it is preferable that after the extraction treatment is carried out using an acidic aqueous solution, the solution phase that is extracted and recovered from the aqueous solution and that contains one or more selected from the compound represented by the formula (A-1) and the resin comprising a constitutional unit derived from the compound represented by the formula (A-1) and the organic solvents is further subjected to extraction treatment with water. The extraction treatment with water is not particularly limited, and can be carried out, for example, by thoroughly mixing the solution phase and water by stirring or the like and then leaving the obtained mixed solution to stand still. The mixed solution after being left to stand still is separated into an aqueous phase and a solution phase containing one or more selected from the compound represented by the formula (A-1) and the resin comprising a constitutional unit derived from the compound represented by the formula (A-1) and the organic solvents, and thus the solution phase containing one or more selected from the compound represented by the formula (A-1) and the resin comprising a constitutional unit derived from the compound represented by the formula (A-1) and the organic solvents can be recovered by decantation.

Water used herein is preferably water, the metal content of which is small, such as ion exchanged water, according to the purpose of the present embodiment. While the extraction treatment may be carried out once, it is effective to repeat mixing, leaving-to-stand-still, and separating operations multiple times. The proportions of both used in the extraction treatment and temperature, time, and other conditions are not particularly limited, and may be the same as those of the previous contact treatment with the acidic aqueous solution.

Water that is possibly present in the thus-obtained solution containing one or more selected from the compound represented by the formula (A-1) and the resin comprising a constitutional unit derived from the compound represented by the formula (A-1) and the organic solvents can be easily removed by performing vacuum distillation or a like operation. Also, if required, the concentration of the compound represented by the formula (A-1) and the resin comprising a constitutional unit derived from the compound represented by the formula (A-1) can be regulated to be any concentration by adding an organic solvent to the solution.

The method for isolating one or more selected from the compound represented by the above formula (A-1) and the resin comprising a constitutional unit derived from the compound represented by the formula (A-1) from the obtained solution containing one or more selected from the compound represented by the formula (A-1) and the resin comprising a constitutional unit derived from the compound represented by the formula (A-1) and the organic solvents is not particularly limited, and publicly known methods can be carried out, such as reduced-pressure removal, separation by reprecipitation, and a combination thereof. Publicly known treatments such as concentration operation, filtration operation, centrifugation operation, and drying operation can be carried out if required.

(Physical Properties and the Like of Material Composition for Lithography)

The material for lithography of the present embodiment can be used for the purpose of preparing resists as mentioned above, and can form an amorphous film by a publicly known method such as spin coating. Depending on the kind of a developing solution to be used, a positive type resist pattern and a negative type resist pattern can be individually prepared. Hereinafter, use of a material composition for lithography comprising the material for lithography of the present embodiment for the purpose of preparing resists (as a resist composition) will be described.

In the case of using the material composition for lithography according to the present embodiment to form a positive type resist pattern, the dissolution rate of the amorphous film formed by spin coating with the material composition for lithography of the present embodiment in a developing solution at 23° C. is preferably 5 angstrom/sec or less, more preferably 0.05 to 5 angstrom/sec, and further preferably 0.0005 to 5 angstrom/sec. When the dissolution rate is 5 angstrom/sec or less, a resist insoluble in a developing solution can be prepared. When the amorphous film has a dissolution rate of 0.0005 angstrom/sec or more, the resolution may improve. It is presumed that this is because due to the change in the solubility before and after exposure of the compound represented by the formula (A) and the resin comprising a constitutional unit derived from the compound represented by the formula (A), contrast at the interface between the exposed portion being dissolved in a developing solution and the unexposed portion not being dissolved in a developing solution is increased. Also, there are effects of reducing line edge roughness and defects.

In the case of using the material composition for lithography according to the present embodiment to form a negative type resist pattern, the dissolution rate of the amorphous film formed by spin coating with the material composition for lithography of the present embodiment in a developing solution at 23° C. is preferably 10 angstrom/sec or more. When the dissolution rate is 10 angstrom/sec or more, the amorphous film more easily dissolves in a developing solution, and is more suitable for a resist. When the amorphous film has a dissolution rate of 10 angstrom/sec or more, the resolution may improve. It is presumed that this is because the micro surface portion of the compound represented by the formula (A) and the resin comprising a constitutional unit derived from the compound represented by the formula (A) dissolves, and line edge roughness is reduced. Also, there are effects of reducing defects.

The dissolution rate can be determined by immersing the amorphous film in a developing solution for a predetermined period of time at 23° C. and then measuring the film thickness before and after immersion by a publicly known method such as visual, ellipsometric, or QCM method.

In the case of using the material composition for lithography of the present embodiment to form a positive type resist pattern, the dissolution rate of the portion exposed by radiation such as KrF excimer laser, extreme ultraviolet, electron beam or X-ray, of the amorphous film formed by spin coating with the material composition for lithography of the present embodiment, in a developing solution at 23° C. is preferably 10 angstrom/sec or more. When the dissolution rate is 10 angstrom/sec or more, the above portion more easily dissolves in a developing solution, and the amorphous film is more suitable for a resist. When the above portion has a dissolution rate of 10 angstrom/sec or more, the resolution may improve. It is presumed that this is because the micro surface portion of the compound represented by the formula (A-1) and the resin comprising a constitutional unit derived from the compound represented by the formula (A-1) dissolves, and line edge roughness is reduced. Also, there are effects of reducing defects.

In the case of using the material composition for lithography of the present embodiment to form a negative type resist pattern, the dissolution rate of the portion exposed by radiation such as KrF excimer laser, extreme ultraviolet, electron beam or X-ray, of the amorphous film formed by spin coating with the material composition for lithography of the present embodiment, in a developing solution at 23° C. is preferably 5 angstrom/sec or less, more preferably 0.05 to 5 angstrom/sec, and further preferably 0.0005 to 5 angstrom/sec. When the dissolution rate is 5 angstrom/sec or less, a resist insoluble in a developing solution can be prepared. When the above portion has a dissolution rate of 0.0005 angstrom/sec or more, the resolution may improve. It is presumed that this is because due to the change in the solubility before and after exposure of the compound represented by the formula (A-1) and the resin comprising a constitutional unit derived from the compound represented by the formula (A-1), contrast at the interface between the unexposed portion being dissolved in a developing solution and the exposed portion not being dissolved in a developing solution is increased. Also, there are effects of reducing line edge roughness and defects.

(Other Components of Material Composition for Lithography)

The material composition for lithography of the present embodiment contains at least any one of the compound represented by the formula (A-1) and the resin comprising a constitutional unit derived from the compound represented by the formula (A-1) as a solid component. The material composition for lithography of the present embodiment may contain both the compound represented by the formula (A-1) and the resin comprising a constitutional unit derived from the compound represented by the formula (A-1).

It is preferable that the material composition for lithography of the present embodiment further contains a solvent other than the compound represented by the formula (A-1) and the resin comprising a constitutional unit derived from the compound represented by the formula (A-1).

Examples of the solvent used in the material composition for lithography of the present embodiment can include, but not particularly limited to, ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate, propylene glycol monoethyl ether acetate (PGMEA), propylene glycol mono-n-propyl ether acetate, and propylene glycol mono-n-butyl ether acetate; propylene glycol monoalkyl ethers such as propylene glycol monomethyl ether (PGME) and propylene glycol monoethyl ether; ester lactates such as methyl lactate, ethyl lactate, n-propyl lactate, n-butyl lactate, and n-amyl lactate; aliphatic carboxylic acid esters such as methyl acetate, ethyl acetate, n-propyl acetate, n-butyl acetate, n-amyl acetate, n-hexyl acetate, methyl propionate, and ethyl propionate; other esters such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutylacetate, 3-methyl-3-methoxybutylacetate, butyl 3-methoxy-3-methylpropionate, butyl 3-methoxy-3-methylbutyrate, methyl acetoacetate, methyl pyruvate, and ethyl pyruvate; aromatic hydrocarbons such as toluene and xylene; ketones such as methyl ethyl ketone, 2-heptanone, 3-heptanone, 4-heptanone, cyclopentanone (CPN), and cyclohexanone (CHN); amides such as N,N-dimethylformamide, N-methylacetamide, N,N-dimethylacetamide, and N-methylpyrrolidone; and lactones such as γ-lactone. These solvents can be used alone or in combination of two or more kinds.

The solvent used in the material composition for lithography of the present embodiment is preferably a safe solvent, more preferably at least one selected from PGMEA, PGME, CHN, CPN, 2-heptanone, anisole, butyl acetate, ethyl propionate, and ethyl lactate, and still more preferably at least one selected from PGMEA, PGME, and CHN.

In the material composition for lithography of the present embodiment, the relationship between the amount of the solid component and the amount of the solvent is not particularly limited, but preferably the solid component is 1 to 80% by mass and the solvent is 20 to 99% by mass, more preferably the solid component is 1 to 50% by mass and the solvent is 50 to 99% by mass, still more preferably the solid component is 2 to 40% by mass and the solvent is 60 to 98% by mass, and particularly preferably the solid component is 2 to 10% by mass and the solvent is 90 to 98% by mass, based on 100% by mass of the total mass of the amount of the solid component and the solvent.

The material composition for lithography of the present embodiment may contain at least one selected from the group consisting of an acid generating agent (C), an acid crosslinking agent (G), an acid diffusion controlling agent (E), and a further component (F), as other solid components.

In the material composition for lithography of the present embodiment, the content of the compound represented by the formula (A-1) and the resin comprising a constitutional unit derived from the compound represented by the formula (A-1) is not particularly limited, but is preferably 50 to 99.4% by mass of the total mass of the solid components (summation of the compound represented by the formula (A-1) and the resin comprising a constitutional unit derived from the compound represented by the formula (A-1), and optionally used solid components such as acid generating agent (C), acid crosslinking agent (G), acid diffusion controlling agent (E), and further component (F), hereinafter the same), more preferably 55 to 90% by mass, still more preferably 60 to 80% by mass, and particularly preferably 60 to 70% by mass. In the case of the above content, resolution is further improved, and line edge roughness (LER) is further decreased.

When both the compound represented by the formula (A-1) and the resin comprising a constitutional unit derived from the compound represented by the formula (A-1) are contained, the content refers to the total amount of the compound represented by the formula (A-1) and the resin comprising a constitutional unit derived from the compound represented by the formula (A-1).

(Acid Generating Agent (C))

The material composition for lithography of the present embodiment preferably contains one or more acid generating agents (C) generating an acid directly or indirectly by irradiation of any radiation selected from visible light, ultraviolet, excimer laser, electron beam, extreme ultraviolet (EUV), X-ray, and ion beam.

In this case, in the material composition for lithography of the present embodiment, the content of the acid generating agent (C) is preferably 0.001 to 49% by mass of the total mass of the solid components, more preferably 1 to 40% by mass, still more preferably 3 to 30% by mass, and particularly preferably 10 to 25% by mass. By using the acid generating agent (C) within the above content range, a pattern profile with even higher sensitivity and even lower edge roughness is obtained.

Concerning the material composition for lithography of the present embodiment, the acid generation method is not particularly limited as long as an acid is generated in the system. By using excimer laser instead of ultraviolet such as g-ray and i-ray, finer processing is possible, and also by using electron beam, extreme ultraviolet, X-ray or ion beam as a high energy ray, further finer processing is possible.

The acid generating agent (C) is not particularly limited, and is preferably at least one kind selected from the group consisting of compounds represented by the following formulae (8-1) to (8-8):

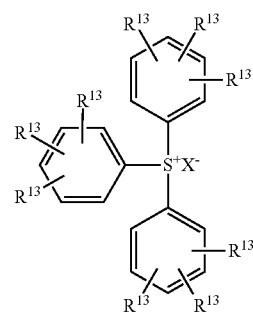

Formula (8-1)

(In the formula (8-1), $R^{13}$ may be each the same or different, and are each independently a hydrogen atom, a linear, branched or cyclic alkyl group, a linear, branched or cyclic alkoxy group, a hydroxyl group, or a halogen atom, X⁻ is an alkyl group, an aryl group, a sulfonic acid ion having a halogen substituted alkyl group or a halogen substituted aryl group, or a halide ion.)

The compound represented by the above formula (8-1) is preferably at least one kind selected from the group consisting of triphenylsulfonium trifluoromethanesulfonate, triphenylsulfonium nonafluoro-n-butanesulfonate, diphenyltolylsulfonium nonafluoro-n-butanesulfonate, triphenylsulfonium perfluoro-n-octanesulfonate, diphenyl-4-methylphenylsulfonium trifluoromethanesulfonate, di-2,4,6-trimethylphenylsulfonium trifluoromethanesulfonate, diphenyl-4-t-butoxyphenylsulfonium trifluoromethanesulfonate, diphenyl-4-t-butoxyphenylsulfonium nonafluoro-n-butanesulfonate, diphenyl-4-hydroxyphenylsulfonium trifluoromethanesulfonate, bis(4-fluorophenyl)-4-hydroxyphenylsulfonium trifluoromethanesulfonate, diphenyl-4-hydroxyphenylsulfonium nonafluoro-n-butanesulfonate, bis(4-hydroxyphenyl)-phenylsulfonium trifluoromethanesulfonate, tri(4-methoxyphenyl)sulfonium trifluoromethanesulfonate, tri(4-fluorophenyl)sulfonium trifluoromethanesulfonate, triphenylsulfonium p-toluenesulfonate, triphenylsulfonium benzenesulfonate, diphenyl-2,4,6-trimethylphenyl-p-toluenesulfonate, diphenyl-2,4,6-trimethylphenylsulfonium-2-trifluoromethylbenzenesulfonate, diphenyl-2,4,6-trimethylphenylsulfonium-4-trifluoromethylbenzenesulfonate, diphenyl-2,4,6-trimethylphenylsulfonium-2,4-difluorobenzenesulfonate, diphenyl-2,4,6-trimethylphenylsulfonium hexafluorobenzenesulfonate, diphenylnaphthylsulfonium trifluoromethanesulfonate, diphenyl-4-hydroxyphenylsulfonium-p-toluenesulfonate, triphenylsulfonium 10-camphorsulfonate, diphenyl-4-hydroxyphenylsulfonium 10-camphorsulfonate, and cyclo(1,3-perfluoropropanedisulfone)imidate.

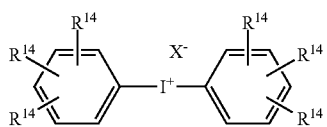

Formula (8-2)

(In the formula (8-2), $R^{14}$ may be each the same or different, and each independently represents a hydrogen atom, a linear, branched or cyclic alkyl group, a linear, branched or cyclic alkoxy group, a hydroxyl group, or a halogen atom. X⁻ is the same as above.)

The compound represented by the above formula (8-2) is preferably at least one kind selected from the group consisting of bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium p-toluenesulfonate, bis(4-t-butylphenyl)iodonium benzenesulfonate, bis(4-t-butylphenyl)iodonium-2-trifluoromethylbenzenesulfonate, bis(4-t-butylphenyl)iodonium-4-trifluoromethylbenzenesulfonate, bis(4-t-butylphenyl)iodonium-2,4-difluorobenzenesulfonate, bis(4-t-butylphenyl)iodonium hexafluorobenzenesulfonate, bis(4-t-butylphenyl)iodonium 10-camphorsulfonate, diphenyliodonium trifluoromethanesulfonate, diphenyliodonium nonafluoro-n-butanesulfonate, diphenyliodonium perfluoro-n-octanesulfonate, diphenyliodonium p-toluenesulfonate, diphenyliodonium benzenesulfonate, diphenyliodonium 10-camphorsulfonate, diphenyliodonium-2-trifluoromethylbenzenesulfonate, diphenyliodonium-4-trifluoromethylbenzenesulfonate, diphenyliodonium-2,4-difluorobenzenesulfonate, diphenyliodonium hexafluorobenzenesulfonate, di(4-trifluoromethylphenyl)iodonium trifluoromethanesulfonate, di(4-trifluoromethylphenyl)iodonium nonafluoro-n-butanesulfonate, di(4-trifluoromethylphenyl)iodonium perfluoro-n-octanesulfonate, di(4-trifluoromethylphenyl)iodonium p-toluenesulfonate, di(4-trifluoromethylphenyl)iodonium benzenesulfonate, and di(4-trifluoromethylphenyl)iodonium 10-camphorsulfonate.

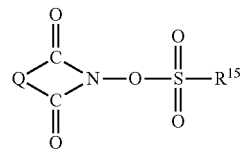

Formula (8-3)

(In the formula (8-3), Q is an alkylene group, an arylene group, or an alkoxylene group, and $R^{15}$ is an alkyl group, an aryl group, a halogen substituted alkyl group, or a halogen substituted aryl group.)

The compound represented by the above formula (8-3) is preferably at least one kind selected from the group consisting of N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hept-5-en-2,3-dicarboxyimide, N-(trifluoromethylsulfonyloxy)naphthylimide, N-(10-camphorsulfonyloxy)succinimide, N-(10-camphorsulfonyloxy)phthalimide, N-(10-camphorsulfonyloxy)diphenylmaleimide, N-(10-camphorsulfonyloxy)bicyclo[2.2.1]hept-5-en-2,3-dicarboxyimide, N-(10-camphorsulfonyloxy)naphthylimide, N-(n-octanesulfonyloxy)bicyclo[2.2.1]hept-5-en-2,3-dicarboxyimide, N-(n-octanesulfonyloxy)naphthylimide, N-(p-toluenesulfonyloxy)bicyclo[2.2.1]hept-5-en-2,3-dicarboxyimide, N-(p-toluenesulfonyloxy)naphthylimide, N-(2-trifluoromethylbenzenesulfonyloxy)bicyclo[2.2.1]hept-5-en-2,3-dicarboxyimide, N-(2-trifluoromethylbenzenesulfonyloxy)naphthylimide, N-(4-trifluoromethylbenzenesulfonyloxy)bicyclo[2.2.1]hept-5-en-2,3-dicarboxyimide, N-(4-trifluoromethylbenzenesulfonyloxy)naphthylimide, N-(perfluorobenzenesulfonyloxy)bicyclo[2.2.1]hept-5-en-2,3-dicarboxyimide, N-(perfluorobenzenesulfonyloxy)naphthylimide, N-(1-naphthalenesulfonyloxy)bicyclo[2.2.1]hept-5-en-2,3-dicarboxyimide, N-(1-naphthalenesulfonyloxy)naphthylimide, N-(nonafluoro-n-butanesulfonyloxy)bicyclo[2.2.1]hept-5-en-2,3-dicarboxyimide, N-(nonafluoro-n-butanesulfonyloxy)naphthylimide, N-(perfluoro-n-octanesulfonyloxy)bicyclo[2.2.1]hept-5-en-2,3-dicarboxyimide, and N-(perfluoro-n-octanesulfonyloxy)naphthylimide.

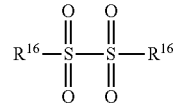

Formula (8-4)

(In the formula (8-4), $R^{16}$ may be each the same or different, and are each independently an optionally substituted linear, branched or cyclic alkyl group, an optionally substituted aryl group, an optionally substituted heteroaryl group, or an optionally substituted aralkyl group.)

The compound represented by the above formula (8-4) is preferably at least one kind selected from the group consisting of diphenyldisulfone, di(4-methylphenyl)disulfone, dinaphthyldisulfone, di(4-tert-butylphenyl)disulfone, di(4-hydroxyphenyl)disulfone, di(3-hydroxynaphthyl)disulfone, di(4-fluorophenyl)disulfone, di(2-fluorophenyl)disulfone, and di(4-trifluoromethylphenyl)disulfone.

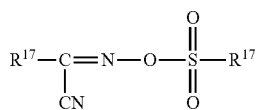

(In the formula (8-5), $R^{17}$ may be the same or different, and are each independently an optionally substituted linear, branched or cyclic alkyl group, an optionally substituted aryl group, an optionally substituted heteroaryl group, or an optionally substituted aralkyl group.)

The compound represented by the above formula (8-5) is preferably at least one kind selected from the group consisting of α-(methylsulfonyloxyimino)-phenylacetonitrile, α-(methylsulfonyloxyimino)-4-methoxyphenylacetonitrile, α-(trifluoromethylsulfonyloxyimino)-phenylacetonitrile, α-(trifluoromethylsulfonyloxyimino)-4-methoxyphenylacetonitrile, α-(ethylsulfonyloxyimino)-4-methoxyphenylacetonitrile, α-(propylsulfonyloxyimino)-4-methylphenylacetonitrile, and α-(methylsulfonyloxyimino)-4-bromophenylacetonitrile.

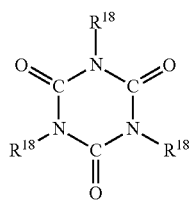

Formula (8-6)

In the formula (8-6), $R^{18}$ may be each the same or different, and are each independently a halogenated alkyl group having one or more chlorine atoms and one or more bromine atoms. The number of carbons in the halogenated alkyl group is preferably 1 to 5.

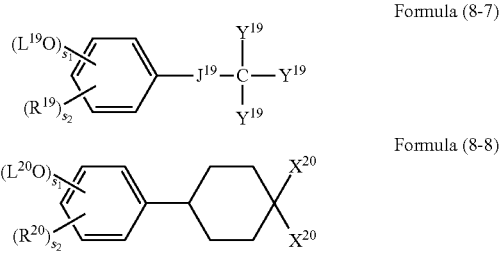

In the formulae (8-7) and (8-8), $R^{19}$ and $R^{20}$ are each independently an alkyl group of 1 to 3 carbon atoms such as a methyl group, an ethyl group, an n-propyl group, and an isopropyl group; a cycloalkyl group such as a cyclopentyl group and a cyclohexyl group; an alkoxyl group of 1 to 3 carbon atoms such as a methoxy group, an ethoxy group, and a propoxy group; or an aryl group such as a phenyl group, a toluoyl group, and a naphthyl group, and preferably an aryl group of 6 to 10 carbon atom. $L^{19}$ and $L^{20}$ are each independently an organic group having a 1,2-naphthoquinonediazide group. Specifically, preferable examples of the organic group having a 1,2-naphthoquinonediazide group include a 1,2-quinonediazidesulfonyl group such as a 1,2-naphthoquinonediazide-4-sulfonyl group, a 1,2-naphthoquinonediazide-5-sulfonyl group, and a 1,2-naphthoquinonediazide-6-sulfonyl group. Particularly, a 1,2-naphthoquinonediazide-4-sulfonyl group and a 1,2-naphthoquinonediazide-5-sulfonyl group are preferable. Each $s_1$ is independently an integer of 1 to 3; each $s_2$ is independently an integer of 0 to 4; and $1 \leq s_1 + s_2 \leq 5$. $J^{19}$ is a single bond, a polymethylene group of 1 to 4 carbon atoms, a cycloalkylene group, a phenylene group, a group represented by the following formula (8-7-1), a carbonyl group, an ester group, an amide group, or an ether group. $Y^{19}$ is a hydrogen atom, an alkyl group, or an aryl group, and $X^{20}$ are each independently a group represented by the following formula (8-8-1):

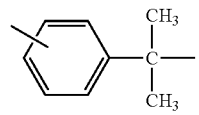

Formula (8-7-1)

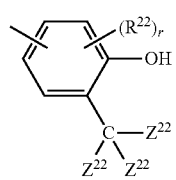

Formula (8-8-1)

(In the above formula (8-8-1), $Z^{22}$ are each independently an alkyl group, a cycloalkyl group, or an aryl group; $R^{22}$ is an alkyl group, a cycloalkyl group, or an alkoxyl group; and r is an integer of 0 to 3.)

Examples of the other acid generating agent include bissulfonyldiazomethanes such as bis(p-toluenesulfonyl)diazomethane, bis(2,4-dimethylphenylsulfonyl)diazomethane, bis(tert-butylsulfonyl)diazomethane, bis(n-butylsulfonyl)diazomethane, bis(isobutylsulfonyl)diazomethane, bis(isopropylsulfonyl)diazomethane, bis(n-propylsulfonyl)diazomethane, bis(cyclohexylsulfonyl)diazomethane, bis(isopropylsulfonyl)diazomethane, 1,3-bis(cyclohexylsulfonylazomethylsulfonyl)propane, 1,4-bis(phenylsulfonylazomethylsulfonyl)butane, 1,6-bis(phenylsulfonylazomethylsulfonyl)hexane, and 1,10-bis(cyclohexylsulfonylazomethylsulfonyl)decane; and halogen-containing triazine derivatives such as 2-(4-methoxyphenyl)-4,6-(bistrichloromethyl)-1,3,5-triazine, 2-(4-methoxynaphthyl)-4,6-(bistrichloromethyl)-1,3,5-triazine, tris(2,3-dibromopropyl)-1,3,5-triazine, and tris(2,3-dibromopropyl)isocyanurate.

Among the acid generating agents, the acid generating agent (C) used in the material composition for lithography of the present embodiment is preferably an acid generating agent having an aromatic ring, and more preferably an acid generating agent represented by the formula (8-1) or (8-2). An acid generating agent having a sulfonate ion wherein $X^-$ of the formula (8-1) or (8-2) has an aryl group or a halogen-substituted aryl group is further preferable; an acid generating agent having a sulfonate ion wherein X⁻ of the formula (8-1) or (8-2) has an aryl group is particularly preferable; and diphenyltrimethylphenylsulfonium p-toluenesulfonate, triphenylsulfonium p-toluenesulfonate, triphenylsulfonium trifluoromethanesulfonate, and triphenylsulfonium nonafluoromethanesulfonate are particularly preferable.

By using the acid generating agent, line edge roughness can be reduced.

The acid generating agent (C) can be used alone or in combination of two or more kinds.

(Acid Crosslinking Agent (G))

The material composition for lithography of the present embodiment preferably contains one or more acid crosslinking agents (G), when used as a negative type resist material or when used as an additive agent for enhancing the strength of a pattern even for a positive type resist material. The acid crosslinking agent (G) is a compound capable of intramolecular or intermolecular crosslinking the compound represented by the above formula (A-1) in the presence of the acid generated from the acid generating agent (C). Examples of such an acid crosslinking agent (G) include, but not particularly limited to, a compound having one or more groups (hereinafter, referred to as "crosslinkable group") capable of crosslinking the compound represented by the above formula (A-1).

Specific examples of such a crosslinkable group are not particularly limited, and examples include (i) a hydroxyalkyl group or a group derived therefrom, such as a hydroxy (alkyl of 1 to 6 carbon atoms) group, an alkoxy of 1 to 6 carbon atoms (alkyl of 1 to 6 carbon atoms) group, and an acetoxy (alkyl of 1 to 6 carbon atoms) group; (ii) a carbonyl group or a group derived therefrom, such as a formyl group and a carboxy (alkyl of 1 to 6 carbon atoms) group; (iii) a nitrogenous group-containing group such as a dimethylaminomethyl group, a diethylaminomethyl group, a dimethylolaminomethyl group, a diethylolaminomethyl group, and a morpholinomethyl group; (iv) a glycidyl group-containing group such as a glycidyl ether group, a glycidyl ester group, and a glycidylamino group; (v) a group derived from an aromatic group such as an allyloxy of 1 to 6 carbon atoms (alkyl of 1 to 6 carbon atoms) group and an aralkyloxy of 1 to 6 carbon atoms (alkyl of 1 to 6 carbon atoms) group such as a benzyloxymethyl group and a benzoyloxymethyl group; and (vi) a polymerizable multiple bond-containing group such as a vinyl group and a isopropenyl group. As the crosslinkable group of the acid crosslinking agent (G), a hydroxyalkyl group and an alkoxyalkyl group or the like are preferable, and an alkoxymethyl group is particularly preferable.

Examples of the acid crosslinking agent (G) having the above crosslinkable group include, but not particularly limited to, (i) a methylol group-containing compound such as a methylol group-containing melamine compound, a methylol group-containing benzoguanamine compound, a methylol group-containing urea compound, a methylol group-containing glycoluryl compound, and a methylol group-containing phenolic compound; (ii) an alkoxyalkyl group-containing compound such as an alkoxyalkyl group-containing melamine compound, an alkoxyalkyl group-containing benzoguanamine compound, an alkoxyalkyl group-containing urea compound, an alkoxyalkyl group-containing glycoluryl compound, and an alkoxyalkyl group-containing phenolic compound; (iii) a carboxymethyl group-containing compound such as a carboxymethyl group-containing melamine compound, a carboxymethyl group-containing benzoguanamine compound, a carboxymethyl group-containing urea compound, a carboxymethyl group-containing glycoluryl compound, and a carboxymethyl group-containing phenolic compound; (iv) an epoxy compound such as a bisphenol A based epoxy compound, a bisphenol F based epoxy compound, a bisphenol S based epoxy compound, a novolac resin based epoxy compound, a resol resin based epoxy compound, and a poly(hydroxystyrene) based epoxy compound.

As the acid crosslinking agent (G), a compound having a phenolic hydroxyl group, and a compound and resin where the above crosslinkable group is introduced into an acid functional group in an alkali soluble resin to impart crosslinkability can be further used. The introduction rate of the crosslinkable group in that case is not particularly limited, and is adjusted to be, for example, 5 to 100 mol %, preferably 10 to 60 mol %, and more preferably 15 to 40 mol % based on the total acid functional groups in the compound having a phenolic hydroxy group, and the alkali soluble resin. Within the above range, the crosslinking reaction occurs sufficiently, and a decrease in the film remaining rate, and swelling phenomena and meandering or the like of a pattern are avoided, which is preferable.

In the material composition for lithography of the present embodiment, as the acid crosslinking agent (G), an alkoxyalkylated urea compound or resin thereof, or an alkoxyalkylated glycoluryl compound or resin thereof is preferable. Particularly preferable examples of the acid crosslinking agent (G) include compounds represented by the following formulae (11-1) to (11-3) and an alkoxymethylated melamine compound (acid crosslinking agent (G1)).

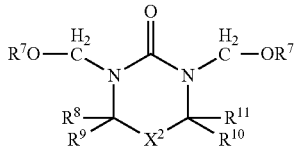

Formula (11-1)

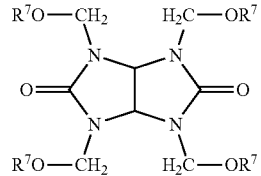

Formula (11-2)

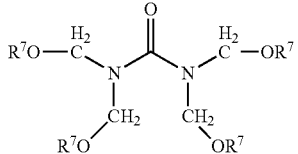

Formula (11-3)

(In the above formulae (11-1) to (11-3), $R^7$ each independently represents a hydrogen atom, an alkyl group, or an acyl group; $R^8$ to $R^{11}$ each independently represents a hydrogen atom, a hydroxyl group, an alkyl group, or an alkoxyl group; and $X^2$ represents a single bond, a methylene group, or an oxygen atom.)

The alkyl group represented by $R^7$ is not particularly limited, and is preferably of 1 to 6 carbon atoms, and more preferably of 1 to 3 carbon atoms. Examples thereof include a methyl group, an ethyl group, and a propyl group. The acyl group represented by $R^7$ is not particularly limited, and is preferably of 2 to 6 carbon atoms, and more preferably of 2 to 4 carbon atoms. Examples thereof include an acetyl group and a propionyl group. The alkyl group represented by $R^8$ to $R^{11}$ is not particularly limited, and is preferably of 1 to 6 carbon atoms, and more preferably of 1 to 3 carbon atoms. Examples thereof include a methyl group, an ethyl group, and a propyl group. The alkoxy group represented by $R^8$ to $R^{11}$ is not particularly limited, and is preferably of 1 to 6 carbon atoms, and more preferably of 1 to 3 carbon atoms. Examples thereof include a methoxy group, an ethoxy group, and a propoxy group. $X^2$ is preferably a single bond or a methylene group. $R^7$ to $R^{11}$ and $X^2$ may be substituted with an alkyl group such as a methyl group and an ethyl group, an alkoxy group such as a methoxy group and an ethoxy group, a hydroxyl group, and a halogen atom or the like. A plurality of $R^7$ and $R^8$ to $R^{11}$ may be each the same or different.

Specific examples of the compound represented by the formula (11-1) include compounds represented below.

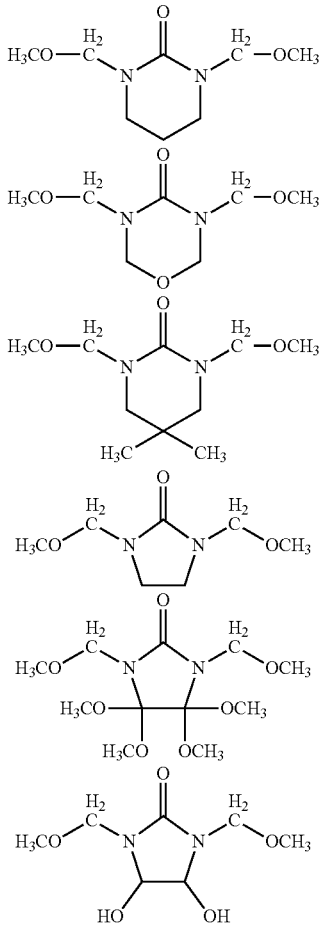

The compound represented by the formula (11-2) is not particularly limited, and specific examples include N,N,N,N-tetra(methoxymethyl)glycoluryl, N,N,N,N-tetra(ethoxymethyl)glycoluryl, N,N,N,N-tetra(n-propoxymethyl)glycoluryl, N,N,N,N-tetra(isopropoxymethyl)glycoluryl, N,N,N,N-tetra(n-butoxymethyl)glycoluryl, and N,N,N,N-tetra(t-butoxymethyl)glycoluryl. Among these, N,N,N,N-tetra(methoxymethyl)glycoluryl is particularly preferable.

The compound represented by the formula (11-3) is not particularly limited, and specific examples include compounds represented below.

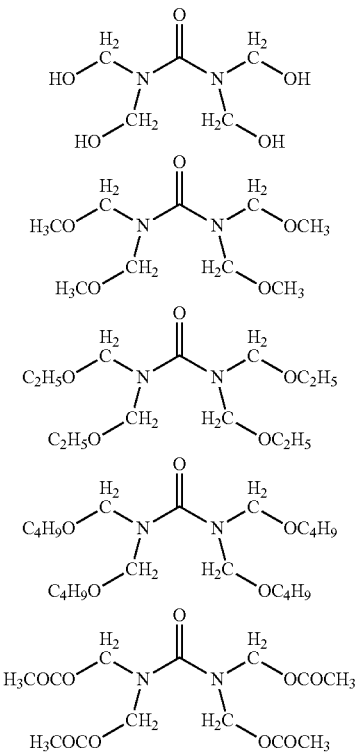

The alkoxymethylated melamine compound is not particularly limited, and specific examples include N,N,N,N,N,N-hexa(methoxymethyl)melamine, N,N,N,N,N,N-hexa(ethoxymethyl)melamine, N,N,N,N,N,N-hexa(n-propoxymethyl)melamine, N,N,N,N,N,N-hexa(isopropoxymethyl)melamine, N,N,N,N,N,N-hexa(n-butoxymethyl)melamine, and N,N,N,N,N,N-hexa(t-butoxymethyl)melamine. Among these, N,N,N,N,N,N-hexa(methoxymethyl)melamine is particularly preferable.

The above acid crosslinking agent (G1) can be obtained by, for example, conducting a condensation reaction of a urea compound or a glycoluryl compound with formalin to introduce an methylol group, etherifying the product with lower alcohols such as methyl alcohol, ethyl alcohol, propyl alcohol, and butyl alcohol, and then cooling the reaction solution to collect a precipitated compound or resin thereof. The above acid crosslinking agent (G1) can be obtained as a commercially available product such as CYMEL (trade name, manufactured by MT AquaPolymer) and NIKALAC (manufactured by Sanwa Chemical).

Other particularly preferable examples of the acid crosslinking agent (G) include a phenol derivative having 1 to 6 benzene rings within a molecule and two or more hydroxyalkyl groups and/or alkoxyalkyl groups within the entire molecule, the hydroxyalkyl groups and/or alkoxyalkyl groups being bonded to any of the above benzene rings (acid crosslinking agent (G2)). Preferable examples thereof include a phenol derivative having a molecular weight of 1500 or less, 1 to 6 benzene rings and a total of two or more hydroxyalkyl groups and/or alkoxyalkyl groups within a molecule, the hydroxyalkyl groups and/or alkoxyalkyl groups being bonded to any one of the above benzene rings, or a plurality of benzene rings.

The hydroxyalkyl group bonded to a benzene ring is not particularly limited, and is the one of 1 to 6 carbon atoms such as a hydroxymethyl group, a 2-hydroxyethyl group, and a 2-hydroxy-1-propyl group is preferable. As the alkoxyalkyl group bonded to a benzene ring, the one of 2 to 6 carbon atoms is preferable. Specifically, a methoxymethyl group, an ethoxymethyl group, an n-propoxymethyl group, an isopropoxymethyl group, an n-butoxymethyl group, an isobutoxymethyl group, a sec-butoxymethyl group, a t-butoxymethyl group, a 2-methoxyethyl group, or a 2-methoxy-1-propyl group is preferable.

Among these phenol derivatives, particularly preferable ones are shown below:

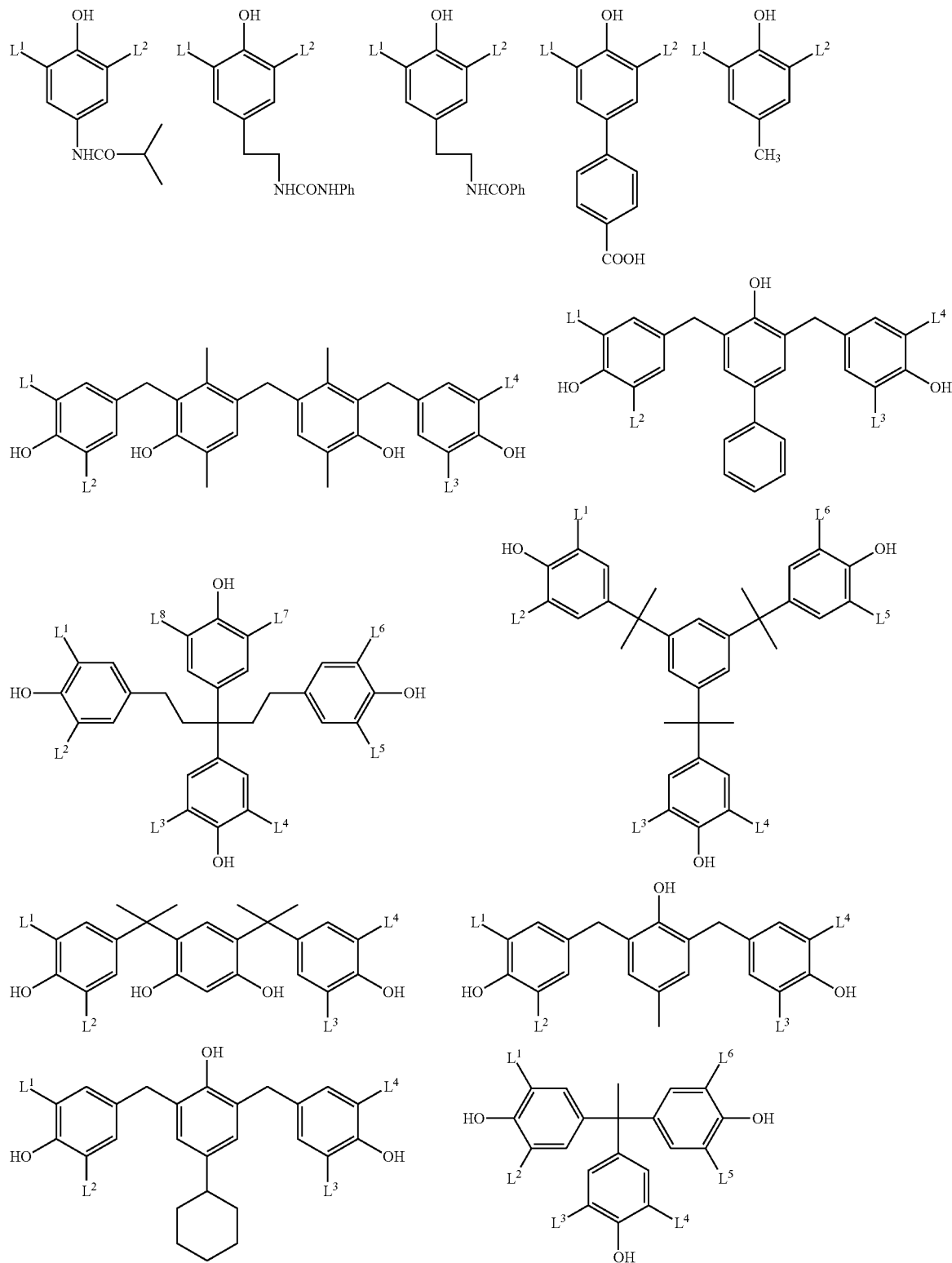

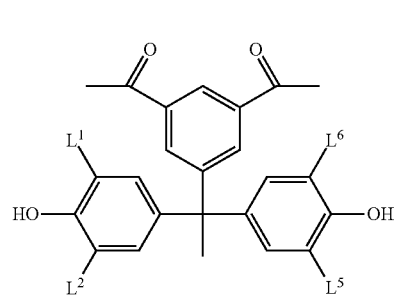
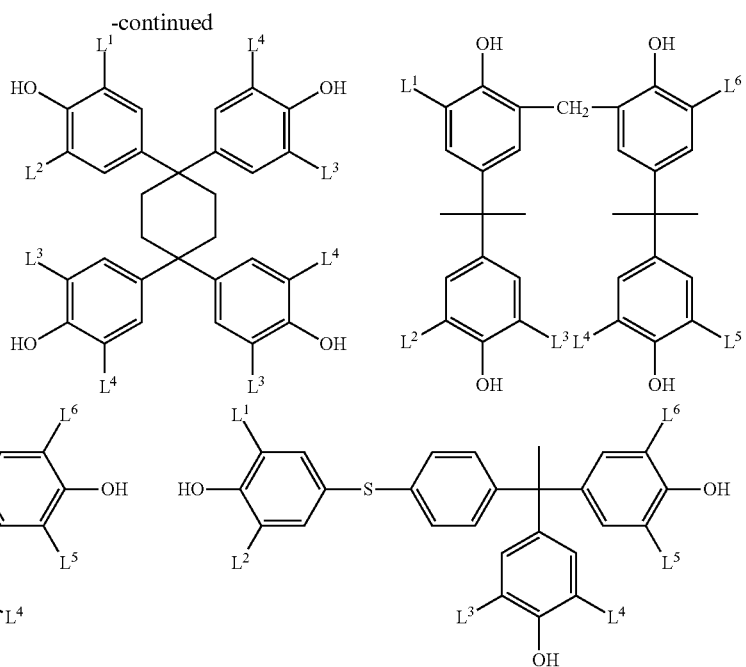
-continued
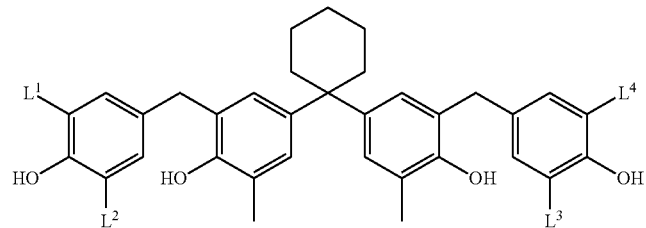
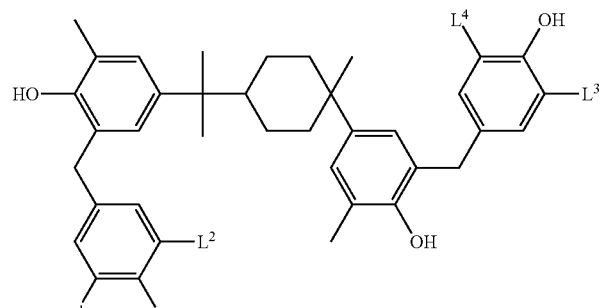
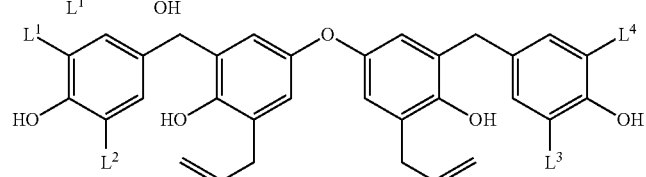
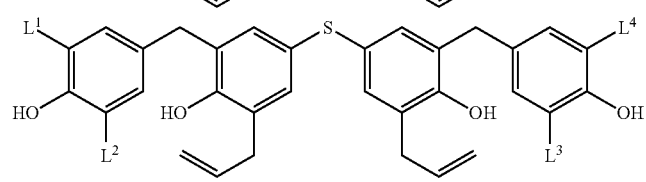
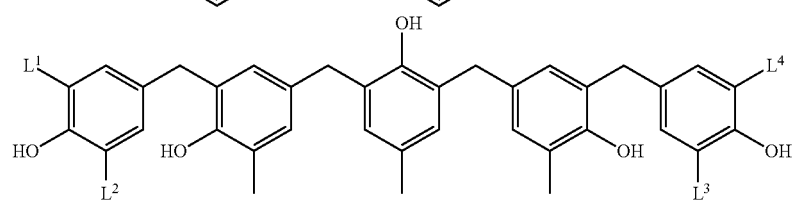

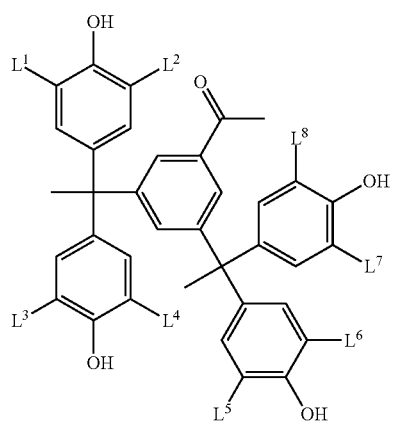
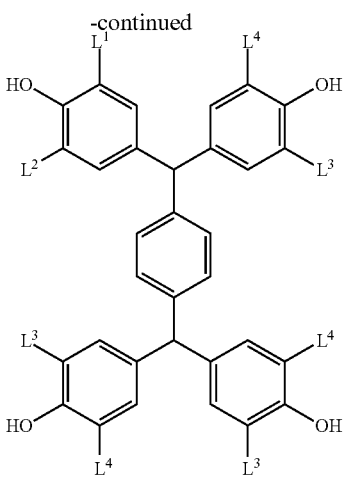

In the above formulae, $L^1$ to $L^8$ may be the same or different, and each independently represents a hydroxymethyl group, a methoxymethyl group, or an ethoxymethyl group. A phenol derivative having a hydroxymethyl group can be obtained by reacting the corresponding phenolic compound having no hydroxymethyl group (a compound where L to $L^8$ in the above formulae are a hydrogen atom) with formaldehyde in the presence of a basic catalyst. In this case, in order to prevent resignification and gelation, the reaction temperature is preferably 60° C. or less. Specifically, it can be synthesized by methods described in Japanese Patent Application Laid-Open Nos. 6-282067 and 7-64285 or the like.

A phenol derivative having an alkoxymethyl group can be obtained by reacting the corresponding phenol derivative having a hydroxymethyl group with an alcohol in the presence of an acid catalyst. In this case, in order to prevent resignification and gelation, the reaction temperature is preferably 100° C. or less. Specifically, it can be synthesized by methods described in EP632003A1 or the like.

While the phenol derivative having a hydroxymethyl group and/or an alkoxymethyl group thus synthesized is preferable in terms of stability upon storage, the phenol derivative having an alkoxymethyl group is particularly preferable in terms of stability upon storage. The acid crosslinking agent (G2) may be used alone, or may be used in combination of two or more kinds.

Other particularly preferable examples of the acid crosslinking agent (G) include a compound having at least one α-hydroxyisopropyl group (acid crosslinking agent (G3)). The compound is not particularly limited in the structure, as long as it has an α-hydroxyisopropyl group. A hydrogen atom of a hydroxyl group in the above α-hydroxyisopropyl group may be substituted with one or more acid dissociation reactive groups (R—COO— group, R—SO$_2$— group or the like, wherein R represents a substituent group selected from the group consisting of a linear hydrocarbon group of 1 to 12 carbon atoms, a cyclic hydrocarbon group of 3 to 12 carbon atoms, an alkoxy group of 1 to 12 carbon atoms, a 1-branched alkyl group of 3 to 12 carbon atoms, and an aromatic hydrocarbon group of 6 to 12 carbon atoms). Examples of a compound having the above α-hydroxyisopropyl group include one kind or two kinds or more of a substituted or non-substituted aromatic based compound, a diphenyl compound, a naphthalene compound, a furan compound or the like containing at least one α-hydroxyisopropyl group. Specific examples thereof include a compound represented by the following formula (12-1) (hereinafter, referred to as "benzene based compound (1)"), a compound represented by the following formula (12-2) (hereinafter, referred to as "diphenyl based compound (2)"), a compound represented by the following formula (12-3) (hereinafter, referred to as "naphthalene based compound (3)"), and a compound represented by the following formula (12-4) (hereinafter, referred to as "furan based compound (4)").

Formula (12-1)

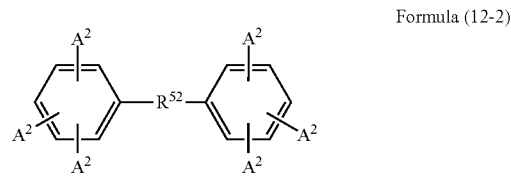

Formula (12-2)

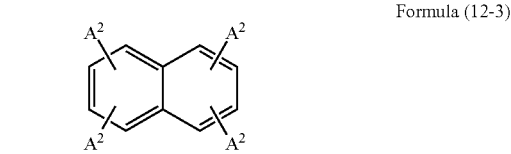

Formula (12-3)

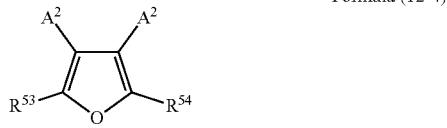

Formula (12-4)

In the above formulae (12-1) to (12-4), each $A^2$ independently represents an α-hydroxyisopropyl group or a hydrogen atom, and at least one $A^2$ is an α-hydroxyisopropyl group. In the formula (12-1), $R^{51}$ represents a hydrogen atom, a hydroxyl group, a linear or branched alkylcarbonyl group of 2 to 6 carbon atoms, or a linear or branched alkoxycarbonyl group of 2 to 6 carbon atoms. Furthermore, in the formula (10-2), $R^{52}$ represents a single bond, a linear or branched alkylene group of 1 to 5 carbon atoms, —O—, —CO—, or —COO—. Also, in the formula (12-4), $R^{53}$ and $R^{54}$ represent a hydrogen atom or a linear or branched alkyl group of 1 to 6 carbon atoms independently from each other.

Specific examples of the above benzene based compound (1) are not particularly limited, and examples include α-hydroxyisopropylbenzenes such as α-hydroxyisopropylbenzene, 1,3-bis(α-hydroxyisopropyl)benzene, 1,4-bis(α-hydroxyisopropyl)benzene, 1,2,4-tris(α-hydroxyisopropyl)benzene, and 1,3,5-tris(α-hydroxyisopropyl)benzene; α-hydroxyisopropylphenols such as 3-α-hydroxyisopropylphenol, 4-α-hydroxyisopropylphenol, 3,5-bis(α-hydroxyisopropyl)phenol, and 2,4,6-tris(α-hydroxyisopropyl)phenol; α-hydroxyisopropylphenyl alkyl ketones such as 3-α-hydroxyisopropylphenyl methyl ketone, 4-α-hydroxyisopropylphenyl methyl ketone, 4-α-hydroxyisopropylphenyl ethyl ketone, 4-α-hydroxyisopropylphenyl-n-propyl ketone, 4-α-hydroxyisopropylphenyl isopropyl ketone, 4-α-hydroxyisopropylphenyl-n-butyl ketone, 4-α-hydroxyisopropylphenyl-t-butyl ketone, 4-α-hydroxyisopropylphenyl-n-pentyl ketone, 3,5-bis(α-hydroxyisopropyl)phenyl methyl ketone, 3,5-bis(α-hydroxyisopropyl)phenyl ethyl ketone, and 2,4,6-tris(α-hydroxyisopropyl)phenyl methyl ketone; alkyl 4-α-hydroxyisopropylbenzoates such as methyl 3-α-hydroxyisopropylbenzoate, methyl 4-α-hydroxyisopropylbenzoate, ethyl 4-α-hydroxyisopropylbenzoate, n-propyl 4-α-hydroxyisopropylbenzoate, isopropyl 4-α-hydroxyisopropylbenzoate, n-butyl 4-α-hydroxyisopropylbenzoate, t-butyl 4-α-hydroxyisopropylbenzoate, n-pentyl 4-α-hydroxyisopropylbenzoate, methyl 3,5-bis(α-hydroxyisopropyl)benzoate, ethyl 3,5-bis(α-hydroxyisopropyl)benzoate, and methyl 2,4,6-tris(α-hydroxyisopropyl)benzoate.

Specific examples of the above diphenyl based compound (2) are not particularly limited, and examples include α-hydroxyisopropylbiphenyls such as 3-α-hydroxyisopropylbiphenyl, 4-α-hydroxyisopropylbiphenyl, 3,5-bis(α-hydroxyisopropyl)biphenyl, 3,3'-bis(α-hydroxyisopropyl)biphenyl, 3,4'-bis(α-hydroxyisopropyl)biphenyl, 4,4'-bis(α-hydroxyisopropyl)biphenyl, 2,4,6-tris(α-hydroxyisopropyl)biphenyl, 3,3',5-tris(α-hydroxyisopropyl)biphenyl, 3,4',5-tris(α-hydroxyisopropyl)biphenyl, 2,3',4,6-tetrakis(α-hydroxyisopropyl)biphenyl, 2,4,4',6,-tetrakis(α-hydroxyisopropyl)biphenyl, 3,3',5,5'-tetrakis(α-hydroxyisopropyl)biphenyl, 2,3',4,5',6-pentakis(α-hydroxyisopropyl)biphenyl, and 2,2',4,4',6,6'-hexakis(α-hydroxyisopropyl)biphenyl; α-hydroxyisopropyldiphenylalkanes such as 3-α-hydroxyisopropyldiphenylmethane, 4-α-hydroxyisopropyldiphenylmethane, 1-(4-α-hydroxyisopropylphenyl)-2-phenylethane, 1-(4-α-hydroxyisopropylphenyl)-2-phenylpropane, 2-(4-α-hydroxyisopropylphenyl)-2-phenylpropane, 1-(4-α-hydroxyisopropylphenyl)-3-phenylpropane, 1-(4-α-hydroxyisopropylphenyl)-4-phenylbutane, 1-(4-α-hydroxyisopropylphenyl)-5-phenylpentane, 3,5-bis(α-hydroxyisopropyldiphenylmethane, 3,3'-bis(α-hydroxyisopropyl)diphenylmethane, 3,4'-bis(α-hydroxyisopropyl)diphenylmethane, 4,4'-bis(α-hydroxyisopropyl)diphenylmethane, 1,2-bis(4-α-hydroxyisopropylphenyl)ethane, 1,2-bis(4-α-hydroxypropylphenyl)propane, 2,2-bis(4-α-hydroxypropylphenyl)propane, 1,3-bis(4-α-hydroxypropylphenyl)propane, 2,4,6-tris(α-hydroxyisopropyl)diphenylmethane, 3,3',5-tris(α-hydroxyisopropyl)diphenylmethane, 3,4',5-tris(α-hydroxyisopropyl)diphenylmethane, 2,3',4,6-tetrakis(α-hydroxyisopropyl)diphenylmethane, 2,4,4',6-tetrakis(α-hydroxyisopropyl)diphenylmethane, 3,3',5,5'-tetrakis(α-hydroxyisopropyl)diphenylmethane, 2,3',4,5',6-pentakis(α-hydroxyisopropyl)diphenylmethane, and 2,2',4,4',6,6'-hexakis(α-hydroxyisopropyl)diphenylmethane; α-hydroxyisopropyldiphenyl ethers such as 3-α-hydroxyisopropyldiphenyl ether, 4-α-hydroxyisopropyldiphenyl ether, 3,5-bis(α-hydroxyisopropyl)diphenyl ether, 3,3'-bis(α-hydroxyisopropyl)diphenyl ether, 3,4'-bis(α-hydroxyisopropyl)diphenyl ether, 4,4'-bis(α-hydroxyisopropyl)diphenyl ether, 2,4,6-tris(α-hydroxyisopropyl)diphenyl ether, 3,3',5-tris(α-hydroxyisopropyl)diphenyl ether, 3,4',5-tris(α-hydroxyisopropyl)diphenyl ether, 2,3',4,6-tetrakis(α-hydroxyisopropyl)diphenyl ether, 2,4,4',6-tetrakis(α-hydroxyisopropyl)diphenyl ether, 3,3',5,5'-tetrakis(α-hydroxyisopropyl)diphenyl ether, 2,3',4,5',6-pentakis(α-hydroxyisopropyl)diphenyl ether, and 2,2',4,4',6,6'-hexakis(α-hydroxyisopropyl)diphenyl ether; α-hydroxyisopropyldiphenyl ketones such as 3-α-hydroxyisopropyldiphenyl ketone, 4-α-hydroxyisopropyldiphenyl ketone, 3,5-bis(α-hydroxyisopropyl)diphenyl ketone, 3,3'-bis(α-hydroxyisopropyl)diphenyl ketone, 3,4'-bis(α-hydroxyisopropyl)diphenyl ketone, 4,4'-bis(α-hydroxyisopropyl)diphenyl ketone, 2,4,6-tris(α-hydroxyisopropyl)diphenyl ketone, 3,3',5-tris(α-hydroxyisopropyl)diphenyl ketone, 3,4',5-tris(α-hydroxyisopropyl)diphenyl ketone, 2,3',4,6-tetrakis(α-hydroxyisopropyl)diphenyl ketone, 2,4,4',6-tetrakis(α-hydroxyisopropyl)diphenyl ketone, 3,3',5,5'-tetrakis(α-hydroxyisopropyl)diphenyl ketone, 2,3',4,5',6-pentakis(α-hydroxyisopropyl)diphenyl ketone, and 2,2',4,4',6,6'-hexakis(α-hydroxyisopropyl)diphenyl ketone; phenyl α-hydroxyisopropylbenzoates such as phenyl 3-α-hydroxyisopropylbenzoate, phenyl 4-α-hydroxyisopropylbenzoate, 3-α-hydroxyisopropylphenyl benzoate, 4-α-hydroxyisopropylphenyl benzoate, phenyl 3,5-bis(α-hydroxyisopropyl)benzoate, 3-α-hydroxyisopropylphenyl 3-α-hydroxyisopropylbenzoate, 4-α-hydroxyisopropylphenyl 3-α-hydroxyisopropylbenzoate, 3-α-hydroxyisopropylphenyl 4-α-hydroxyisopropylbenzoate, 4-α-hydroxyisopropylphenyl 4-α-hydroxyisopropylbenzoate, 3,5-bis(α-hydroxyisopropyl)phenyl benzoate, phenyl 2,4,6-tris(α-hydroxyisopropyl)benzoate, 3-α-hydroxyisopropylphenyl 3,5-bis(α-hydroxyisopropyl)benzoate, 4-α-hydroxyisopropylphenyl 3,5-bis(α-hydroxyisopropyl)benzoate, 3,5-bis(α-hydroxyisopropyl)phenyl 3-α-hydroxyisopropylbenzoate, 3,5-bis(α-hydroxyisopropyl)phenyl 4-α-hydroxyisopropylbenzoate, 2,4,6-tris(α-hydroxyisopropyl)phenyl benzoate, 3-α-hydroxyisopropylphenyl 2,4,6-tris(α-hydroxyisopropyl)benzoate, 4-α-hydroxyisopropylphenyl 2,4,6-tris(α-hydroxyisopropyl)benzoate, 3,5-bis(α-hydroxyisopropyl)phenyl 3,5-bis(α-hydroxyisopropyl)benzoate, 2,4,6-tris(α-hydroxyisopropyl)phenyl 3-α-hydroxyisopropylbenzoate, 2,4,6-tris(α-hydroxyisopropyl)phenyl 4-α-hydroxyisopropylbenzoate, 3,5-bis(α-hydroxyisopropyl)phenyl 2,4,6-tris(α-hydroxyisopropyl)benzoate, 2,4,6-tris(α-hydroxyisopropyl)phenyl 3,5-bis(α-hydroxyisopropyl)benzoate, and 2,4,6-tris(α-hydroxyisopropyl)phenyl 2,4,6-tris(α-hydroxyisopropyl)benzoate.

Furthermore, specific examples of the above naphthalene based compound (3) are not particularly limited, and examples include 1-(α-hydroxyisopropyl)naphthalene, 2-(α-hydroxyisopropyl)naphthalene, 1,3-bis(α-hydroxyisopropyl)naphthalene, 1,4-bis(α-hydroxyisopropyl)naphthalene, 1,5-bis(α-hydroxyisopropyl)naphthalene, 1,6-bis(α-hydroxyisopropyl)naphthalene, 1,7-bis(α- hydroxyisopropyl)naphthalene, 2,6-bis(α-hydroxyisopropyl)naphthalene, 2,7-bis(α-hydroxyisopropyl)naphthalene, 1,3,5-tris(α-hydroxyisopropyl)naphthalene, 1,3,6-tris(α-hydroxyisopropyl)naphthalene, 1,3,7-tris(α-hydroxyisopropyl)naphthalene, 1,4,6-tris(α-hydroxyisopropyl)naphthalene, 1,4,7-tris(α-hydroxyisopropyl)naphthalene, and 1,3,5,7-tetrakis(α-hydroxyisopropyl)naphthalene.

Specific examples of the above furan based compound (4) include, but not particularly limited to, 3-(α-hydroxyisopropyl)furan, 2-methyl-3-(α-hydroxyisopropyl)furan, 2-methyl-4-(α-hydroxyisopropyl)furan, 2-ethyl-4-(α-hydroxyisopropyl)furan, 2-n-propyl-4-(α-hydroxyisopropyl)furan, 2-isopropyl-4-(α-hydroxyisopropyl)furan, 2-n-butyl-4-(α-hydroxyisopropyl)furan, 2-t-butyl-4-(α-hydroxyisopropyl)furan, 2-n-pentyl-4-(α-hydroxyisopropyl)furan, 2,5-dimethyl-3-(α-hydroxyisopropyl)furan, 2,5-diethyl-3-(α-hydroxyisopropyl)furan, 3,4-bis(α-hydroxyisopropyl)furan, 2,5-dimethyl-3,4-bis(α-hydroxyisopropyl)furan, and 2,5-diethyl-3,4-bis(α-hydroxyisopropyl)furan.

As the above acid crosslinking agent (G3), a compound having two or more free α-hydroxyisopropyl groups is preferable; the above benzene based compound (1) having two or more α-hydroxyisopropyl groups, the above diphenyl based compound (2) having two or more α-hydroxyisopropyl groups, and the above naphthalene based compound (3) having two or more α-hydroxyisopropyl groups are further preferable; and α-hydroxyisopropylbiphenyls having two or more α-hydroxyisopropyl groups and the above naphthalene based compound (3) having two or more α-hydroxyisopropyl groups are particularly preferable.

The above acid crosslinking agent (G3) can normally be obtained by a method for reacting an acetyl group-containing compound such as 1,3-diacetylbenzene with Grignard reagent such as $CH_3MgBr$ to methylate and then hydrolyzing, or a method for oxidizing an isopropyl group-containing compound such as 1,3-diisopropylbenzene with oxygen or the like to produce a peroxide and then reducing.

In the material composition for lithography of the present embodiment, the content of the acid crosslinking agent (G) is preferably 0.5 to 49% by mass of the total mass of the solid components, more preferably 0.5 to 40% by mass, still more preferably 1 to 30% by mass, and particularly preferably 2 to 20% by mass. When the content ratio of the above acid crosslinking agent (G) is 0.5% by mass or more, the inhibiting effect of the solubility of a resist film in an alkaline developing solution is improved, and a decrease in the film remaining rate, and occurrence of swelling and meandering of a pattern can be inhibited, which is preferable. On the other hand, when the content is 49% by mass or less, a decrease in heat resistance as a resist can be inhibited, which is preferable.

The content of at least one kind of compound selected from the above acid crosslinking agent (G1), acid crosslinking agent (G2), and acid crosslinking agent (G3) in the above acid crosslinking agent (G) is also not particularly limited, and can be within various ranges according to the kind of substrates or the like used upon forming a resist pattern.

In all acid crosslinking agent components, the content of the alkoxymethylated melamine compound and/or the compounds represented by formula (12-1) to formula (12-3) is not particularly limited, but is preferably 50 to 99% by mass, more preferably 60 to 99% by mass, still more preferably 70 to 98% by mass, and particularly preferably 80 to 97% by mass. By having the alkoxymethylated melamine compound and/or the compounds represented by formula (12-1) to formula (12-3) of 50% by mass or more of all acid crosslinking agent components, the resolution can be further improved, which is preferable. By having the compounds of 99% by mass or less, the pattern cross section is likely to have a rectangular shape, which is preferable.

(Acid Diffusion Controlling Agent (E))

The material composition for lithography of the present embodiment may contain an acid diffusion controlling agent (E) having a function of controlling diffusion of an acid generated from an acid generating agent by radiation irradiation in a resist film to inhibit any unpreferable chemical reaction in an unexposed region or the like. By using such an acid diffusion controlling agent (E), the storage stability of a material composition for lithography is improved. Also, along with the further improvement of the resolution, the line width change of a resist pattern due to variation in the post exposure delay time before radiation irradiation and the post exposure delay time after radiation irradiation can be inhibited, and the composition has extremely excellent process stability.

Such an acid diffusion controlling agent (E) is not particularly limited, and examples include a radiation degradable basic compound such as a nitrogen atom-containing basic compound, a basic sulfonium compound, and a basic iodonium compound. The acid diffusion controlling agent (E) can be used alone or in combination of two or more kinds.

The above acid diffusion controlling agent is not particularly limited, and examples include a nitrogen-containing organic compound, and a basic compound degradable by exposure. The nitrogen-containing organic compound is not particularly limited, and examples include a compound represented by the following formula (14):

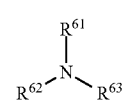

Formula (14)

The nitrogen-containing organic compound include the compound represented by the following formula (14) (hereinafter, referred to as a "nitrogen-containing compound (I)"), a diamino compound having two nitrogen atoms within the same molecule (hereinafter, referred to as a "nitrogen-containing compound (II)"), a polyamino compound or polymer having three or more nitrogen atoms (hereinafter, referred to as a "nitrogen-containing compound (III)"), an amide group-containing compound, a urea compound, and a nitrogen-containing heterocyclic compound. The acid diffusion controlling agent (E) may be used alone as one kind or may be used in combination of two or more kinds.

In the above formula (14), $R^{61}$, $R^{62}$, and $R^{63}$ represent a hydrogen atom, a linear, branched or cyclic alkyl group, an aryl group, or an aralkyl group independently from each other. The above alkyl group, aryl group, or aralkyl group may be non-substituted or may be substituted with a hydroxyl group or the like. Herein, the above linear, branched or cyclic alkyl group is not particularly limited, and examples include the one of 1 to 15 carbon atoms, and preferably 1 to 10 carbon atoms. Specific examples thereof include a methyl group, an ethyl group, an n-propyl group, an isopropyl group, an n-butyl group, an isobutyl group, a sec-butyl group, a t-butyl group, an n-pentyl group, a neopentyl group, an n-hexyl group, a texyl group, an n-heptyl group, an n-octyl group, an n-ethylhexyl group, an n-nonyl group, and an n-decyl group. Examples of the above aryl group include the one of 6 to 12 carbon atoms. Specific examples thereof include a phenyl group, a tolyl group, a xylyl group, a cumenyl group, and a 1-naphthyl group. Furthermore, the above aralkyl group is not particularly limited, and examples include the one of 7 to 19 carbon atoms, and preferably 7 to 13 carbon atoms. Specific examples thereof include a benzyl group, an α-methylbenzyl group, a phenethyl group, and a naphthylmethyl group.

The above nitrogen-containing compound (I) is not particularly limited, and specific examples include particularly mono(cyclo)alkylamines such as n-hexylamine, n-heptylamine, n-octylamine, n-nonylamine, n-decylamine, n-dodecylamine, and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, methyl-n-dodecylamine, di-n-dodecylmethyl, cyclohexylmethylamine, and dicyclohexylamine; tri (cyclo)alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, dimethyl-n-dodecylamine, di-n-dodecylmethylamine, dicyclohexylmethylamine, and tricyclohexylamine; alkanolamines such as monoethanolamine, diethanolamine, and triethanolamine; and aromatic amines such as aniline, N-methylaniline, N,N-dimethylaniline, 2-methylaniline, 3-methylaniline, 4-methylaniline, 4-nitroaniline, diphenylamine, triphenylamine, and 1-naphthylamine.

The above nitrogen-containing compound (II) is not particularly limited, and specific examples include particularly ethylenediamine, N,N,N',N'-tetramethylethylenediamine, N,N,N',N'-tetrakis(2-hydroxypropyl)ethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, and 1,3-bis[1-(4-aminophenyl)-1-methylethyl]benzene.

The above nitrogen-containing compound (III) is not particularly limited, and specific examples include particularly polymers of polyethyleneimine, polyarylamine, and N-(2-dimethylaminoethyl)acrylamide.

The above amide group-containing compound is not particularly limited, and specific examples include particularly formamide, N-methylformamide, N,N-dimethylformamide, acetamide, N-methylacetamide, N,N-dimethylacetamide, propionamide, benzamide, pyrrolidone, and N-methylpyrrolidone.

The above urea compound is not particularly limited, and specific examples include particularly urea, methylurea, 1,1-dimethylurea, 1,3-dimethylurea, 1,1,3,3-tetramethylurea, 1,3-diphenylurea, and tri-n-butylthiourea.

The above nitrogen-containing heterocyclic compound is not particularly limited, and specific examples include particularly imidazoles such as imidazole, benzimidazole, 4-methylimidazole, 4-methyl-2-phenylimidazole, and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, amide nicotinate, quinoline, 8-oxyquinoline, and acridine; and pyrazine, pyrazole, pyridazine, quinazoline, purine, pyrrolidine, piperidine, morpholine, 4-methylmorpholine, piperazine, 1,4-dimethylpiperazine, and 1,4-diazabicyclo[2.2.2]octane.

The radiation degradable basic compound is not particularly limited, and examples include a sulfonium compound represented by the following formula (15-1) and an iodonium compound represented by the following formula (15-2):

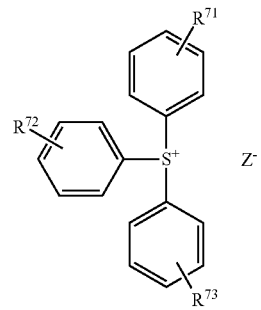

Formula (15-1)

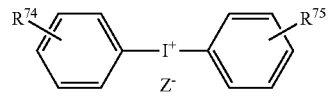

Formula (15-2)

In the above formulae (15-1) and (15-2), $R^{71}$, $R^{72}$, $R^{73}$, $R^{74}$, and $R^{75}$ each independently represent a hydrogen atom, an alkyl group of 1 to 6 carbon atoms, an alkoxyl group of 1 to 6 carbon atoms, a hydroxyl group, or a halogen atom. $Z^-$ represents $HO^-$, $R$—$COO^-$ (R represents an alkyl group of 1 to 6 carbon atoms, an aryl group of 6 to 11 carbon atoms, or an alkaryl group of 7 to 12 carbon atoms), or an anion represented by the following formula (15-3):

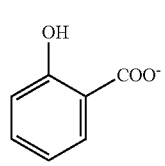

Formula (15-3)

Specific examples of the above radiation degradable basic compound are not particularly limited, and examples include triphenylsulfonium hydroxide, triphenylsulfonium acetate, triphenylsulfonium salicylate, diphenyl-4-hydroxyphenylsulfonium hydroxide, diphenyl-4-hydroxyphenylsulfonium acetate, diphenyl-4-hydroxyphenylsulfonium salicylate, bis(4-t-butylphenyl)iodonium hydroxide, bis(4-t-butylphenyl)iodonium acetate, bis(4-t-butylphenyl)iodonium hydroxide, bis(4-t-butylphenyl)iodonium acetate, bis(4-t-butylphenyl)iodonium salicylate, 4-t-butylphenyl-4-hydroxyphenyliodonium hydroxide, 4-t-butylphenyl-4-hydroxyphenyliodonium acetate, and 4-t-butylphenyl-4-hydroxyphenyliodonium salicylate.

The content of the acid diffusion controlling agent (E) is preferably 0.001 to 49% by mass of the total mass of the solid component, more preferably 0.01 to 10% by mass, still more preferably 0.01 to 5% by mass, and particularly preferably 0.01 to 3% by mass. When the content of the acid diffusion controlling agent (E) is within the above range, a decrease in resolution, and deterioration of the pattern shape and the dimension fidelity or the like can be further inhibited. Moreover, even though the post exposure delay time from electron beam irradiation to heating after radiation irradiation becomes longer, the shape of the pattern upper layer portion does not deteriorate. When the content of the acid diffusion controlling agent (E) is 10% by mass or less, a decrease in sensitivity, and developability of the unexposed portion or the like can be prevented. By using such an acid diffusion controlling agent, the storage stability of a material composition for lithography improves, also along with improvement of the resolution, the line width change of a resist pattern due to variation in the post exposure delay time before radiation irradiation and the post exposure delay time after radiation irradiation can be inhibited, and the composition is extremely excellent process stability.

(Other Component (F))

To the material composition for lithography of the present embodiment, within the range of not inhibiting the purpose of the present embodiment, if required, as the other component (F), one kind or two kinds or more of various additive agents such as a dissolution promoting agent, a dissolution controlling agent, a sensitizing agent, a surfactant and an organic carboxylic acid or an oxo acid of phosphor, or derivative thereof can be added.

—Dissolution Promoting Agent—

A low molecular weight dissolution promoting agent is a component having a function of increasing the solubility of the compound represented by the formula (A-1) or the resin comprising a constitutional unit derived from the compound represented by the formula (A-1) in a developing solution to moderately increase the dissolution rate of the compound upon developing, when the solubility of the compound or the resin is too low. The low molecular weight dissolution promoting agent can be used, within the range of not deteriorating the effect of the present invention. Examples of the above dissolution promoting agent can include low molecular weight phenolic compounds, such as bisphenols and tris(hydroxyphenyl)methane. These dissolution promoting agents can be used alone or in mixture of two or more kinds. The content of the dissolution promoting agent, which is arbitrarily adjusted according to the kind of the tellurium-containing compound represented by the formula (A-1) to be used, is preferably 0 to 49% by mass of the total mass of the solid component, more preferably 0 to 5% by mass, still more preferably 0 to 1% by mass, and particularly preferably 0% by mass.

—Dissolution Controlling Agent—

The dissolution controlling agent is a component having a function of controlling the solubility of the compound represented by the formula (A-1) or the resin comprising a constitutional unit derived from the compound represented by the formula (A-1) in a developing solution to moderately decrease the dissolution rate upon developing, when the solubility of the compound or the resin is too high. As such a dissolution controlling agent, the one which does not chemically change in steps such as calcination of resist coating, radiation irradiation, and development is preferable.

The dissolution controlling agent is not particularly limited, and examples include aromatic hydrocarbons such as phenanthrene, anthracene, and acenaphthene; ketones such as acetophenone, benzophenone, and phenyl naphtyl ketone; and sulfones such as methyl phenyl sulfone, diphenyl sulfone, and dinaphthyl sulfone. These dissolution controlling agents can be used alone or in two or more kinds.

The content of the dissolution controlling agent is not particularly limited and is arbitrarily adjusted according to the kind of the compound represented by the formula (A-1) or the resin comprising a constitutional unit derived from the compound represented by the formula (A-1) to be used, but is preferably 0 to 49% by mass of the total mass of the solid component, more preferably 0 to 5% by mass, still more preferably 0 to 1% by mass, and particularly preferably 0% by mass.

—Sensitizing Agent—

The sensitizing agent is a component having a function of absorbing irradiated radiation energy, transmitting the energy to the acid generating agent (C), and thereby increasing the acid production amount, and improving the apparent sensitivity of a resist. Such a sensitizing agent is not particularly limited, and examples include benzophenones, biacetyls, pyrenes, phenothiazines, and fluorenes. These sensitizing agents can be used alone or in two or more kinds. The content of the sensitizing agent, which is arbitrarily adjusted according to the kind of the compound represented by the formula (A-1) or the resin comprising a constitutional unit derived from the compound represented by the formula (A-1) to be used, is preferably 0 to 49% by mass of the total mass of the solid component, more preferably 0 to 5% by mass, still more preferably 0 to 1% by mass, and particularly preferably 0% by mass.

—Surfactant—

The surfactant is a component having a function of improving coatability and striation of the material composition for lithography of the present embodiment, and developability of a resist or the like. Such a surfactant is not particularly limited, and may be any of anionic, cationic, nonionic or amphoteric. A preferable surfactant is a nonionic surfactant. The nonionic surfactant has a good affinity with a solvent used in production of material compositions for lithography and more effects. Examples of the nonionic surfactant include, but not particularly limited to, a polyoxyethylene higher alkyl ethers, polyoxyethylene higher alkyl phenyl ethers, and higher fatty acid diesters of polyethylene glycol. Examples of commercially available products include, hereinafter by trade name, EFTOP (manufactured by Jemco Inc.), MEGAFAC (manufactured by DIC Corporation), Fluorad (manufactured by Sumitomo 3M Limited), AsahiGuard, Surflon (hereinbefore, manufactured by Asahi Glass Co., Ltd.), Pepole (manufactured by Toho Chemical Industry Co., Ltd.), KP (manufactured by Shin-Etsu Chemical Co., Ltd.), and Polyflow (manufactured by Kyoeisha Chemical Co., Ltd.). The content of the surfactant is not particularly limited, and is arbitrarily adjusted according to the kind of the compound represented by the formula (A-1) or the resin comprising a constitutional unit derived from the compound represented by the formula (A-1) to be used, but is preferably 0 to 49% by mass of the total mass of the solid component, more preferably 0 to 5% by mass, still more preferably 0 to 1% by mass, and particularly preferably 0% by mass.

—Organic Carboxylic Acid or Oxo Acid of Phosphor or Derivative Thereof—

For the purpose of prevention of sensitivity deterioration or improvement of a resist pattern shape and post exposure delay stability or the like, and as an additional optional component, the material composition for lithography of the present embodiment may contain an organic carboxylic acid or an oxo acid of phosphor or derivative thereof. The composition can be used in combination with the acid diffusion controlling agent, or may be used alone. The organic carboxylic acid is not particularly limited, and, for example, is suitably malonic acid, citric acid, malic acid, succinic acid, benzoic acid, salicylic acid, or the like.

Examples of the oxo acid of phosphor or derivative thereof include phosphoric acid or derivative thereof such as ester including phosphoric acid, di-n-butyl ester phosphate, and diphenyl ester phosphate; phosphonic acid or derivative thereof such as ester including phosphonic acid, dimethyl ester phosphonate, di-n-butyl ester phosphonate, phenylphosphonic acid, diphenyl ester phosphonate, and dibenzyl ester phosphonate; and phosphinic acid and derivative thereof such as ester including phosphinic acid and phenylphosphinic acid. Among these, phosphonic acid is particularly preferable.

The organic carboxylic acid or the oxo acid of phosphor or derivative thereof can be used alone or in combination of two or more kinds. The content of the organic carboxylic acid or the oxo acid of phosphor or derivative thereof, which is arbitrarily adjusted according to the kind of the compound represented by the formula (A-1) or the resin comprising a constitutional unit derived from the compound represented by the formula (A-1) to be used, is preferably 0 to 49% by mass of the total mass of the solid component, more preferably 0 to 5% by mass, still more preferably 0 to 1% by mass, and particularly preferably 0% by mass.

—Other Additive Agent—

Furthermore, the material composition for lithography of the present embodiment can contain one kind or two kinds or more of additive agents other than the above dissolution controlling agent, sensitizing agent, and surfactant, within the range of not inhibiting the purpose of the present invention, if required. Examples of such an additive agent include, but not particularly limited to, a dye, a pigment, and an adhesion aid. For example, the composition contains the dye or the pigment, and thereby a latent image of the exposed portion is visualized and influence of halation upon exposure can be alleviated, which is preferable. The composition contains the adhesion aid, and thereby adhesiveness to a substrate can be improved, which is preferable. Furthermore, examples of other additive agent can include, but not particularly limited to, a halation preventing agent, a storage stabilizing agent, a defoaming agent, and a shape improving agent. Specific examples thereof can include 4-hydroxy-4'-methylchalkone.

The total content of the optional component (F) is preferably 0 to 49% by mass of the total mass of the solid component, more preferably 0 to 5% by mass, still more preferably 0 to 1% by mass, and particularly preferably 0% by mass.

In the material composition for lithography of the present embodiment, the content of the compound represented by the formula (A-1) or the resin comprising a constitutional unit derived from the compound represented by the formula (A-1), the acid generating agent (C), the acid diffusion controlling agent (E), the optional component (F) (the compound represented by the formula (A-1) or the resin comprising a constitutional unit derived from the compound represented by the formula (A-1)/the acid generating agent (C)/the acid diffusion controlling agent (E)/the optional component (F)) is preferably 50 to 99.4/0.001 to 49/0.001 to 49/0 to 49 in % by mass based on the solid content, more preferably 55 to 90/1 to 40/0.01 to 10/0 to 5, still more preferably 60 to 80/3 to 30/0.01 to 5/0 to 1, and particularly preferably 60 to 70/10 to 25/0.01 to 3/0.

The content ratio of each component is selected from each range so that the summation thereof is 100% by mass. By the above content ratio, performance such as sensitivity, resolution, and developability is even better.

The method for purifying the material composition for lithography of the present embodiment is not particularly limited, and, examples include a method involving dissolving each component in a solvent upon use into a homogenous solution, and then if required, filtering through a filter or the like with a pore diameter of about 0.2 m, for example.

The material composition for lithography of the present embodiment can contain a resin within the range of not inhibiting the purpose of the present invention. Examples of the resin include, but not particularly limited to, a novolac resin, polyvinyl phenols, polyacrylic acid, polyvinyl alcohol, a styrene-maleic anhydride resin, an acrylic acid, vinyl alcohol or vinylphenol as a monomeric unit, or derivative thereof. The content of the resin is not particularly limited, and is arbitrarily adjusted according to the kind of the compound represented by the formula (A) or the resin comprising a constitutional unit derived from the compound represented by the formula (A) to be used, but is preferably 30 parts by mass or less per 100 parts by mass of the compound, more preferably 10 parts by mass or less, still more preferably 5 parts by mass or less, particularly preferably 0 parts by mass.

[Resist Pattern Formation Method]

In the case of forming a pattern on a substrate using the material for lithography, for example, a pattern formation method can be used, comprising: a film formation step of forming a film on a substrate using the material for lithography or a composition comprising this material (hereinafter, these are also collectively referred to as a "material, etc. for lithography"); an exposure step of exposing the film; and a development step of developing the film exposed in the exposure step, thereby forming a pattern.

For example, in the case of forming a resist pattern using the material, etc. for lithography of the present embodiment, a pattern (resist pattern) formation method is not particularly limited, and a suitable method may be a method including: a film formation step of forming a film (resist film) by coating a substrate with a resist composition comprising the material, etc. for lithography mentioned above; an exposure step of exposing the formed film (resist film); and a development step of developing the film (resist film) exposed in the exposure step, thereby forming a pattern (resist pattern).

The resist pattern of the present embodiment can also be formed as an upper layer resist in a multilayer process.

Specific examples of the resist pattern formation method include, but not particularly limited to, the following methods. A resist film is formed by coating a conventionally publically known substrate with the above resist composition using a coating means such as spin coating, flow casting coating, and roll coating. The conventionally publically known substrate is not particularly limited. For example, a substrate for electronic components, and the one having a predetermined wiring pattern formed thereon, or the like can be exemplified. More specific examples are not particularly limited, and examples include a substrate made of a metal such as a silicon wafer, copper, chromium, iron and aluminum, and a glass substrate. Examples of a wiring pattern material include, but not particularly limited to, copper, aluminum, nickel, and gold. Also if required, the substrate may be a substrate having an inorganic film and/or organic film provided thereon. Examples of the inorganic film include, but not particularly limited to, an inorganic antireflection film (inorganic BARC). Examples of the organic film include, but not particularly limited to, an organic antireflection film (organic BARC). Surface treatment with hexamethylene disilazane or the like may be conducted.

Next, the coated substrate is heated if required. The heating conditions vary according to the compounding composition of the resist composition, or the like, but are preferably 20 to 250° C., and more preferably 20 to 150° C. By heating, the adhesiveness of a resist to a substrate may improve, which is preferable. Then, the resist film is exposed to a desired pattern by any radiation selected from the group consisting of visible light, ultraviolet, excimer laser, electron beam, extreme ultraviolet (EUV), X-ray, and ion beam. The exposure conditions or the like are arbitrarily selected according to the compounding composition of the resist composition, or the like.

In the resist pattern formation method of the present embodiment, in order to stably form a fine pattern with a high degree of accuracy in exposure, the resist film is preferably heated after radiation irradiation. The heating conditions vary according to the compounding composition of the resist composition, or the like, but are preferably 20 to 250° C., and more preferably 20 to 150° C.

Next, by developing the exposed resist film in a developing solution, a predetermined resist pattern is formed.

As the developing solution, a solvent having a solubility parameter (SP value) close to that of the compound represented by the formula (A-1) or the resin comprising a constitutional unit derived from the compound represented by the formula (A-1) to be used is preferably selected. A polar solvent such as a ketone-based solvent, an ester-based solvent, an alcohol-based solvent, an amide-based solvent, and an ether-based solvent; and a hydrocarbon-based solvent, or an alkaline aqueous solution can be used.

Depending on the kind of the developing solution, a positive type resist pattern and a negative type resist pattern can be individually prepared. In general, in the case of a polar solvent such as a ketone-based solvent, an ester-based solvent, an alcohol-based solvent, an amide-based solvent, and an ether-based solvent, or a hydrocarbon-based solvent, a negative type resist pattern is obtained, and in the case of an alkaline aqueous solution, a positive type resist pattern is obtained.

The ketone-based solvent is not particularly limited, and examples include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, and propylene carbonate.

The ester-based solvent is not particularly limited, and examples include methyl acetate, butyl acetate, ethyl acetate, isopropyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, and propyl lactate.

The alcohol-based solvent is not particularly limited, and examples include an alcohol such as methyl alcohol, ethyl alcohol, n-propyl alcohol, isopropyl alcohol (2-propanol), n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; and a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol.

The ether-based solvent is not particularly limited, and examples include dioxane and tetrahydrofuran in addition to the glycol ether-based solvents.

The amide-based solvent is not particularly limited, and examples can be used include N-methyl-2-pyrrolidone, N,N-dimethylacetamide, N,N-dimethylformamide, phosphoric hexamethyltriamide, and 1,3-dimethyl-2-imidazolidinone.

The hydrocarbon-based solvent is not particularly limited, and examples include an aromatic hydrocarbon-based solvent such as toluene and xylene; and an aliphatic hydrocarbon-based solvent such as pentane, hexane, octane, and decane.

A plurality of above solvents may be mixed, or the solvent may be used by mixing the solvent with a solvent other than those described above or water within the range having performance. In order to sufficiently exhibit the effect of the present invention, the water content ratio as the whole developing solution is preferably less than 70% by mass and even less than 50% by mass, more preferably less than 30% by mass, and further preferably less than 10% by mass. Particularly preferably, the developing solution is substantially moisture free. That is, the content of the organic solvent in the developing solution is not particularly limited, and is preferably 30% by mass or more and 100% by mass or less based on the total amount of the developing solution, preferably even 50% by mass or more and 100% by mass or less, more preferably 70% by mass or more and 100% by mass or less, further more preferably 90% by mass or more and 100% by mass or less, and particularly preferably 95% by mass or more and 100% by mass or less.

The alkaline aqueous solution is not particularly limited, and examples include an alkaline compound such as mono-, di- or tri-alkylamines, mono-, di- or tri-alkanolamines, heterocyclic amines, tetramethyl ammonium hydroxide (TMAH), and choline.

Particularly, the developing solution containing at least one kind of solvent selected from a ketone-based solvent, an ester-based solvent, an alcohol-based solvent, an amide-based solvent, and an ether-based solvent improves resist performance such as resolution and roughness of the resist pattern, which is preferable.

The vapor pressure of the developing solution is not particularly limited, and is preferably 5 kPa or less at 20° C., more preferably 3 kPa or less, and particularly preferably 2 kPa or less, for example. The evaporation of the developing solution on the substrate or in a developing cup is inhibited by setting the vapor pressure of the developing solution to 5 kPa or less, to improve temperature uniformity within a wafer surface, thereby resulting in improvement in size uniformity within the wafer surface.

Specific examples having a vapor pressure of 5 kPa or less include a ketone-based solvent such as 1-octanone, 2-octanone, 1-nonanone, 2-nonanone, 4-heptanone, 2-hexanone, diisobutyl ketone, cyclohexanone, methylcyclohexanone, phenylacetone, and methyl isobutyl ketone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, butyl formate, propyl formate, ethyl lactate, butyl lactate, and propyl lactate; an alcohol-based solvent such as n-propyl alcohol, isopropyl alcohol, n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an ether-based solvent such as tetrahydrofuran; an amide-based solvent such as N-methyl-2-pyrrolidone, N,N-dimethylacetamide, and N,N-dimethylformamide; an aromatic hydrocarbon-based solvent such as toluene and xylene; and an aliphatic hydrocarbon-based solvent such as octane and decane.

Specific examples having a vapor pressure of 2 kPa or less which is a particularly preferable range include a ketone-based solvent such as 1-octanone, 2-octanone, 1-nonanone, 2-nonanone, 4-heptanone, 2-hexanone, diisobutyl ketone, cyclohexanone, methylcyclohexanone, and phenylacetone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, ethyl lactate, butyl lactate, and propyl lactate; an alcohol-based solvent such as n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an amide-based solvent such as N-methyl-2-pyrrolidone, N,N-dimethylacetamide, and N,N-dimethylformamide; an aromatic hydrocarbon-based solvent such as xylene; and an aliphatic hydrocarbon-based solvent such as octane and decane.

To the developing solution, a surfactant can be added in an appropriate amount, if required. The surfactant is not particularly limited but, for example, an ionic or nonionic fluorine-based and/or silicon-based surfactant can be used. Examples of the fluorine-based and/or silicon-based surfactant include the surfactants described in Japanese Patent Application Laid-Open Nos. 62-36663, 61-226746, 61-226745, 62-170950, 63-34540, 7-230165, 8-62834, 9-54432, and 9-5988, and U.S. Pat. Nos. 5,405,720, 5,360,692, 5,529,881, 5,296,330, 5,436,098, 5,576,143, 5,294,511, and 5,824,451. The surfactant is preferably a nonionic surfactant. The nonionic surfactant is not particularly limited, but a fluorine-based surfactant or a silicon-based surfactant is further preferably used.

The amount of the surfactant used is usually 0.001 to 5% by mass based on the total amount of the developing solution, preferably 0.005 to 2% by mass, and further preferably 0.01 to 0.5% by mass.

The development method is, for example, a method for dipping a substrate in a bath filled with a developing solution for a fixed time (dipping method), a method for raising a developing solution on a substrate surface by the effect of a surface tension and keeping it still for a fixed time, thereby conducting the development (puddle method), a method for spraying a developing solution on a substrate surface (spraying method), and a method for continuously ejecting a developing solution on a substrate rotating at a constant speed while scanning a developing solution ejecting nozzle at a constant rate (dynamic dispense method), or the like may be applied. The time for conducting the pattern development is not particularly limited, but is preferably 10 seconds to 90 seconds.

After the step of conducting development, a step of stopping the development by the replacement with another solvent may be practiced.

A step of rinsing the resist film with a rinsing solution containing an organic solvent is preferably provided after the development.

The rinsing solution used in the rinsing step after development is not particularly limited as long as the rinsing solution does not dissolve the resist pattern cured by cross-linking. A solution containing a general organic solvent or water may be used as the rinsing solution. As the rinsing solution, a rinsing solution containing at least one kind of organic solvent selected from a hydrocarbon-based solvent, a ketone-based solvent, an ester-based solvent, an alcohol-based solvent, an amide-based solvent, and an ether-based solvent is preferably used. More preferably, after development, a step of rinsing the film by using a rinsing solution containing at least one kind of organic solvent selected from the group consisting of a ketone-based solvent, an ester-based solvent, an alcohol-based solvent and an amide-based solvent is conducted. Still more preferably, after development, a step of rinsing the film by using a rinsing solution containing an alcohol-based solvent or an ester-based solvent is conducted. Further more preferably, after development, a step of rinsing the film by using a rinsing solution containing a monohydric alcohol is conducted. Particularly preferably, after development, a step of rinsing the film by using a rinsing solution containing a monohydric alcohol having 5 or more carbon atoms is conducted. The time for rinsing the pattern is not particularly limited, but is preferably 10 seconds to 90 seconds.

Herein, examples of the monohydric alcohol used in the rinsing step after development are not particularly limited, and specific examples include a linear, branched or cyclic monohydric alcohol. Specific examples include 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, and 4-octanol or the like can be used. Particularly preferable examples of monohydric alcohol having 5 or more carbon atoms include, but not limited to, 1-hexanol, 2-hexanol, 4-methyl-2-pentanol, 1-pentanol, and 3-methyl-1-butanol or the like can be used.

A plurality of these components may be mixed, or the component may be used by mixing the component with an organic solvent other than those described above.

The water content ratio in the rinsing solution is not particularly limited, and is preferably 10% by mass or less, more preferably 5% by mass or less, and particularly preferably 3% by mass or less. By setting the water content ratio to 10% by mass or less, better development characteristics can be obtained.

The vapor pressure at 20° C. of the rinsing solution used after development is preferably 0.05 kPa or more and 5 kPa or less, more preferably 0.1 kPa or more and 5 kPa or less, and much more preferably 0.12 kPa or more and 3 kPa or less. By setting the vapor pressure of the rinsing solution to 0.05 kPa or more and 5 kPa or less, the temperature uniformity in the wafer surface is enhanced and moreover, swelling due to permeation of the rinsing solution is further inhibited. As a result, the dimensional uniformity in the wafer surface is further improved.

The rinsing solution may also be used after adding an appropriate amount of a surfactant to the rinsing solution.

In the rinsing step, the wafer after development is rinsed using the organic solvent-containing rinsing solution. The method for rinsing treatment is not particularly limited. However, for example, a method for continuously ejecting a rinsing solution on a substrate spinning at a constant speed (spin coating method), a method for dipping a substrate in a bath filled with a rinsing solution for a fixed time (dipping method), and a method for spraying a rinsing solution on a substrate surface (spraying method), or the like can be applied. Above all, it is preferable to conduct the rinsing treatment by the spin coating method and after the rinsing, spin the substrate at a rotational speed of 2,000 rpm to 4,000 rpm, to remove the rinsing solution from the substrate surface.

After forming the resist pattern, a pattern wiring substrate is obtained by etching. Etching can be conducted by a publicly known method such as dry etching using plasma gas, and wet etching with an alkaline solution, a cupric chloride solution, and a ferric chloride solution or the like.

After forming the resist pattern, plating can also be conducted. Examples of the above plating method include, but not particularly limited to, copper plating, solder plating, nickel plating, and gold plating.

The remaining resist pattern after etching can be peeled by an organic solvent. Examples of the above organic solvent are not particularly limited, and examples include PGMEA (propylene glycol monomethyl ether acetate), PGME (propylene glycol monomethyl ether), and EL (ethyl lactate). Examples of the above peeling method are not particularly limited, and examples include a dipping method and a spraying method. A wiring substrate having a resist pattern formed thereon may be a multilayer wiring substrate, and may have a small diameter through hole.

In the present embodiment, the wiring substrate can also be formed by a method for forming a resist pattern, then depositing a metal in vacuum, and subsequently dissolving the resist pattern in a solution, i.e., a liftoff method.

EXAMPLES

The present embodiment will be more specifically described with reference to examples below. However, the present invention is not limited to these examples.

Below, methods for measuring a compound and methods for evaluating resist performance and the like in examples are presented.

[Measurement Method]
(1) Structure of Compound

The structure of the compound was verified by carrying out $^1$H-NMR measurement under the following conditions using "Advance 600 II spectrometer" manufactured by Bruker.

Frequency: 400 MHz
Solvent: d6-DMSO (except for Synthesis Example 4)
Internal standard: TMS
Measurement temperature: 23° C.

(2) Molecular Weight of Compound

The molecular weight of the compound was measured by GC-MS analysis using "Agilent 5975/6890N" manufactured by Agilent Technologies, Inc. or by LC-MS analysis using "Acquity UPLC/MALDI-Synapt HDMS" manufactured by Waters Corp.

(3) Metal Content of Compound

The metal content of the compound was measured by ICP-MS analysis using "ELAN DRC II" manufactured by PerkinElmer.

[Evaluation Method]
(1) Safe Solvent Solubility Test of Compound

The solubility of the compound in propylene glycol monomethyl ether acetate was measured as the solubility of the compound in a safe solvent. The solubility was evaluated according to the following criteria utilizing the amount of dissolution in propylene glycol monomethyl ether acetate. The amount of dissolution was measured at 23° C. by precisely weighing the compound into a test tube, adding propylene glycol monomethyl ether acetate so as to attain a predetermined concentration, applying ultrasonic waves for 30 minutes in an ultrasonic cleaner, then visually observing the subsequent state of the fluid, and conducting evaluation on the basis of the concentration of the amount of complete dissolution.

A: 5.0% by mass≤Amount of dissolution
B: 3.0% by mass≤Amount of dissolution<5.0% by mass
C: Amount of dissolution<3.0% by mass (2) Storage Stability and Thin Film Formability of Resist Composition The storage stability of a resist composition containing the compound was evaluated by leaving the resist composition to stand still for three days at 23° C. after preparation and then visually observing the resist composition for the presence and absence of precipitates. The resist composition after being left to stand still for three days was evaluated as "A" when it was a homogeneous solution without precipitates, and "C" when precipitates were observed.

A clean silicon wafer was spin coated with the resist composition in a homogeneous state, and then prebaked (PB) before exposure in an oven of 110° C. to form a resist film with a thickness of 40 nm. The prepared resist composition was evaluated as "A" when the thin film formability was good, and "C" when the formed film had defects.

(3) Pattern Evaluation of Resist Pattern (Sensitivity and Shape Evaluation)

A clean silicon wafer was spin coated with a homogeneous resist composition, and then prebaked (PB) before exposure in an oven of 110° C. to form a resist film with a thickness of 60 nm. The obtained resist film was irradiated with electron beams of 1:1 line and space setting with 50 nm, 40 nm, and 30 nm intervals using an electron beam lithography system (ELS-7500 manufactured by ELIONIX INC.). After irradiation, the resist film was heated at each predetermined temperature for 90 seconds, and immersed in 2.38% by mass tetramethyl ammonium hydroxide (TMAH) alkaline developing solution for 60 seconds for development. Subsequently, the resist film was washed with ultrapure water for 30 seconds, and dried to form a positive type resist pattern. Concerning the formed resist pattern, the line and space were observed using a scanning electron microscope ("S-4800" manufactured by Hitachi High-Technologies Corporation) to evaluate the reactivity (sensitivity) by electron beam irradiation of the resist composition. The sensitivity was indicated by the minimum amount of energy per unit area necessary for obtaining the pattern, and evaluated as "A" when the pattern was obtained at less than 50 µC/cm$^2$, and "C" when the pattern was obtained at 50 µC/cm$^2$ or more. Also, the obtained pattern shape was observed under SEM (scanning electron microscope), and evaluated as "A" when a rectangular pattern was obtained, "B" when an almost rectangular pattern was obtained, and "C" when a non-rectangular pattern was obtained.

SYNTHESIS EXAMPLES

(Synthesis Example 1) Synthesis of Compound (BHPT)

In a glove box, to a 50 mL container, tellurium tetrachloride (5.39 g, 20 mmol) was fed, 10.8 g (100 mmol) of anisole was added, and the mixture was reacted at 160° C. for 6 hours under reflux conditions. The obtained product was dried under reduced pressure, and recrystallization was carried out twice using acetonitrile, followed by filtration to obtain orange crystals. The obtained crystals were dried under reduced pressure for 24 hours to obtain 5.95 g of BMPT (bis(4-methoxyphenyl)tellurium dichloride).

As a result of measuring the molecular weight of the obtained compound (BMPT) by the above measurement method (LC-MS), it was 414.

The following peaks were found by NMR measurement performed on the obtained compound (BMPT) under the above measurement conditions, and the compound was confirmed to have a chemical structure of the compound (BMPT) shown below.

δ (ppm) 7.0-7.9 (8H, Ph-H), 3.8 (6H, —CH$_3$)

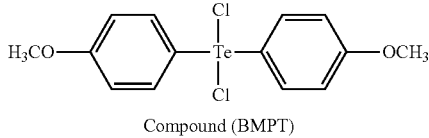

Compound (BMPT)

Then, to a container (internal capacity: 100 mL) equipped with a stirrer, a condenser tube, and a burette, 1.1 g (2.8 mmol) of bis(4-methoxyphenyl)tellurium dichloride and 18 ml of methylene dichloride were added, 3.9 g (15.75 mmol) of boron tribromide was dropped, and the mixture was reacted at −20° C. for 48 hours. The solution after reaction was dropped to a 0.5N hydrochloric acid solution in an ice bath, and a yellow solid was recovered after filtration. The solid was dissolved in ethyl acetate, the solution was dehydrated by the addition of magnesium sulfate and then concentrated, and the residue was separated and purified by column chromatography to obtain 0.1 g of BHPT (bis(4-hydroxyphenyl)tellurium dichloride).

As a result of measuring the molecular weight of the obtained compound (BHPT) by the above measurement method (LC-MS), it was 386.

The following peaks were found by NMR measurement performed on the obtained compound (BHPT) under the above measurement conditions, and the compound was confirmed to have a chemical structure of the compound (BHPT) shown below.

δ (ppm) 10.2 (2H, —OH), 6.8-7.8 (8H, Ph-H)

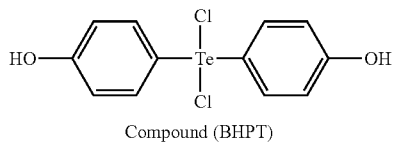

Compound (BHPT)

(Synthesis Example 2) Synthesis of Compound (BHPT-ADBAC)

In a container (internal capacity: 200 mL) equipped with a stirrer, a condenser tube, and a burette, 3.9 g (10 mmol) of the compound (BHPT) obtained as mentioned above, 0.30 g (22 mmol) of potassium carbonate, and 0.64 g (2 mmol) of tetrabutyl ammonium bromide were dissolved in 50 ml of N-methylpyrrolidone, and the solution was stirred for 2 hours. After stirring, 6.3 g (22 mmol) of bromoacetic acid-2-methyladamantan-2-yl was further added thereto, and the mixture was reacted at 100° C. for 24 hours. After the reaction terminated, the reaction mixture was dropped to a 1 N aqueous hydrochloric acid solution, and the resulting black solid was filtered off and separated and purified by column chromatography to obtain 1.9 g of the following compound (BHPT-ADBAC: bis(4-(2-methyl-2-adamantyloxycarbonylmethoxy)phenyl)tellurium dichloride).

As a result of measuring the molecular weight of the obtained compound (BHPT-ADBAC) by the above measurement method (LC-MS), it was 798.

The following peaks were found by NMR measurement performed on the obtained compound (BHPT-ADBAC) under the above measurement conditions, and the compound was confirmed to have a chemical structure of the compound (BHPT-ADBAC) shown below.

δ (ppm) 6.8-8.1 (8H, Ph-H), 4.7-5.0 (4H, O—CH$_2$—C(=O)—), 1.2-2.7 (34H, C—H/Adamantane of methylene and methine)

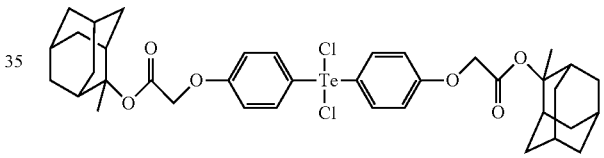

Compound (BHPT-ADBAC)

(Synthesis Example 3) Synthesis of Compound (BHPT-BOC)

In a container (internal capacity: 200 mL) equipped with a stirrer, a condenser tube, and a burette, 3.9 g (10 mmol) of the compound (BHPT) obtained as mentioned above and 5.5 g (25 mmol) of di-t-butyl dicarbonate (manufactured by Sigma-Aldrich) were dissolved in 50 ml of N-methylpyrrolidone, 0.30 g (22 mmol) of potassium carbonate was added to the solution, and the mixture was reacted at 100° C. for 24 hours. After the reaction terminated, the reaction mixture was dropped to a 1 N aqueous hydrochloric acid solution, and the resulting black solid was filtered off and separated and purified by column chromatography to obtain 1.0 g of the following compound (BHPT-BOC: bis(tert-butoxycarboxyphenyl)tellurium dichloride).

As a result of measuring the molecular weight of the obtained compound (BHPT-BOC) by the above measurement method (LC-MS), it was 585.

The following peaks were found by NMR measurement performed on the obtained compound (BHPT-BOC) under the above measurement conditions, and the compound was confirmed to have a chemical structure of the compound (BHPT-BOC) shown below.

δ (ppm) 7.1-7.3 (8H, Ph-H), 1.4 (18H, C—CH$_3$)

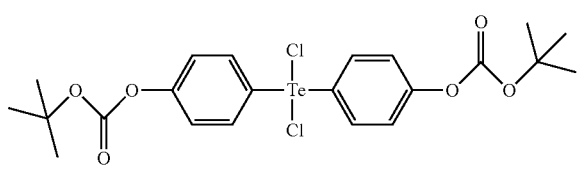

Compound (BHPT-BOC)

(Synthesis Example 4) Synthesis of Compound (BHPT-EE)

In a container (internal capacity: 200 mL) equipped with a stirrer, a condenser tube, and a burette, 3.9 g (10 mmol) of the compound (BHPT) obtained as mentioned above and 1.8 g (25 mmol) of ethyl vinyl ether (manufactured by Tokyo Kasei Kogyo Co., Ltd.) were dissolved in 50 ml of N-methylpyrrolidone, 0.30 g (22 mmol) of potassium carbonate was added to the solution, and the mixture was reacted at 100° C. for 24 hours. After the reaction terminated, the reaction mixture was dropped to a 1 N aqueous hydrochloric acid solution, and the resulting black solid was filtered off and separated and purified by column chromatography to obtain 1.0 g of the following compound (BHPT-EE: bis(ethoxy-ethylphenyl)tellurium dichloride).

As a result of measuring the molecular weight of the obtained compound (BHPT-EE) by the above measurement method (LC-MS), it was 529.

The following peaks were found by NMR measurement performed on the obtained compound (BHPT-EE) under the above measurement conditions, and the compound was confirmed to have a chemical structure of the compound (BHPT-EE) shown below.

δ (ppm) 6.9-7.4 (8H, Ph-H), 5.6 (2H, C$\underline{H}$), 1.6 (6H, —C$\underline{H}_3$), 3.9 (4H, O—C$\underline{H}_2$—), 1.2 (6H, —C$\underline{H}_3$)

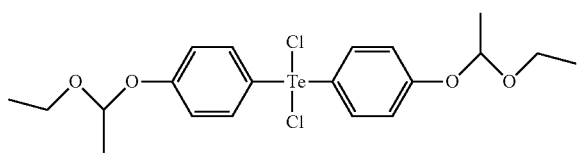

Compound (BHPT-EE)

(Synthesis Example 5) Synthesis of Compound (Ph-BHPT)

In a glove box, to a 50 mL container, tellurium tetrachloride (5.39 g, 20 mmol) was fed, 7.37 g (40 mmol) of 2-phenylanisole was added, and the mixture was reacted at 160° C. for 6 hours under reflux conditions. The obtained product was dried under reduced pressure, and recrystallization was carried out twice using acetonitrile, followed by filtration to obtain orange crystals. The obtained crystals were dried under reduced pressure for 24 hours to obtain 3.91 g of Ph-BMPT (bis(3-phenyl-4-methoxyphenyl)tellurium dichloride).

As a result of measuring the molecular weight of the obtained compound (Ph-BMPT) by the above measurement method (LC-MS), it was 465.

The following peaks were found by NMR measurement performed on the obtained compound (Ph-BMPT) under the above measurement conditions, and the compound was confirmed to have a chemical structure of the compound (Ph-BMPT) shown below.

δ (ppm) 7.0-8.1 (16H, Ph-H), 3.8 (6H, —CH$_3$)

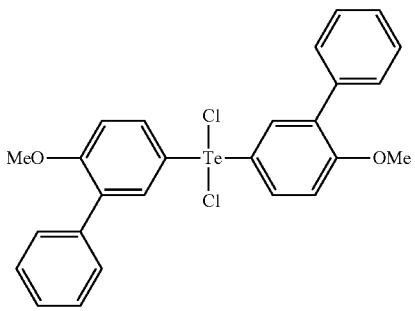

Compound (Ph-BMPT)

Then, to a container (internal capacity: 100 mL) equipped with a stirrer, a condenser tube, and a burette, 1.6 g (2.8 mmol) of Ph-BMPT and 25 ml of methylene dichloride were added, 3.9 g (15.75 mmol) of boron tribromide was dropped, and the mixture was reacted at −20° C. for 48 hours. The solution after reaction was dropped to a 0.5N hydrochloric acid solution in an ice bath, and a yellow solid was recovered after filtration. The solid was dissolved in ethyl acetate, the solution was dehydrated by the addition of magnesium sulfate and then concentrated, and the residue was separated and purified by column chromatography to obtain 0.2 g of Ph-BHPT (bis(3-phenyl-4-hydroxyphenyl)tellurium dichloride).

As a result of measuring the molecular weight of the obtained compound (Ph-BHPT) by the above measurement method (LC-MS), it was 537.

The following peaks were found by NMR measurement performed on the obtained compound (Ph-BHPT) under the above measurement conditions, and the compound was confirmed to have a chemical structure of the compound (Ph-BHPT) shown below.

δ (ppm) 9.0 (2H, —OH), 7.0-7.5 (16H, Ph-H)

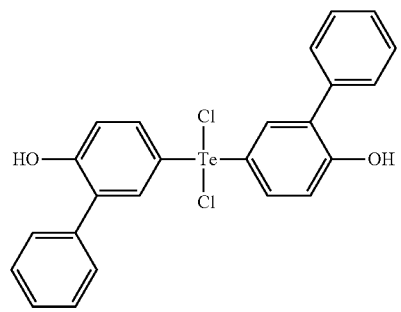

Compound (Ph-BHPT)

(Synthesis Example 6) Synthesis of Compound (TDP)

In a glove box, to a 50 mL container, tellurium tetrachloride (6.74 g, 25 mmol) was fed, 3.29 g (35 mmol) of phenol was added, and the mixture was reacted at 160° C. for 6 hours under reflux conditions. The obtained product was dried under reduced pressure, and recrystallization was carried out twice using acetonitrile, followed by filtration to obtain brown crystals. The obtained crystals were dried under reduced pressure for 24 hours to obtain 3.60 g of TDP (4,4'-telluriumdiphenol).

As a result of measuring the molecular weight of the obtained compound (TDP) by the above measurement method (LC-MS), it was 314.

The following peaks were found by NMR measurement performed on the obtained compound (TDP) under the above measurement conditions, and the compound was confirmed to have a chemical structure of the compound (TDP) shown below.

δ (ppm) 6.8-7.7 (8H, Ph-H), 9.8 (2H, —OH)

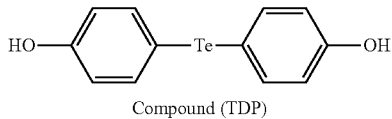

Compound (TDP)

(Synthesis Example 7) Synthesis of Compound (Ph-TDP)

In a glove box, to a 50 mL container, tellurium tetrachloride (6.74 g, 25 mmol) was fed, 6.96 g (35 mmol) of 2-phenol was added, and the mixture was reacted at 160° C. for 6 hours under reflux conditions. The obtained product was dried under reduced pressure, and recrystallization was carried out twice using acetonitrile, followed by filtration to obtain brown crystals. The obtained crystals were dried under reduced pressure for 24 hours to obtain 2.46 g of Ph-TDP (bis(3-phenyl-4-hydroxyphenyl)tellurium).

As a result of measuring the molecular weight of the obtained compound (Ph-TDP) by the above measurement method (LC-MS), it was 466.

The following peaks were found by NMR measurement performed on the obtained compound (Ph-TDP) under the above measurement conditions, and the compound was confirmed to have a chemical structure of the compound (Ph-TDP) shown below.

δ (ppm) 6.8-7.7 (16H, Ph-H), 9.8 (2H, —OH)

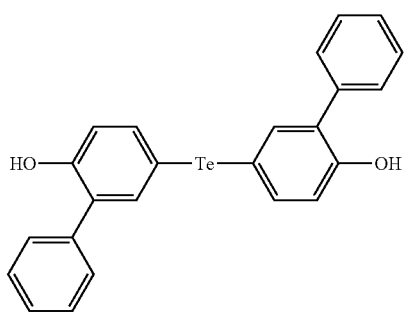

Compound (Ph-TDP)

(Synthesis Example 8) Synthesis of Compound (Ph-BHPT-ADBAC)

The same operations as in Synthesis Example 2 were performed except that 5.4 g (10 mmol) of the compound (Ph-BHPT) was used in place of 3.9 g (10 mmol) of the compound (BHPT), to obtain 1.28 g of a compound (Ph-BHPT-ADBAC) having a structure shown below.

As a result of measuring the molecular weight of the obtained compound (Ph-BHPT-ADBAC) by the above measurement method (LC-MS), it was 537.

The following peaks were found by NMR measurement performed on the obtained compound (Ph-BHPT-ADBAC) under the above measurement conditions, and the compound was confirmed to have a chemical structure of the compound (BHPT-ADBAC) shown below.

δ (ppm) 7.1-7.7 (16H, Ph-H), 5.0 (4H, O—CH$_2$—C(=O)—), 1.0-2.6 (34H, C—H/Adamantane of methylene and methine)

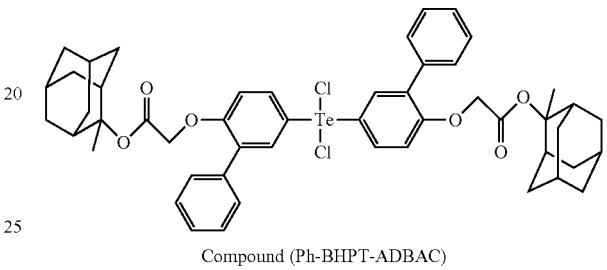

Compound (Ph-BHPT-ADBAC)

(Synthesis Example 9) Synthesis of Compound (TDP-ADBAC)

The same operations as in Synthesis Example 2 were performed except that 3.2 g (10 mmol) of the compound (TDP) was used in place of 3.9 g (10 mmol) of the compound (BHPT), to obtain 1.46 g of a compound (TDP-ADBAC) having a structure shown below.

As a result of measuring the molecular weight of the obtained compound (TDP-ADBAC) by the above measurement method (LC-MS), it was 726.

The following peaks were found by NMR measurement performed on the obtained compound (TDP-ADBAC) under the above measurement conditions, and the compound was confirmed to have a chemical structure of the compound (TDP-ADBAC) shown below.

δ (ppm) 7.0-7.4 (8H, Ph-H), 5.0 (4H, O—CH$_2$—C(=O)—), 1.0-2.6 (34H, C—H/Adamantane of methylene and methine)

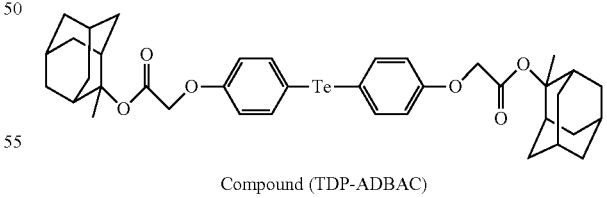

Compound (TDP-ADBAC)

(Synthesis Example 10) Synthesis of Compound (Ph-TDP-ADBAC)

The same operations as in Synthesis Example 2 were performed except that 4.7 g (10 mmol) of the compound (Ph-TDP) was used in place of 3.9 g (10 mmol) of the compound (BHPT), to obtain 1.70 g of a compound (Ph-TDP-ADBAC) having a structure shown below.

As a result of measuring the molecular weight of the obtained compound (Ph-TDP-ADBAC) by the above measurement method (LC-MS), it was 879.

The following peaks were found by NMR measurement performed on the obtained compound (Ph-TDP-ADBAC) under the above measurement conditions, and the compound was confirmed to have a chemical structure of the compound (Ph-TDP-ADBAC) shown below.

δ (ppm) 7.1-7.7 (16H, Ph-H), 5.0 (4H, O—CH$_2$—C(=O)—), 1.0-2.6 (34H, C—H/Adamantane of methylene and methine)

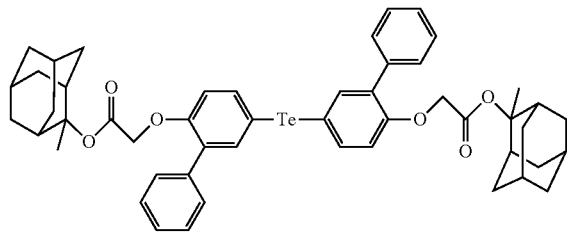

Compound (Ph-TDP-ADBAC)

(Synthesis Example 11) Synthesis of Compound (Ph-TDP-BOC)

The same operations as in Synthesis Example 3 were performed except that 4.7 g (10 mmol) of the compound (Ph-TDP) was used in place of 3.9 g (10 mmol) of the compound (BHPT), to obtain 1.14 g of a compound (Ph-TDP-BOC) having a structure shown below.

As a result of measuring the molecular weight of the obtained compound (Ph-TDP-BOC) by the above measurement method (LC-MS), it was 666.

The following peaks were found by NMR measurement performed on the obtained compound (Ph-TDP-BOC) under the above measurement conditions, and the compound was confirmed to have a chemical structure of the compound (Ph-TDP-BOC) shown below.

δ (ppm) 7.3-7.7 (8H, Ph-H), 1.4 (18H, C—CH$_3$)

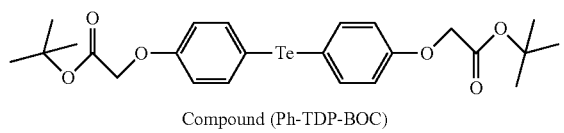

Compound (Ph-TDP-BOC)

(Synthesis Example 12) Synthesis of Compound (Ph-TDP-EE)

The same operations as in Synthesis Example 3 were performed except that 4.7 g (10 mmol) of the compound (Ph-TDP) was used in place of 3.9 g (10 mmol) of the compound (BHPT), to obtain 1.16 g of a compound (Ph-TDP-EE) having a structure shown below.

As a result of measuring the molecular weight of the obtained compound (Ph-TDP-EE) by the above measurement method (LC-MS), it was 610.

The following peaks were found by NMR measurement performed on the obtained compound (Ph-TDP-EE) under the above measurement conditions, and the compound was confirmed to have a chemical structure of the compound (Ph-TDP-EE) shown below.

δ (ppm) 7.1-7.7 (16H, Ph-H), 5.6 (2H, CH), 1.6 (6H, —CH$_3$), 3.9 (4H, O—CH$_2$—), 1.2 (6H, —CH$_3$)

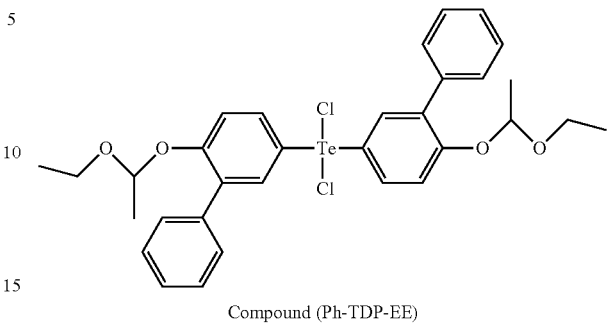

Compound (Ph-TDP-EE)

(Synthesis Example 13) Synthesis of R1-BHPT

To a container (internal capacity: 100 ml) equipped with a stirrer, a condenser tube, and a burette, 8.1 g (21 mmol) of the compound (BHPT), 0.7 g (42 mmol) of paraformaldehyde, 50 ml of glacial acetic acid, and 50 ml of PGME were fed, 8 ml of 95% sulfuric acid was added, and the reaction solution was stirred at 100° C. for 6 hours and reacted. Next, the reaction solution was concentrated. The reaction product was precipitated by the addition of 1000 ml of methanol. After cooling to room temperature, the precipitates were separated by filtration. The obtained solid matter was subjected to filtration, dried, and then separated and purified by column chromatography to obtain 5.6 g of the objective resin (R1-BHPT) having a structure represented by the following formula.

As a result of measuring the molecular weight in terms of polystyrene of the obtained resin (R1-BHPT) by the above method, it was Mn: 587, Mw: 1216, Mw/Mn: 2.07.

The following peaks were found by NMR measurement performed on the obtained resin(R1-BHPT) under the above measurement conditions, and the resin was confirmed to have a chemical structure of the following formula (R1-BHPT).

δ (ppm) 10.2 (2H, —OH), 6.8-7.8 (8H, Ph-H), 4.1 (2H, —CH$_2$)

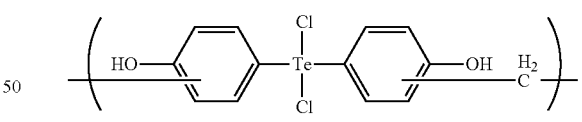

Resin (R1-BHPT)

(Synthesis Example 14) Synthesis of R2-BHPT

The same operations as in Synthesis Example 13 were performed except that 7.6 g (42 mmol) of 4-biphenylcarboxaldehyde (manufactured by Mitsubishi Gas Chemical Company Inc.) was used in place of 0.7 g (42 mmol) of paraformaldehyde, to obtain 5.7 g of the objective resin (R2-BHPT) having a structure represented by the following formula.

As a result of measuring the molecular weight in terms of polystyrene of the obtained resin (R2-BHPT) by the above method, it was Mn: 405, Mw: 880, Mw/Mn: 2.17.

The following peaks were found by NMR measurement performed on the obtained resin (R2-BHPT) under the above measurement conditions, and the resin was confirmed to have a chemical structure of the following formula (R2-BHPT).

δ (ppm) 10.2 (2H, —OH), 6.8-7.8 (17H, Ph-H), 4.5 (1H, —CH)

Moreover, the solubility of the obtained resin (R2-BHPT) in a safe solvent was evaluated by the above method. The results are shown in Table 1.

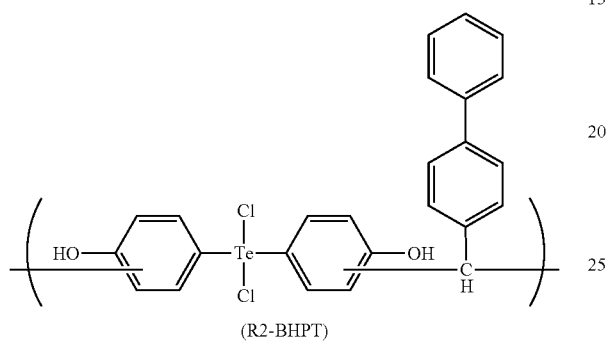

(R2-BHPT)

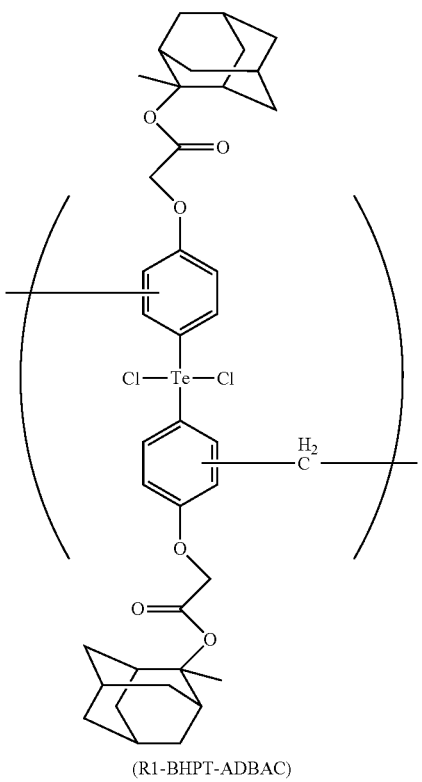

(R1-BHPT-ADBAC)

(Synthesis Example 15) Synthesis of R1-BHPT-ADBAC

The same operations as in Synthesis Example 13 were performed except that 16.8 g of the compound (BHPT-ADBAC) was used in place of 8.1 g (21 mmol) of the compound (BHPT), to obtain 5.0 g of the objective resin (R1-BHPT-ADBAC) having a structure represented by the following formula.

As a result of measuring the molecular weight in terms of polystyrene of the obtained resin (R1-BHPT-ADBAC) by the above method, it was Mn: 1045, Mw: 2330, Mw/Mn: 2.23.

The following peaks were found by NMR measurement performed on the obtained resin (R1-BHPT-ADBAC) under the above measurement conditions, and the resin was confirmed to have a chemical structure of the following formula (R1-BHPT-ADBAC).

δ (ppm) 6.8-8.1 (8H, Ph-H), 4.7-5.0 (4H, O—CH$_2$—C(=O)—), 1.2-2.7 (34H, C—H/Adamantane of methylene and methine), 4.1 (2H, —CH$_2$)

(Synthesis Example 16) Synthesis of R2-BHPT-ADBAC

The same operations as in Synthesis Example 15 were performed except that 7.6 g (42 mmol) of 4-biphenylcarboxaldehyde (manufactured by Mitsubishi Gas Chemical Company Inc.) was used in place of 0.7 g (42 mmol) of paraformaldehyde, to obtain 10.4 g of the objective resin (R2-BHPT-ADBAC) having a structure represented by the following formula.

As a result of measuring the molecular weight in terms of polystyrene of the obtained resin (R2-BHPT-ADBAC) by the above method, it was Mn: 840, Mw: 1819, Mw/Mn: 2.16.

The following peaks were found by NMR measurement performed on the obtained resin (R2-BHPT-ADBAC) under the above measurement conditions, and the resin was confirmed to have a chemical structure of the following formula (R2-BHPT-ADBAC).

δ (ppm) 6.8-8.1 (17H, Ph-H), 4.7-5.0 (4H, O—CH$_2$—C(=O)—), 1.2-2.7 (34H, C—H/Adamantane of methylene and methine), 4.5 (1H, —CH)

Moreover, the solubility of the obtained resin (R2-BHPT-ADBAC) in a safe solvent was evaluated by the above method. The results are shown in Table 1.

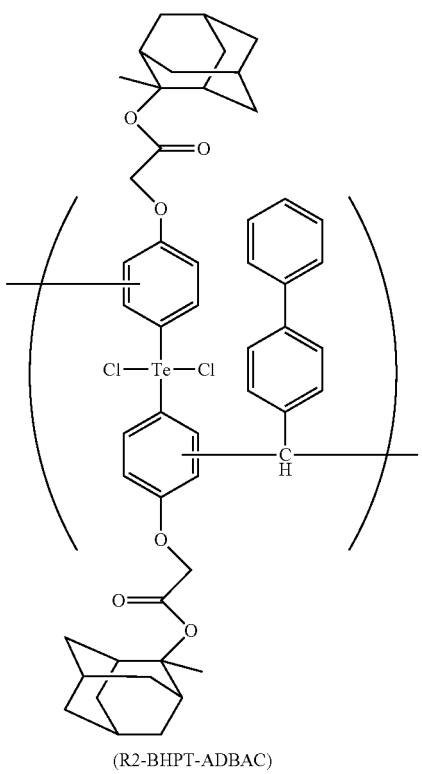

(R2-BHPT-ADBAC)

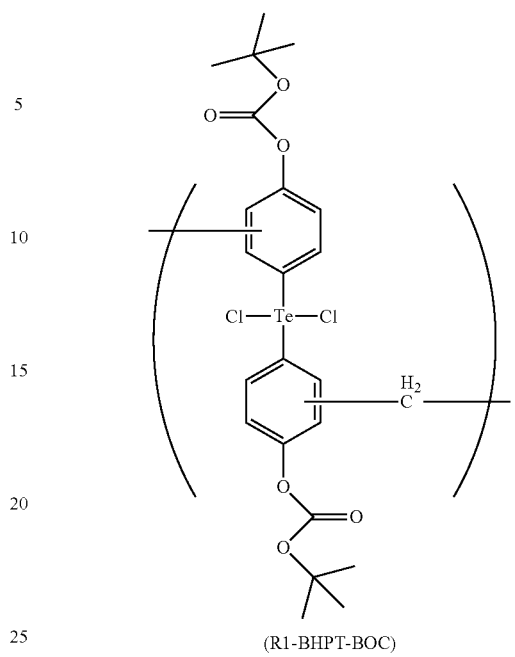

(R1-BHPT-BOC)

(Synthesis Example 17) Synthesis of R1-BHPT-BOC

The same operations as in Synthesis Example 13 were performed except that 12.3 g of the compound (BHPT-BOC) was used in place of 8.1 g (21 mmol) of the compound (BHPT), to obtain 7.6 g of the objective resin (R1-BHPT-BOC) having a structure represented by the following formula.

As a result of measuring the molecular weight in terms of polystyrene of the obtained resin (R1-BHPT-BOC) by the above method, it was Mn: 768, Mw: 1846, Mw/Mn: 2.40.

The following peaks were found by NMR measurement performed on the obtained resin (R1-BHPT-BOC) under the above measurement conditions, and the resin was confirmed to have a chemical structure of the following formula (R1-BHPT-BOC).

δ (ppm) 7.1-7.3 (8H, Ph-H), 1.4 (18H, C—C$\underline{H}_3$), 4.1 (2H, —C$H_2$)

(Synthesis Example 18) Synthesis of R2-BHPT-BOC

The same operations as in Synthesis Example 17 were performed except that 7.6 g (42 mmol) of 4-biphenylcarboxaldehyde (manufactured by Mitsubishi Gas Chemical Company Inc.) was used in place of 0.7 g (42 mmol) of paraformaldehyde, to obtain 3.7 g of the objective resin (R2-BHPT-BOC) having a structure represented by the following formula.

As a result of measuring the molecular weight in terms of polystyrene of the obtained resin (R2-BHPT-BOC) by the above method, it was Mn: 620, Mw: 1336, Mw/Mn: 2.15.

The following peaks were found by NMR measurement performed on the obtained resin (R2-BHPT-BOC) under the above measurement conditions, and the resin was confirmed to have a chemical structure of the following formula (R2-BHPT-BOC).

δ (ppm) 7.1-7.3 (17H, Ph-H), 1.4 (18H, C—C$\underline{H}_3$), 4.5 (1H, —CH)

121

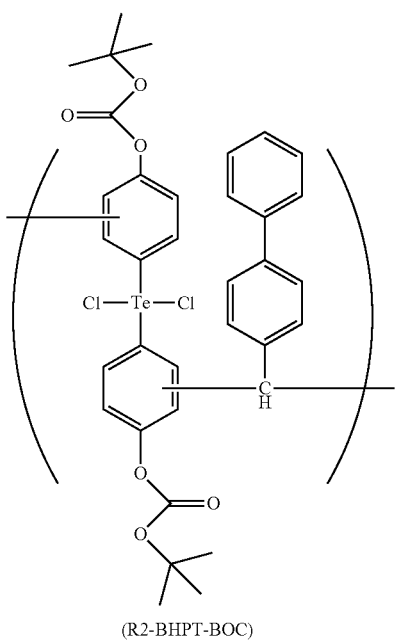

(R2-BHPT-BOC)

122

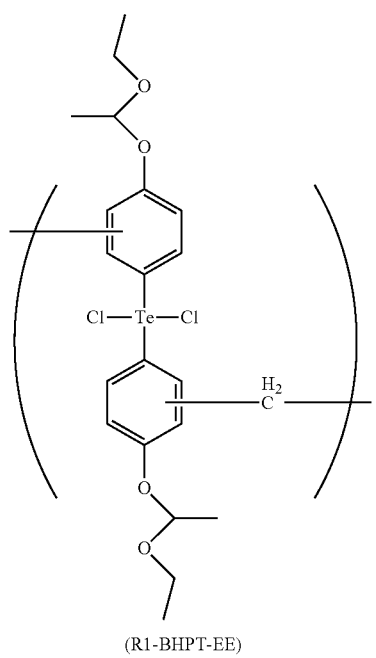

(R1-BHPT-EE)

(Synthesis Example 19) Synthesis of R1-BHPT-EE

The same operations as in Synthesis Example 13 were performed except that 11.1 g of the compound (BHPT-EE) was used in place of 8.1 g (21 mmol) of the compound (BHPT), to obtain 7.8 g of the objective resin (R1-BHPT-EE) having a structure represented by the following formula.

As a result of measuring the molecular weight in terms of polystyrene of the obtained resin (R1-BHPT-EE) by the above method, it was Mn: 694, Mw: 1548, Mw/Mn: 2.23.

The following peaks were found by NMR measurement performed on the obtained resin (R1-BHPT-EE) under the above measurement conditions, and the resin was confirmed to have a chemical structure of the following formula (R1-BHPT-EE).

δ (ppm) 6.9-7.4 (8H, Ph-H), 5.6 (2H, C$\underline{H}$), 1.6 (6H, —C$\underline{H}_3$), 3.9 (4H, O—C$\underline{H}_2$—), 1.2 (6H, —C$\underline{H}_3$), 4.1 (2H, —C$\underline{H}_2$)

(Synthesis Example 20) Synthesis of R2-BHPT-EE

The same operations as in Synthesis Example 19 were performed except that 7.6 g (42 mmol) of 4-biphenylcarboxaldehyde (manufactured by Mitsubishi Gas Chemical Company Inc.) was used in place of 0.7 g (42 mmol) of paraformaldehyde, to obtain 3.6 g of the objective resin (R2-BHPT-EE) having a structure represented by the following formula.

As a result of measuring the molecular weight in terms of polystyrene of the obtained resin (R2-BHPT-EE) by the above method, it was Mn: 610, Mw: 1208, Mw/Mn: 1.98.

The following peaks were found by NMR measurement performed on the obtained resin (R2-BHPT-EE) under the above measurement conditions, and the resin was confirmed to have a chemical structure of the following formula (R2-BHPT-EE).

δ (ppm) 6.9-7.4 (17H, Ph-H), 5.6 (2H, C$\underline{H}$), 1.6 (6H, —C$\underline{H}_3$), 3.9 (4H, O—C$\underline{H}_2$—), 1.2 (6H, —C$\underline{H}_3$), 4.5 (1H, —C$\underline{H}$)

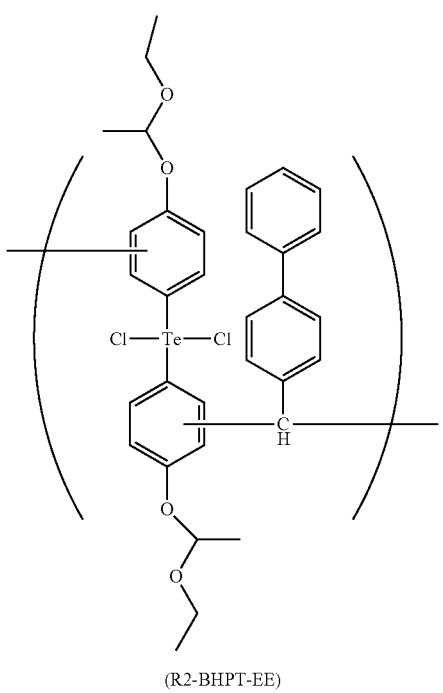

(R2-BHPT-EE)

(Synthesis Example 21) Synthesis of R1-Ph-BHPT

The same operations as in Synthesis Example 13 were performed except that 11.3 g of the compound (Ph-BHPT) was used in place of 8.1 g (21 mmol) of the compound (BHPT), to obtain 7.0 g of the objective resin (R1-Ph-BHPT) having a structure represented by the following formula.

As a result of measuring the molecular weight in terms of polystyrene of the obtained resin (R1-Ph-BHPT) by the above method, it was Mn: 764, Mw: 1695, Mw/Mn: 2.22.

The following peaks were found by NMR measurement performed on the obtained resin (R1-Ph-BHPT) under the above measurement conditions, and the resin was confirmed to have a chemical structure of the following formula (R1-Ph-BHPT).

δ (ppm) 9.0 (2H, —OH), 7.0-7.5 (16H, Ph-H), 4.1 (2H, —CH$_2$)

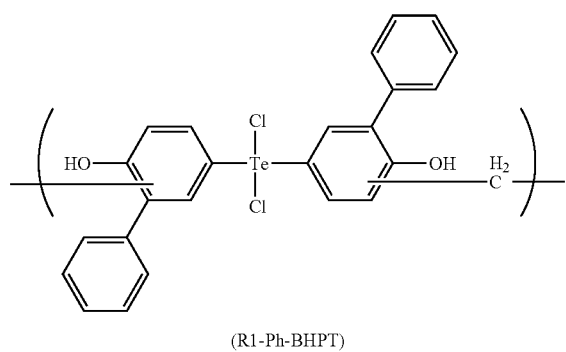

(R1-Ph-BHPT)

(Synthesis Example 22) Synthesis of R2-Ph-BHPT

The same operations as in Synthesis Example 21 were performed except that 7.6 g (42 mmol) of 4-biphenylcarboxaldehyde (manufactured by Mitsubishi Gas Chemical Company Inc.) was used in place of 0.7 g (42 mmol) of paraformaldehyde, to obtain 3.4 g of the objective resin (R2-Ph-BHPT) having a structure represented by the following formula.

As a result of measuring the molecular weight in terms of polystyrene of the obtained resin (R2-Ph-BHPT) by the above method, it was Mn: 672, Mw: 1345, Mw/Mn: 2.00.

The following peaks were found by NMR measurement performed on the obtained resin (R2-Ph-BHPT) under the above measurement conditions, and the resin was confirmed to have a chemical structure of the following formula (R2-Ph-BHPT).

δ (ppm) 9.0 (2H, —OH), 7.0-7.5 (25H, Ph-H), 4.5 (1H, —CH)

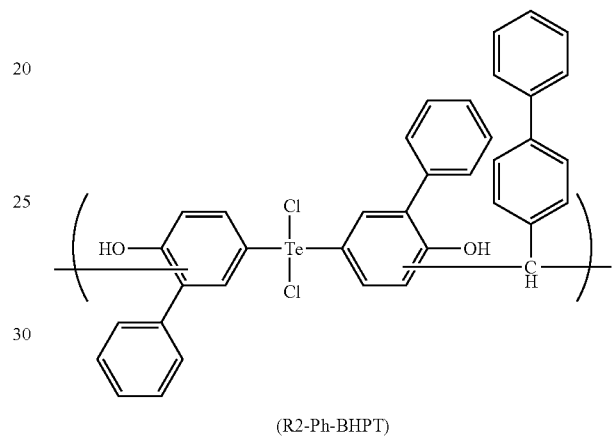

(R2-Ph-BHPT)

(Synthesis Example 23) Synthesis of R1-TDP

The same operations as in Synthesis Example 13 were performed except that 6.6 g of the compound (TDP) was used in place of 8.1 g (21 mmol) of the compound (BHPT), to obtain 4.6 g of the objective resin (R1-TDP) having a structure represented by the following formula.

As a result of measuring the molecular weight in terms of polystyrene of the obtained resin (R1-TDP) by the above method, it was Mn: 449, Mw: 995, Mw/Mn: 2.22.

The following peaks were found by NMR measurement performed on the obtained resin (R1-TDP) under the above measurement conditions, and the resin was confirmed to have a chemical structure of the following formula (R1-TDP).

δ (ppm) 6.8-7.7 (8H, Ph-H), 9.8 (2H, —OH), 4.1 (2H, —CH$_2$)

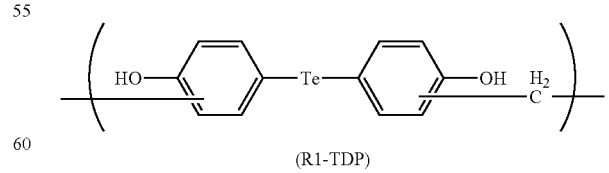

(R1-TDP)

(Synthesis Example 24) Synthesis of R2-TDP

The same operations as in Synthesis Example 21 were performed except that 7.6 g (42 mmol) of 4-biphenylcarboxaldehyde (manufactured by Mitsubishi Gas Chemical Company Inc.) was used in place of 0.7 g (42 mmol) of paraformaldehyde, to obtain 2.0 g of the objective resin (R2-TDP) having a structure represented by the following formula.

As a result of measuring the molecular weight in terms of polystyrene of the obtained resin (R2-TDP) by the above method, it was Mn: 414, Mw: 922, Mw/Mn: 2.23.

The following peaks were found by NMR measurement performed on the obtained resin (R2-TDP) under the above measurement conditions, and the resin was confirmed to have a chemical structure of the following formula (R2-TDP).

δ (ppm) 6.8-7.7 (17H, Ph-H), 9.8 (2H, —OH), 4.5 (1H, —CH)

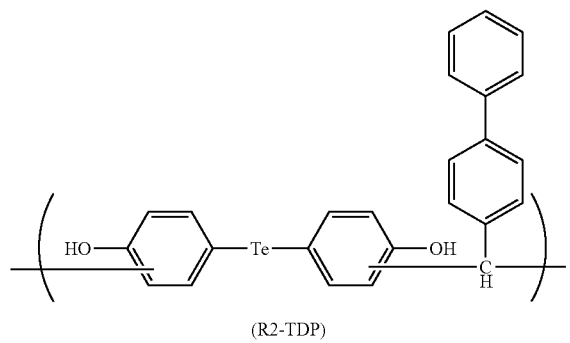

(R2-TDP)

(Synthesis Example 25) Synthesis of R1-Ph-TDP

The same operations as in Synthesis Example 13 were performed except that 9.8 g of the compound (Ph-TDP) was used in place of 8.1 g (21 mmol) of the compound (BHPT), to obtain 6.9 g of the objective compound resin (R1-Ph-TDP) having a structure represented by the following formula.

As a result of measuring the molecular weight in terms of polystyrene of the obtained resin (R1-Ph-TDP) by the above method, it was Mn: 665, Mw: 1474, Mw/Mn: 2.22.

The following peaks were found by NMR measurement performed on the obtained compound resin (R1-Ph-TDP) under the above measurement conditions, and the resin was confirmed to have a chemical structure of the following formula (R1-Ph-TDP).

δ (ppm) 6.8-7.7 (16H, Ph-H), 9.8 (2H, —OH), 4.1 (2H, —CH$_2$)

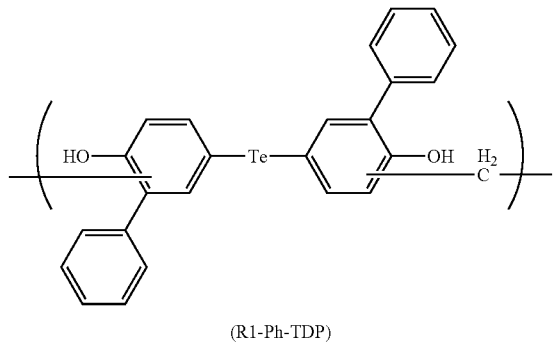

(R1-Ph-TDP)

(Synthesis Example 26) Synthesis of R2-Ph-TDP

The same operations as in Synthesis Example 21 were performed except that 7.6 g (42 mmol) of 4-biphenylcarboxaldehyde (manufactured by Mitsubishi Gas Chemical Company Inc.) was used in place of 0.7 g (42 mmol) of paraformaldehyde, to obtain 3.2 g of the objective resin (R2-Ph-TDP) having a structure represented by the following formula.

As a result of measuring the molecular weight in terms of polystyrene of the obtained resin (R2-Ph-TDP) by the above method, it was Mn: 608, Mw: 1395, Mw/Mn: 2.29.

The following peaks were found by NMR measurement performed on the obtained resin (R2-Ph-TDP) under the above measurement conditions, and the resin was confirmed to have a chemical structure of the following formula (R2-Ph-TDP).

δ (ppm) 6.8-7.7 (25H, Ph-H), 9.8 (2H, —OH), 4.5 (1H, —CH)

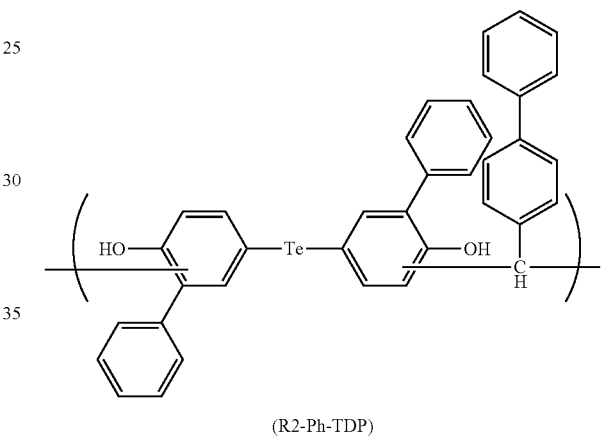

(R2-Ph-TDP)

(Synthesis Example 27) Synthesis of R1-Ph-BHPT-ADBAC

The same operations as in Synthesis Example 13 were performed except that 20.0 g of the compound (Ph-BHPT-ADBAC) was used in place of 8.1 g (21 mmol) of the compound (BHPT), to obtain 5.0 g of the objective resin (R1-Ph-BHPT-ADBAC) having a structure represented by the following formula.

As a result of measuring the molecular weight in terms of polystyrene of the obtained resin (R1-Ph-BHPT-ADBAC) by the above method, it was Mn: 1045, Mw: 2330, Mw/Mn: 2.23.

The following peaks were found by NMR measurement performed on the obtained resin (R1-Ph-BHPT-ADBAC) under the above measurement conditions, and the resin was confirmed to have a chemical structure of the following formula (R1-Ph-BHPT-ADBAC).

δ (ppm) 6.8-8.1 (8H, Ph-H), 4.7-5.0 (4H, O—CH$_2$—C(=O)—), 1.2-2.7 (34H, C—H/Adamantane of methylene and methine), 4.1 (2H, —CH$_2$)

127

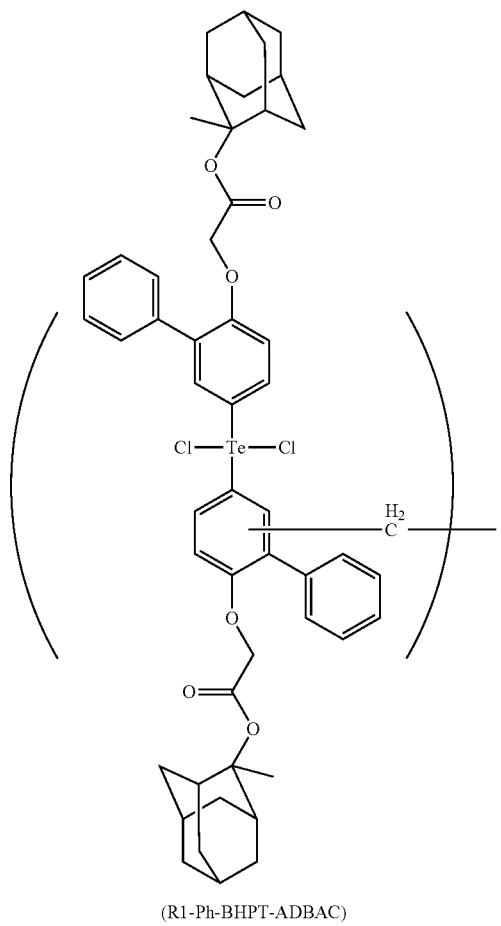

(R1-Ph-BHPT-ADBAC)

128

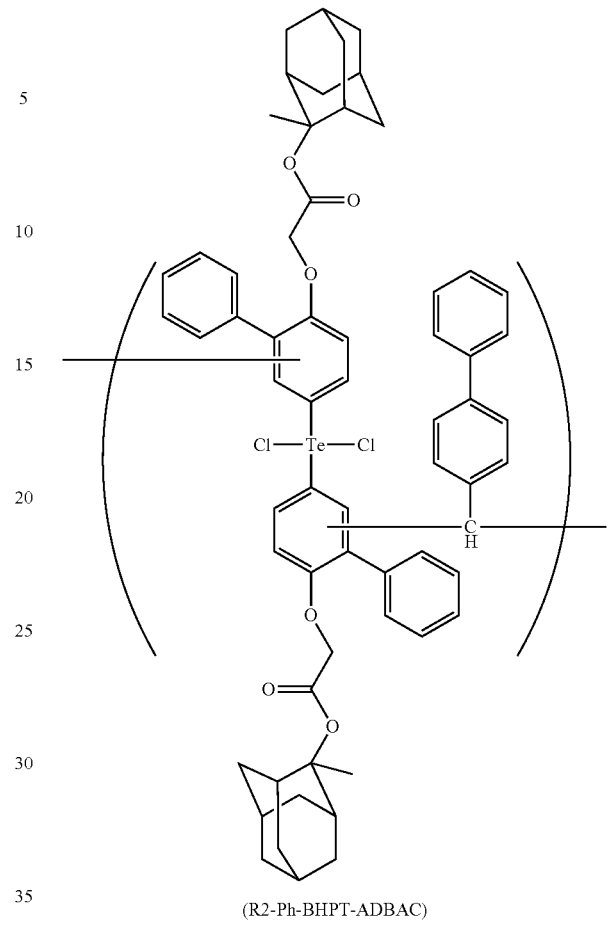

(R2-Ph-BHPT-ADBAC)

(Synthesis Example 28) Synthesis of R2-Ph-BHPT-ADBAC

The same operations as in Synthesis Example 23 were performed except that 7.6 g (42 mmol) of 4-biphenylcarboxaldehyde (manufactured by Mitsubishi Gas Chemical Company Inc.) was used in place of 0.7 g (42 mmol) of paraformaldehyde, to obtain 6.0 g of the objective resin (R2-Ph-BHPT-ADBAC) having a structure represented by the following formula.

As a result of measuring the molecular weight in terms of polystyrene of the obtained resin (R2-Ph-BHPT-ADBAC) by the above method, it was Mn: 1188, Mw: 2394, Mw/Mn: 2.02.

The following peaks were found by NMR measurement performed on the obtained resin (R2-Ph-BHPT-ADBAC) under the above measurement conditions, and the resin was confirmed to have a chemical structure of the following formula (R2-Ph-BHPT-ADBAC).

δ (ppm) 7.1-7.7 (25H, Ph-H), 5.0 (4H, O—CH2-C(=O)—), 1.0-2.6 (34H, C—H/Adamantane of methylene and methine), 4.5 (1H, —CH)

(Synthesis Example 29) Synthesis of R1-TDP-ADBAC

The same operations as in Synthesis Example 13 were performed except that 15.3 g of the compound (Ph-TDP-ADBAC) was used in place of 8.1 g (21 mmol) of the compound (BHPT), to obtain 11.4 g of the objective resin (R1-TDP-ADBAC) having a structure represented by the following formula.

As a result of measuring the molecular weight in terms of polystyrene of the obtained resin (R1-TDP-ADBAC) by the above method, it was Mn: 954, Mw: 2148, Mw/Mn: 2.25.

The following peaks were found by NMR measurement performed on the obtained resin (R1-TDP-ADBAC) under the above measurement conditions, and the resin was confirmed to have a chemical structure of the following formula (R1-TDP-ADBAC).

δ (ppm) 7.0-7.4 (8H, Ph-H), 5.0 (4H, O—CH2-C(=O)—), 1.0-2.6 (34H, C—H/Adamantane of methylene and methine), 4.1 (2H, —CH2)

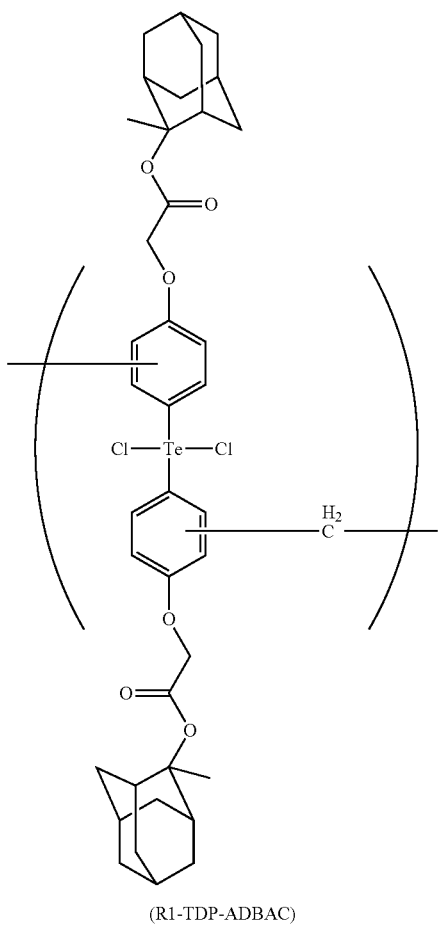

(R1-TDP-ADBAC)

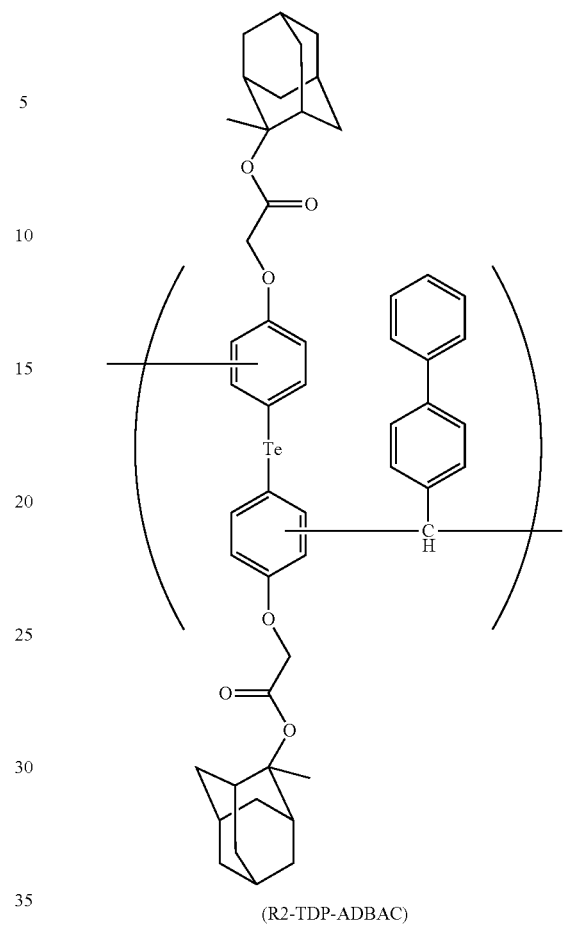

(R2-TDP-ADBAC)

(Synthesis Example 30) Synthesis of R2-TDP-ADBAC

The same operations as in Synthesis Example 23 were performed except that 7.6 g (42 mmol) of 4-biphenylcarboxaldehyde (manufactured by Mitsubishi Gas Chemical Company Inc.) was used in place of 0.7 g (42 mmol) of paraformaldehyde, to obtain 4.6 g of the objective resin (R2-TDP-ADBAC) having a structure represented by the following formula.

As a result of measuring the molecular weight in terms of polystyrene of the obtained resin (R2-TDP-ADBAC) by the above method, it was Mn: 910, Mw: 1805, Mw/Mn: 1.98.

The following peaks were found by NMR measurement performed on the obtained resin (R2-TDP-ADBAC) under the above measurement conditions, and the resin was confirmed to have a chemical structure of the following formula (R2-TDP-ADBAC).

δ (ppm) 7.0-7.4 (17H, Ph-H), 5.0 (4H, O—CH2-C(=O)—), 1.0-2.6 (34H, C—H/Adamantane of methylene and methine), 4.5 (1H, —CH)

(Synthesis Example 31) Synthesis of R1-Ph-TDP-ADBAC

The same operations as in Synthesis Example 13 were performed except that 18.5 g of the compound (Ph-TDP-ADBAC) was used in place of 8.1 g (21 mmol) of the compound (BHPT), to obtain 12.0 g of the objective resin (R1-Ph-TDP-ADBAC) having a structure represented by the following formula.

As a result of measuring the molecular weight in terms of polystyrene of the obtained resin (R1-Ph-TDP-ADBAC) by the above method, it was Mn: 1152, Mw: 2570, Mw/Mn: 2.23.

The following peaks were found by NMR measurement performed on the obtained resin (R1-Ph-TDP-ADBAC) under the above measurement conditions, and the resin was confirmed to have a chemical structure of the following formula (R1-Ph-TDP-ADBAC).

δ (ppm) 7.1-7.7 (16H, Ph-H), 5.0 (4H, O—CH$_2$—C(=O)—), 1.0-2.6 (34H, C—H/Adamantane of methylene and methine), 4.1 (2H, —CH2)

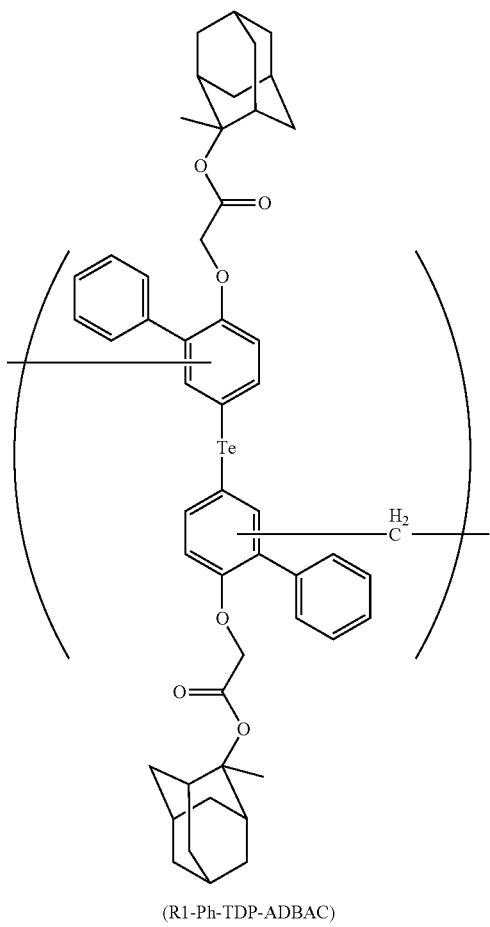

(R1-Ph-TDP-ADBAC)

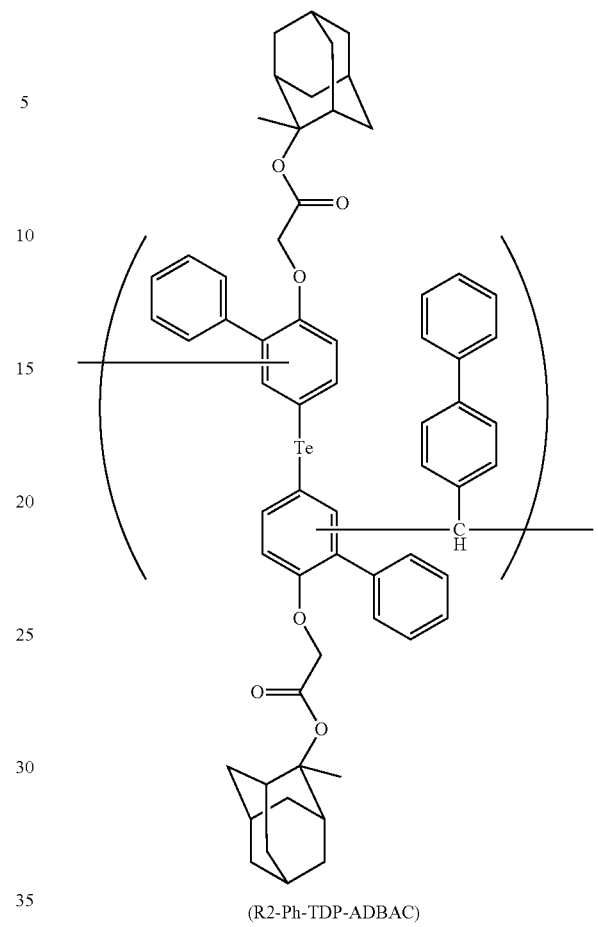

(R2-Ph-TDP-ADBAC)

(Synthesis Example 32) Synthesis of R2-Ph-TDP-ADBAC

The same operations as in Synthesis Example 23 were performed except that 7.6 g (42 mmol) of 4-biphenylcarboxaldehyde (manufactured by Mitsubishi Gas Chemical Company Inc.) was used in place of 0.7 g (42 mmol) of paraformaldehyde, to obtain 5.6 g of the objective resin (R2-Ph-TDP-ADBAC) having a structure represented by the following formula.

As a result of measuring the molecular weight in terms of polystyrene of the obtained resin (R2-Ph-TDP-ADBAC) by the above method, it was Mn: 1100, Mw: 2205, Mw/Mn: 2.004.

The following peaks were found by NMR measurement performed on the obtained resin (R2-Ph-TDP-ADBAC) under the above measurement conditions, and the resin was confirmed to have a chemical structure of the following formula (R2-Ph-TDP-ADBAC).

δ (ppm) 7.1-7.7 (25H, Ph-H), 5.0 (4H, O—$CH_2$—C(=O)—), 1.0-2.6 (34H, C—H/Adamantane of methylene and methine), 4.5 (1H, —CH)

(Synthesis Example 33) Synthesis of Resin (BHPT-Co-ADTBA)

In a 100 mL container, 0.58 g (1.5 mmol) of the compound (BHPT) was placed, 0.05 g (0.15 mmol) of tetrabutyl ammonium bromide, 0.28 g (2 mmol) of potassium carbonate, and 2 ml of N-methylpyrrolidone were added, and the mixture was stirred at 80° C. for 2 hours. Next, 0.547 g (1.0 mmol) of ADTBA (1,3,5-adamantane tribromoacetate) was dissolved in 1 ml of N-methylpyrrolidone, and the solution was reacted at 80° C. for 48 hours. The obtained reaction product was dropped to 1 N HCl to obtain brown crystals. The crystals were filtered and then dried under reduced pressure to obtain 0.40 g of the objective resin (BHPT-co-ADTBA).

As a result of measuring the molecular weight in terms of polystyrene of the obtained resin (BHPT-co-ADTBA) by the above method, it was Mn: 750, Mw: 1350, Mw/Mn: 1.80.

The following peaks were found by NMR measurement performed on the obtained resin (BHPT-co-ADBAC) under the above measurement conditions, and the resin was confirmed to have a chemical structure of the following formula (BHPT-co-ADBAC).

δ (ppm) 6.9-7.4 (4H, Ph-H), 4.6 (4H, —O—$CH_2$—CO—), 4.3 (2H, —$CH_2$—Br), 1.2-3.4 (13H, C—H/Adamantane of methylene and methine)

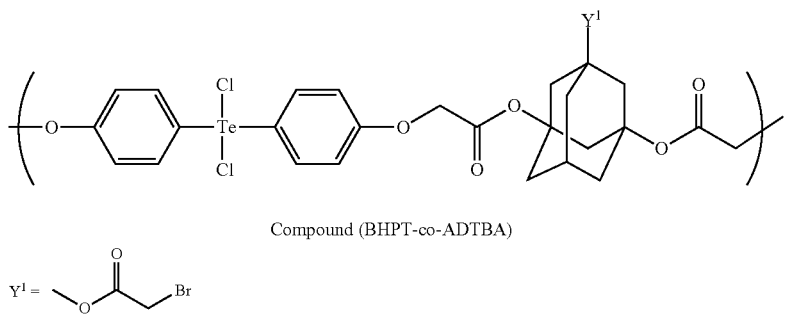

Compound (BHPT-co-ADTBA)

Y¹ = (structure: —O—C(=O)—CH₂—Br)

(Synthesis Example 34) Synthesis of Resin (TDP-co-ADTBA)

The same operations as in Synthesis Example 33 were performed except that 0.47 g of the compound (TDP) was used in place of 0.58 g (1.5 mmol) of the compound (BHPT), to obtain 0.36 g of the objective resin (TDP-co-ADTBA) having a structure represented by the following formula.

As a result of measuring the molecular weight in terms of polystyrene of the obtained resin (TDP-co-ADTBA) by the above method, it was Mn: 680, Mw: 1238, Mw/Mn: 1.82.

The following peaks were found by NMR measurement performed on the obtained resin (TDP-co-ADTBA) under the above measurement conditions, and the resin was confirmed to have a chemical structure of the following formula (TDP-co-ADTBA).

δ (ppm) 6.9-7.4 (4H, Ph-H), 4.6 (4H, —O—CH₂—CO—), 4.3 (2H, —CH₂—Br), 1.2-3.4 (13H, C—H/Adamantane of methylene and methine)

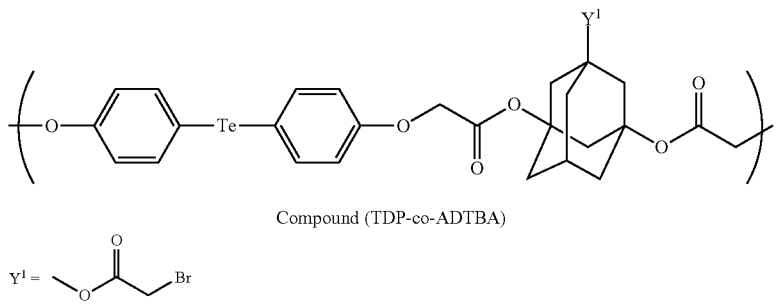

Compound (TDP-co-ADTBA)

Y¹ = (structure: —O—C(=O)—CH₂—Br)

(Synthesis Example 35) Synthesis of Resin (DMB-co-TeCl2-OH)

In a glove box, to a 100 ml container, 5.39 g (20 mmol) of tellurium tetrachloride was fed, 2.8 g (20 mmol) of 1,3-dimethoxybenzene, 5.9 g (44 mmol) of aluminum trichloride, and 20 ml of chloroform were added, and the mixture was reacted for 24 hours under ice cooling. The obtained product was dried under reduced pressure, and recrystallization was carried out twice using acetonitrile, followed by filtration. The obtained crystals were dried under reduced pressure for 24 hours to obtain 3.0 g of a resin (DMB-co-TeCl2).

As a result of measuring the molecular weight in terms of polystyrene of the obtained resin (DMB-co-TeCl2) by the above method, it was Mn: 39820, Mw: 62910, Mw/Mn: 1.58.

The following peaks were found by NMR measurement performed on the obtained resin (DMB-co-TeCl2) under the above measurement conditions, and the resin was confirmed to have a chemical structure of the following formula (DMB-co-TeCl2).

δ (ppm) 6.0-7.2 (2H, Ph-H), 3.6 (6H, —CH₃)

Moreover, the solubility of the obtained resin (DMB-co-TeCl2) in a safe solvent was evaluated by the above method. The results are shown in Table 1.

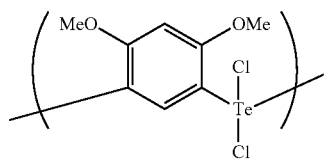

Resin (DMB-co-TeCl2)

Then, to a container (internal capacity: 100 mL) equipped with a stirrer, a condenser tube, and a burette, 0.78 g of the resin (DMB-co-TeCl2) and 15 ml of chloroform were added, 3.9 g (15.75 mmol) of boron tribromide was dropped, and the mixture was reacted at −20° C. for 48 hours. The solution after reaction was dropped to a 1.0N hydrochloric acid solution in an ice bath, and a black solid was recovered after filtration. The solid was dissolved in ethyl acetate, the solution was dehydrated by the addition of magnesium sulfate and then concentrated, and the residue was separated and purified by column chromatography to obtain 0.4 g of a resin (DMB-co-TeCl2-OH).

As a result of measuring the molecular weight in terms of polystyrene of the obtained resin (DMB-co-TeCl2-OH) by the above method, it was Mn: 39800, Mw: 62880, Mw/Mn: 1.58.

The following peaks were found by NMR measurement performed on the obtained resin (DMB-co-TeCl2-OH)

under the above measurement conditions, and the resin was confirmed to have a chemical structure of the resin (DMB-co-TeCl2-OH) shown below.

δ (ppm) 9.0 (2H, —OH), 6.4-7.0 (2H, Ph-H)

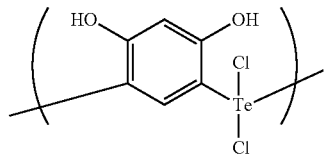

Resin (DMB-co-TeCl2-OH)

(Synthesis Example 36) Synthesis of Resin (Re-co-Te)

In a glove box, to a 100 mL container, tellurium tetrachloride (7.54 g, 28 mmol) was fed, 1.54 g (14 mmol) of resorcinol and 20 ml of carbon tetrachloride were added, and the mixture was reacted at 80° C. for 24 hours under reflux conditions. The obtained reaction solution was washed by the addition of dichloromethane and filtered, and the obtained solid was dried under reduced pressure.

Then, in a 300 ml container, 13.0 g (66 mmol) of sodium ascorbate was dissolved in 25 ml of water, the above solid dissolved in 60 ml of ethyl acetate was dropped to the solution, and the mixture was reacted at 25° C. for 24 hours. The solution after reaction was subjected to extraction with ethyl acetate 15 times, and the organic solvent was then distilled off to obtain a brown solid.

Further, in a container (internal capacity: 100 mL) equipped with a stirrer, a condenser tube, and a burette, the obtained brown solid was placed, 10 ml of ethyl acetate and 13.0 g (60 mmol) of copper powder were added, and the mixture was reacted at 80° C. for 24 hours under reflux conditions. The obtained reaction solution was concentrated 2-fold, the residue was dropped to chloroform, and the obtained precipitates were filtered and dried to obtain 0.2 g of a black-brown resin (Re-co-Te).

As a result of measuring the molecular weight in terms of polystyrene of the obtained resin (Re-co-Te) by the above method, it was Mn: 21500, Mw: 41500, Mw/Mn: 1.93.

The following peaks were found by NMR measurement performed on the obtained resin (Re-co-Te) under the above measurement conditions, and the resin was confirmed to have a chemical structure of the resin (Re-co-Te) shown below.

δ (ppm) 9.1 (2H, —OH), 6.1-7.0 (2H, Ph-H)

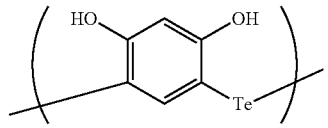

Resin (Re-co-Te)

(Synthesis Example 37) Synthesis of Resin (DMB-co-TeCl2-ADBAC)

In a container (internal capacity: 200 mL) equipped with a stirrer, a condenser tube, and a burette, 3.7 g of the resin (DMB-co-TeCl2-OH), 0.30 g (22 mmol) of potassium carbonate, and 6.3 g (22 mmol) of bromoacetic acid-2-methyladamantan-2-yl were dissolved in 50 ml of N-methylpyrrolidone, and the solution was stirred for 2 hours. After stirring, 5.7 g (22 mmol) of adamantane bromoacetate was further added thereto, and the mixture was reacted at 100° C. for 24 hours. After the reaction terminated, the reaction mixture was dropped to a 1 N aqueous hydrochloric acid solution, and the resulting black solid was filtered off and dried to obtain 5.3 g of the following resin (DMB-co-TeCl2-ADBAC).

The following peaks were found by NMR measurement performed on the obtained resin (DMB-co-TeCl2-ADBAC) under the above measurement conditions, and the resin was confirmed to have a chemical structure of the resin (DMB-co-TeCl2-ADBAC) shown below.

δ (ppm) 6.5-7.2 (2H, Ph-H), 4.9-5.0 (4H, —CH$_2$—), 1.0-2.6 (34H, C—H/Adamantane of methylene and methine

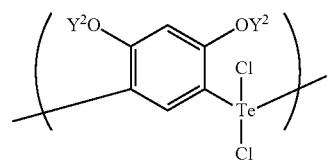

Compound (DMB-co-TeCl2-ADBAC)

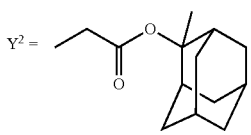

(Synthesis Example 38) Synthesis of Resin (Re-co-Te-ADBAC)

In a container (internal capacity: 200 mL) equipped with a stirrer, a condenser tube, and a burette, 2.7 g of the resin (Re-co-Te), 0.30 g (22 mmol) of potassium carbonate, and 0.64 g (2 mmol) of tetrabutyl ammonium bromide were dissolved in 50 ml of N-methylpyrrolidone, and the solution was stirred for 2 hours. After stirring, 6.3 g (22 mmol) of bromoacetic acid-2-methyladamantan-2-yl was further added thereto, and the mixture was reacted at 100° C. for 24 hours. After the reaction terminated, the reaction mixture was dropped to a 1 N aqueous hydrochloric acid solution, and the resulting black solid was filtered off and dried to obtain 4.6 g of the following resin (Re-co-Te-ADBAC).

The following peaks were found by NMR measurement performed on the obtained resin (Re-co-Te-ADBAC) under the above measurement conditions, and the resin was confirmed to have a chemical structure of the resin (Re-co-Te-ADBAC) shown below.

δ (ppm) 6.5-7.2 (2H, Ph-H), 4.9-5.0 (4H, —CH$_2$—), 1.0-2.6 (34H, C—H/Adamantane of methylene and methine

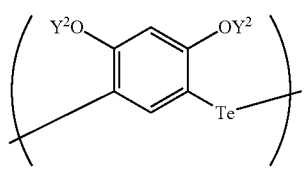

Compound (Re-co-Te-ADBAC)

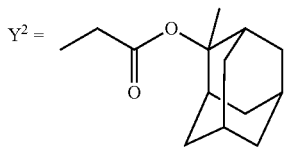

(Synthesis Example 39) Synthesis of Resin (DPE-co-Te)

In a glove box, to a 300 ml container, tellurium tetrachloride (75 g, 280 mmol) was fed, 100 ml of carbon tetrachloride and 15 g (140 mmol) of diphenyl ether were added, and the mixture was reacted at 80° C. for 24 hours under reflux conditions. The obtained reaction solution was washed by the addition of dichloromethane and filtered, and the obtained solid was dried under reduced pressure.

Then, in a 1000 ml container, 130 g (66 mmol) of sodium ascorbate was dissolved in 250 ml of water, the above solid dissolved in 120 ml of ethyl acetate was dropped to the solution, and the mixture was reacted at 25° C. for 24 hours. The solution after reaction was subjected to extraction with ethyl acetate 5 times, and the organic solvent was then distilled off to obtain a brown solid.

Further, in a container (internal capacity: 100 mL) equipped with a stirrer, a condenser tube, and a burette, the obtained brown solid was placed, 20 ml of ethyl acetate and 38.0 g (600 mmol) of copper powder were added, and the mixture was reacted at 80° C. for 24 hours under reflux conditions. The obtained reaction solution was concentrated 2-fold, the residue was dropped to hexane, and the obtained precipitates were filtered and dried to obtain 0.11 g of a red resin (DPE-co-Te).

As a result of measuring the molecular weight in terms of polystyrene of the obtained resin (DPE-co-Te) by the above method, it was Mn: 1280, Mw: 2406, Mw/Mn: 1.88.

The following peaks were found by NMR measurement performed on the obtained resin (DPE-co-Te) under the above measurement conditions, and the resin was confirmed to have a chemical structure of the resin (DPE-co-Te) shown below.

δ (ppm) 6.9-8.8 (8H, Ph-H)

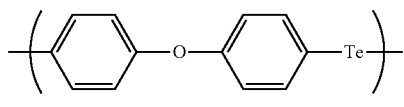

Resin (DPE-co-Te)

(Synthesis Example 40) Synthesis of Tellurium-Containing Core-Shell Type Hyperbranched Polymer To a 200 mL container, 3.2 g (25 mmol) of tellurium and 25 ml of THF were added and stirred for suspension, 30 ml of a methyllithium solution (1 mol/l, diethyl ether solution) was dropped under ice cooling, and the mixture was stirred at 0° C. for 1 hour. 6.1 g (40 mmol) of chloromethylstyrene was further added thereto, and the mixture was further reacted by being stirred at 25° C. for 2 hours. Next, the solvent in the reaction solution was distilled off, and the residue was dried under reduced pressure to obtain 2.0 g of methyltellanylstyrene.

To a 200 mL container, 3.2 g (25 mmol) of tellurium and 25 ml of THF were added and stirred for suspension, 30 ml of a methyllithium solution (1 mol/l, diethyl ether solution) was dropped under ice cooling, and the mixture was stirred at 0° C. for 1 hour. Next, 20 ml of a 0.5 mol/l aqueous ammonium chloride solution was added thereto, and the mixture was reacted by being stirred at 25° C. for 2 hours. After reaction, the aqueous layer was separated and subjected to extraction with diethyl ether three times. The solvent in the extracted organic layer was distilled off, and the residue was dried under reduced pressure to obtain 2.2 g of dimethyl ditelluride.

Further, to a container (internal capacity: 500 mL) equipped with a stirrer, a condenser tube, and a burette, 80 g of chlorobenzene, 2.6 g (10 mmol) of the above methyltellanylstyrene, 0.7 g (2.5 mmol) of the dimethyl ditelluride, and 0.4 g (2.5 mmol) of azobisisobutyronitrile were added, and the mixture was stirred at 110° C. for 1 hour in the current of nitrogen. After stirring, 90 g of benzene, 0.4 g of acrylic acid, and 4.35 g of t-butyl acrylate were added thereto, and the mixture was further reacted by being stirred at 110° C. for 5 hours. After the reaction terminated, 1500 ml of water was added to the reaction solution, and the mixture was filtered and dried to obtain 2.0 g of a tellurium-containing core-shell type hyperbranched polymer (referred to as "Te-containing hyperbranched polymer" in Table 1).

As a result of measuring the molecular weight in terms of polystyrene of the obtained tellurium-containing core-shell type hyperbranched polymer by the above method, it was Mn: 3260, Mw: 5800, Mw/Mn: 1.78.

(Comparative Synthesis Example 1) Synthesis of CR-1

A 4-neck flask (internal capacity: 10 L) equipped with a Dimroth condenser tube, a thermometer, and a stirring blade and having a detachable bottom was prepared. To this 4-neck flask, 1.09 kg (7 mol) of 1,5-dimethylnaphthalene (manufactured by Mitsubishi Gas Chemical Co., Inc.), 2.1 kg (28 mol as formaldehyde) of 40% by mass of an aqueous formalin solution (manufactured by Mitsubishi Gas Chemical Co., Inc.), and 0.97 mL of 98% by mass of sulfuric acid (manufactured by Kanto Chemical Co., Inc.) were fed in the current of nitrogen, and the mixture was reacted for 7 hours while being refluxed at 100° C. at normal pressure. Subsequently, 1.8 kg of ethylbenzene (a special grade reagent manufactured by Wako Pure Chemical Industries, Ltd.) was added as a diluting solvent to the reaction solution, and the mixture was left to stand still, followed by removal of an aqueous phase as a lower phase. Neutralization and washing with water were further performed, and ethylbenzene and unreacted 1,5-dimethylnaphthalene were distilled off under reduced pressure to obtain 1.25 kg of a dimethylnaphthalene formaldehyde resin as a light brown solid.

Then, a 4-neck flask (internal capacity: 0.5 L) equipped with a Dimroth condenser tube, a thermometer, and a stirring blade was prepared. To this 4-neck flask, 100 g (0.51 mol) of the dimethylnaphthalene formaldehyde resin obtained as described above and 0.05 g of p-toluenesulfonic acid were fed in the current of nitrogen, the temperature was elevated to 190° C., and the mixture was heated for 2 hours and then stirred. Subsequently, 52.0 g (0.36 mol) of 1-naphthol was further added thereto, the temperature was further elevated to 220° C., and the mixture was reacted for 2 hours. After dilution with a solvent, neutralization and washing with water were performed, and the solvent was distilled off under reduced pressure to obtain 126.1 g of a modified resin (CR-1) as a black-brown solid.

(Comparative Synthesis Example 2) Synthesis of CR-1-BOC

In a container (internal capacity: 200 mL) equipped with a stirrer, a condenser tube, and a burette, 10 g of the obtained compound (CR-1) and 5.5 g (25 mmol) of di-t-butyl dicarbonate (manufactured by Sigma-Aldrich) were fed to 100 mL of acetone, 3.45 g (25 mmol) of potassium carbonate (manufactured by Sigma-Aldrich) was added, and the contents were reacted by being stirred at 20° C. for 6 hours to obtain a reaction solution. Next, the reaction solution was concentrated, and the reaction product was precipitated by the addition of 100 g of pure water to the concentrate, cooled to room temperature, and then filtered to separate solid matter.

The obtained solid matter was washed with water and dried under reduced pressure to obtain 4 g of a modified resin (CR-1-BOC) as a black solid.

Moreover, the solubility of the obtained compound (CR-1-BOC) in a safe solvent was evaluated by the above measurement method. The results are shown in Table 1 (Comparative Example 2).

Examples and Comparative Examples (Preparation of Resist Composition)

A resist composition was prepared according to the formula shown in Table 1 below using each of the compounds synthesized in Synthesis Examples and Comparative Synthesis Examples. Among the components of the resist composition in Table 1, the following acid generating agent (C), acid crosslinking agent (G), acid diffusion controlling agent (E), and solvent (S-1) were used.

[Acid Generating Agent (C)]
  P-1: triphenylbenzenesulfonium trifluoromethanesulfonate (Midori Kagaku Co., Ltd.)

[Acid Diffusion Controlling Agent (E)]
  Q-1: trioctylamine (Tokyo Kasei Kogyo Co., Ltd.)

[Solvent]
  S-1: propylene glycol monomethyl ether acetate (Tokyo Kasei Kogyo Co., Ltd.)

The "storage stabilities" of the obtained resist compositions were evaluated by the above measurement method. Also, the "thin film formabilities" of the resist compositions in a homogeneous state were evaluated. The obtained results are shown in Table 1.

Furthermore, the solubilities of the compounds obtained in Synthesis Examples and Comparative Synthesis Examples in a safe solvent were evaluated by the above method. The results are shown in Table 1.

TABLE 1

| | | Composition for lithography | | | | | | | | | | |
|---|---|---|---|---|---|---|---|---|---|---|---|---|
| | | | Composition | | | | | Evaluation | | | | Pattern formation method |
| | | Safe solvent solubility test | Compound [g] | Acid generating agent (C) P-1 [g] | Acid crosslinking agent (G) C-1 [g] | Acid diffusion controlling agent (E) Q-1 [g] | Solvent S-1 [g] | Storage stability | Thin film formability | Sensitivity evaluation | Pattern formation | P = positive type N = negative type |
| Example 1 | BHPT | A | 0.75 | 0.3 | 0.25 | 0.03 | 50 | A | A | A | B | N |
| Example 2 | BHPT-ADBAC | A | 1 | 0.3 | — | 0.03 | 50 | A | A | A | A | P |
| Example 3 | BHPT-BOC | A | 1 | 0.3 | — | 0.03 | 50 | A | A | A | A | P |
| Example 4 | BHPT-EE | A | 1 | 0.3 | — | 0.03 | 50 | A | A | A | A | P |
| Example 5 | Ph-BHPT | A | 1 | 0.3 | — | 0.03 | 50 | A | A | A | A | P |
| Example 6 | TDP | A | 0.75 | 0.3 | 0.25 | 0.03 | 50 | A | A | A | B | N |
| Example 7 | Ph-TDP | A | 0.75 | 0.3 | 0.25 | 0.03 | 50 | A | A | A | A | N |
| Example 8 | Ph-BHPT-ADBAC | A | 1 | 0.3 | — | 0.03 | 50 | A | A | A | A | P |
| Example 9 | TDP-ADBAC | A | 1 | 0.3 | — | 0.03 | 50 | A | A | A | A | P |
| Example 10 | Ph-TDP-ADBAC | A | 1 | 0.3 | — | 0.03 | 50 | A | A | A | A | P |
| Example 11 | Ph-TDP-BOC | A | 1 | 0.3 | — | 0.03 | 50 | A | A | A | A | P |
| Example 12 | Ph-TDP-EE | A | 1 | 0.3 | — | 0.03 | 50 | A | A | A | A | P |
| Example 13 | R1-BHPT | A | 0.75 | 0.3 | 0.25 | 0.03 | 50 | A | A | A | A | N |
| Example 14 | R2-BHPT | A | 0.75 | 0.3 | 0.25 | 0.03 | 50 | A | A | A | A | N |
| Example 15 | R1-BHPT-ADBAC | A | 1 | 0.3 | — | 0.03 | 50 | A | A | A | A | P |
| Example 16 | R2-BHPT-ADBAC | A | 1 | 0.3 | — | 0.03 | 50 | A | A | A | A | P |
| Example 17 | R1-BHPT-BOC | A | 1 | 0.3 | — | 0.03 | 50 | A | A | A | A | P |
| Example 18 | R2-BHPT-BOC | A | 1 | 0.3 | — | 0.03 | 50 | A | A | A | A | P |
| Example 19 | R1-BHPT-EE | A | 1 | 0.3 | — | 0.03 | 50 | A | A | A | A | P |
| Example 20 | R2-BHPT-EE | A | 1 | 0.3 | — | 0.03 | 50 | A | A | A | A | P |
| Example 21 | R1-Ph-BHPT | A | 0.75 | 0.3 | 0.25 | 0.03 | 50 | A | A | A | A | N |
| Example 22 | R2-Ph-BHPT | A | 0.75 | 0.3 | 0.25 | 0.03 | 50 | A | A | A | A | N |
| Example 23 | R1-TDP | A | 0.75 | 0.3 | 0.25 | 0.03 | 50 | A | A | A | A | N |
| Example 24 | R2-TDP | A | 0.75 | 0.3 | 0.25 | 0.03 | 50 | A | A | A | A | N |
| Example 25 | R1-Ph-TDP | A | 0.75 | 0.3 | 0.25 | 0.03 | 50 | A | A | A | A | N |
| Example 26 | R2-Ph-TDP | A | 0.75 | 0.3 | 0.25 | 0.03 | 50 | A | A | A | A | N |

TABLE 1-continued

| | | Composition for lithography | | | | | | | | | | |
|---|---|---|---|---|---|---|---|---|---|---|---|---|
| | | | | Composition | | | | | Evaluation | | | Pattern formation method |
| | | Safe solvent solubility test | Compound [g] | Acid generating agent (C) P-1 [g] | Acid cross-linking agent (G) C-1 [g] | Acid diffusion controlling agent (E) Q-1 [g] | Solvent S-1 [g] | Storage stability | Thin film formability | Sensitivity evaluation | Pattern formation | P = positive type N = negative type |
| Example 27 | R1-Ph-BHPT-ADBAC | A | 1 | 0.3 | — | 0.03 | 50 | A | A | A | A | P |
| Example 28 | R2-Ph-BHPT-ADBAC | A | 1 | 0.3 | — | 0.03 | 50 | A | A | A | A | P |
| Example 29 | R1-TDP-ADBAC | A | 1 | 0.3 | — | 0.03 | 50 | A | A | A | A | P |
| Example 30 | R2-TDP-ADBAC | A | 1 | 0.3 | — | 0.03 | 50 | A | A | A | A | P |
| Example 31 | R1-Ph-TDP-ADBAC | A | 1 | 0.3 | — | 0.03 | 50 | A | A | A | A | P |
| Example 32 | R2-Ph-TDP-ADBAC | A | 1 | 0.3 | — | 0.03 | 50 | A | A | A | A | P |
| Example 33 | BHPT-co-ADTBA | A | 1 | 0.3 | — | 0.03 | 50 | A | A | A | A | P |
| Example 34 | TDP-co-ADTBA | A | 1 | 0.3 | — | 0.03 | 50 | A | A | A | A | P |
| Example 35 | DMB-co-TeCl2—OH | A | 0.75 | 0.3 | 0.25 | 0.03 | 50 | A | A | A | A | N |
| Example 36 | Re-co-Te | A | 0.75 | 0.3 | 0.25 | 0.03 | 50 | A | A | A | A | N |
| Example 37 | DMB-co-TeCl2-ADBAC | A | 1 | 0.3 | — | 0.03 | 50 | A | A | A | A | P |
| Example 38 | Re-co-Te-ADBAC | A | 1 | 0.3 | — | 0.03 | 50 | A | A | A | A | P |
| Example 39 | DPE-co-Te | A | 0.75 | 0.3 | 0.25 | 0.03 | 50 | A | A | A | A | N |
| Example 40 | Te-containing hyperbranched polymer | A | 1 | 0.3 | — | 0.03 | 50 | A | A | A | C | P |
| Comparative Example 1 | CR-1 | A | 0.75 | 0.3 | 0.25 | 0.03 | 50 | A | A | C | C | N |
| Comparative Example 2 | CR-1-BOC | A | 1 | 0.3 | — | 0.03 | 50 | A | A | C | C | P |

As can be understood from Table 1, the compounds used in Examples 1 to 40 (the compounds synthesized in Synthesis Examples 1 to 40) were able to be confirmed to have excellent solubility at the same level as in the compounds used in Comparative Examples 1 and 2 (the compounds synthesized in Comparative Synthesis Examples 1 and 2).

As a result of evaluating thin film formability according to the above measurement method, the resist compositions obtained in Examples 1 to 40 were able to form an excellent thin film at the same level as in Comparative Examples 1 and 2.

Pattern evaluation (sensitivity and pattern shape evaluation) was carried out by the above measurement method using the resist compositions obtained in Examples 1 and 2. In Examples 1 to 39, a good negative type or positive type resist pattern was obtained by irradiation with electron beams of 1:1 line and space setting with a 50 nm interval. As can also be understood from comparison with Comparative Examples 1 and 2, the resist compositions obtained in Examples 1 to 39 were excellent in both sensitivity and pattern shape. The resist composition obtained in Example 40 was excellent in sensitivity.

From the above results, it was found that the compounds meeting the requirements of the present invention have high solubility in safe solvents, and, also, resist compositions containing the compounds have good storage stability, thin film formability, and high sensitivity and can impart an excellent shape to a resist pattern, as compared with resist compositions containing the comparative compounds (CR-1 and CR-1-BOC). As long as the above requirements of the present invention are met, compounds other than the compounds described in Examples also exhibit the same effects.

Production of PGMEA Solution of Compound Represented by Formula (A) Having Reduced Metal Content Example 41

To a 4-neck flask (bottom-less type) having a volume of 1000 mL, 150 g of a solution (2.5% by mass) containing BHPT obtained in Synthesis Example 1 dissolved in PGMEA was fed, and heated to 80° C. while being stirred. Next, 37.5 g of an aqueous oxalic acid solution (pH 1.3) was added, and the mixture was stirred for 5 minutes and then left to stand still for 30 minutes. Accordingly, the mixture was separated into an oil phase and an aqueous phase, and the aqueous phase was removed. After this operation was repeated once, 37.5 g of ultrapure water was fed to the obtained oil phase, and the mixture was stirred for 5 minutes and then left to stand still for 30 minutes to remove the aqueous phase. By repeating this operation 3 times, a PGMEA solution of BHPT having a reduced metal content was obtained.

Example 42

A PGMEA solution of BHPT was obtained in the same manner as in Example 41 except that 150 g of PGMEA (120 g)/PGME (15 g) (10% by mass) was fed in place of 150 g of PGMEA (2.5% by mass).

Example 43

A PGMEA solution of BHPT was obtained in the same manner as in Example 42 except that 130 g of an aqueous citric acid solution (pH 1.8) was fed in place of 37.5 g of an aqueous oxalic acid solution (pH 1.3).

Example 44

To a 4-neck flask (bottom-less type) having a volume of 1000 mL, 150 g of a solution (2.5% by mass) containing BHPT-ADBAC obtained in Synthesis Example 2 dissolved in PGMEA was fed, and heated to 80° C. while being stirred. Next, 37.5 g of an aqueous oxalic acid solution (pH 1.3) was added, and the mixture was stirred for 5 minutes and then left to stand still for 30 minutes. Accordingly, the mixture was separated into an oil phase and an aqueous phase, and the aqueous phase was removed. After this operation was repeated once, 37.5 g of ultrapure water was fed to the obtained oil phase, and the mixture was stirred for 5 minutes and then left to stand still for 30 minutes to remove the aqueous phase. By repeating this operation 3 times, a PGMEA solution of BHPT-ADBAC having a reduced metal content was obtained.

Example 45

A PGMEA solution of BHPT-ADBAC was obtained in the same manner as in Example 44 except that 150 g of PGMEA (120 g)/PGME (15 g) (10% by mass) was fed in place of 150 g of PGMEA (2.5% by mass).

Example 46

A PGMEA solution of BHPT-ADBAC was obtained in the same manner as in Example 45 except that 130 g of an aqueous citric acid solution (pH 1.8) was fed in place of 37.5 g of an aqueous oxalic acid solution (pH 1.3).
(Evaluation)

The contents of various metals in the 10% by mass PGMEA solution of BHPT that was before treatment, in the 10% by mass PGMEA solution of BHPT-ADBAC that was before treatment, and in the solutions of Examples 43 to 48 were measured by ICP-MS. The measurement results are shown in Table 2.

TABLE 2

| | Metal content (ppb) | | | | | |
|---|---|---|---|---|---|---|
| | Na | Mg | K | Fe | Cu | Zn |
| BHPT before treatment | 37 | 1.3 | 1.4 | >99 | 2 | 12.4 |
| BHPT-ADBAC before treatment | 46 | 1.5 | 52 | >99 | 2.4 | 16.4 |
| Example 41 | ≤0.2 | ≤0.2 | ≤0.2 | ≤0.2 | ≤0.2 | ≤0.2 |
| Example 42 | ≤0.2 | ≤0.2 | ≤0.2 | ≤0.2 | ≤0.2 | ≤0.2 |
| Example 43 | ≤0.2 | ≤0.2 | ≤0.2 | ≤0.2 | ≤0.2 | ≤0.2 |
| Example 44 | ≤0.2 | ≤0.2 | ≤0.2 | ≤0.2 | ≤0.2 | ≤0.2 |
| Example 45 | ≤0.2 | ≤0.2 | ≤0.2 | ≤0.2 | ≤0.2 | ≤0.2 |
| Example 46 | ≤0.2 | ≤0.2 | ≤0.2 | ≤0.2 | ≤0.2 | ≤0.2 |

As can be understood from Table 2, the solutions of Examples 43 to 48 purified by the purification method of the present invention had an effectively reduced metal content with respect to the 10% by mass PGMEA solution of BHPT that was before treatment and the 10% by mass PGMEA solution of BHPT-ADBAC that was before treatment.

The resist composition of the present invention contains a compound having a specific structure and having high sensitivity and high solubility in safe solvents, has good storage stability and thin film formability, and can impart a good shape to a resist pattern. Accordingly, the present invention is useful in the semiconductor field, the display field, photomasks, thin film magnetic heads, compound semiconductors, research and development, and the like where resist compositions such as acid-amplified non-polymeric resist materials are used.

Also, according to the present invention, a compound or a resin (for example, a polyphenol derivative) having high sensitivity, high solubility in a safe solvent, good storage stability, and thin film formability can be provided. Accordingly, the present invention is suitably used for a base material of photosensitive materials such as photoresists for semiconductors, a raw material or a curing agent of an epoxy resin used for, for example, encapsulating materials of integrated circuits, a color developer or a discoloration inhibitor used for heat-sensitive recording materials, and, in addition, an additive for germicides and antimicrobial/antifungal agents, etc.

Moreover, by using the purification method of the present invention, a compound represented by the formula (A) or a resin comprising a constitutional unit derived from the compound represented by the formula (A) having a reduced metal content can be produced in an industrially advantageous manner.

The disclosure of Japanese Patent Application No. 2015-0165305 filed on Aug. 24, 2015 is incorporated herein by reference in its entirety.

All literatures, patent applications, and technical standards described herein are incorporated herein by referent to the same extent as if each individual literature, patent application, or technical standard is specifically and individually indicated to be incorporated by reference.

The invention claimed is:

1. A composition for forming a film for lithography comprising:
a tellurium-containing compound or a tellurium-containing resin, the tellurium-containing compound or the tellurium-containing resin having an aryl structure which includes a hydroxy group or a group in which a hydrogen atom of a hydroxy group is substituted with an acid crosslinking reactive group or an acid dissociation reactive group, the tellurium-containing compound being represented by the following formula (A-2) and the tellurium-containing resin being a resin comprising a constitutional unit represented by at least one of the following formulae (C1) and (C2):

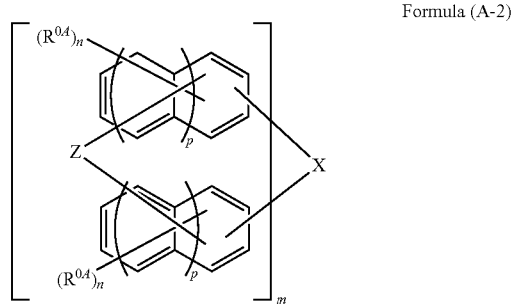

Formula (A-2)

wherein X is a 2m-valent group of 0 to 60 carbon atoms containing tellurium; Z is an oxygen atom, a sulfur atom, a single bond, or is not present; each $R^{O4}$ is independently selected from the group consisting of a hydrocarbon group, a halogen atom, a cyano group, a nitro group, an amino group, an alkyl group of 1 to 30 carbon atoms, an alkenyl group of 2 to 30 carbon atoms, an aryl group of 6 to 40 carbon atoms, a hydroxy group or a group in which a hydrogen atom of a hydroxy group is substituted with an acid crosslinking reactive group or an acid dissociation reactive group, and a combination thereof, wherein the alkyl group, the alkenyl group, and the aryl group each optionally have an ether bond, a ketone bond, or an ester bond, wherein at least one $R^{O.4}$ is a hydroxy or a group in which a hydrogen atom of a hydroxy group is substituted with an acid crosslinking reactive group or an acid dissociation reactive group; m is an integer of 1 to 4; each p is independently an integer of 0 to 2; and each n is independently an integer of 0 to (5+2×p),

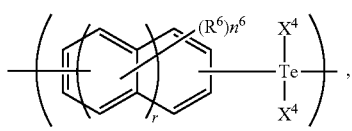

Formula (C1)

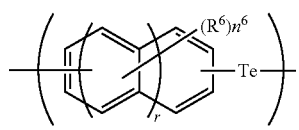

Formula (C2)

wherein each $X^4$ is independently a monovalent group containing an oxygen atom, a monovalent group containing a sulfur atom, a monovalent group containing a nitrogen atom, a hydrocarbon group, a hydrogen atom, or a halogen atom; each $R^6$ is independently a monovalent group containing an oxygen atom, a monovalent group containing a sulfur atom, a monovalent group containing a nitrogen atom, a hydrocarbon group, or a halogen atom; r is an integer of 0 to 2; and $n^6$ is an integer of 2 to (4+2×r);

a solvent; and an acid generating agent, the acid generating agent being a compound other than the tellurium-containing compound or the tellurium-containing resin, the acid generating agent generates an acid directly or indirectly by irradiation of any radiation selected from visible light, ultraviolet, excimer laser, electron beam, extreme ultraviolet (EUV), X-ray, and ion beam.

2. The composition for forming a film for lithography according to claim 1, wherein the tellurium-containing resin is a resin comprising a constitutional unit represented by the following formula (C1):

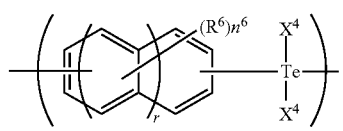

Formula (C1)

wherein each $X^4$ is independently a monovalent group containing an oxygen atom, a monovalent group containing a sulfur atom, a monovalent group containing a nitrogen atom, a hydrocarbon group, a hydrogen atom, or a halogen atom; each $R^6$ is independently a monovalent group containing an oxygen atom, a monovalent group containing a sulfur atom, a monovalent group containing a nitrogen atom, a hydrocarbon group, or a halogen atom; r is an integer of 0 to 2; and $n^6$ is an integer of 2 to (4+2×r).

3. The composition for forming a film for lithography according to claim 1, wherein the tellurium-containing resin is a resin comprising a constitutional unit represented by the following formula (C2):

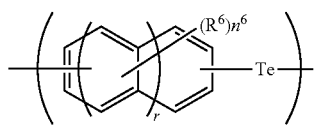

Formula (C2)

wherein each $R^6$ is independently a monovalent group containing an oxygen atom, a monovalent group containing a sulfur atom, a monovalent group containing a nitrogen atom, a hydrocarbon group, or a halogen atom; r is an integer of 0 to 2; and $n^6$ is an integer of 2 to (4+2×r).

4. The composition for forming a film for lithography according to claim 1, further comprising an acid crosslinking agent.

5. A resin comprising a constitutional unit represented by the following formula (B1-M'):

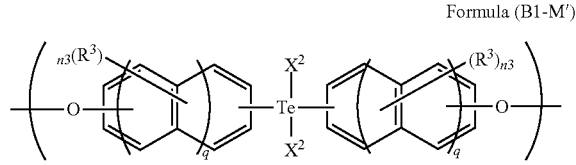

Formula (B1-M')

wherein each $X^2$ is independently a monovalent group containing an oxygen atom, a monovalent group containing a sulfur atom, a monovalent group containing a nitrogen atom, a hydrocarbon group, a hydrogen atom, or a halogen atom, and if an $X^2$ includes a halogen atom, at least one $X^2$ is selected from the group consisting of fluorine, iodine, and bromine; each $R^3$ is independently a monovalent group containing an oxygen atom, a monovalent group containing a sulfur atom, a monovalent group containing a nitrogen atom, a hydrocarbon group, or a halogen atom; q is an integer of 0 to 2; and $n^3$ is an integer of 0 to (4+2×q).

6. A resin comprising a constitutional unit represented by the following formula (B2-M):

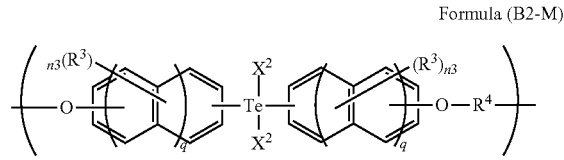

Formula (B2-M)

wherein each $X^2$ is independently a monovalent group containing an oxygen atom, a monovalent group containing a sulfur atom, a monovalent group containing a nitrogen atom, a hydrocarbon group, a hydrogen atom, or a halogen atom, and if an $X^2$ includes a halogen atom, at least one $X^2$ is selected from the group consisting of fluorine, iodine, and bromine; each $R^3$ is independently a monovalent group containing an oxygen atom, a monovalent group containing a sulfur atom, a monovalent group containing a nitrogen atom, a hydrocarbon group, or a halogen atom; q is an integer of 0 to 2; $n^3$ is an integer of 0 to (4+2×q); and $R^4$ is any structure represented by the following formula (5):

Formula (5)

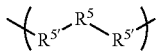

Formula (5')

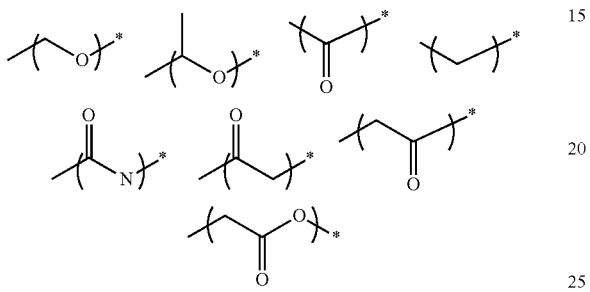

wherein $R^5$ is a substituted or unsubstituted linear alkylene group of 1 to 20 carbon atoms, branched alkylene group of 3 to 20 carbon atoms, or cyclic alkylene group of 3 to 20 carbon atoms, or a substituted or unsubstituted arylene group of 6 to 20 carbon atoms; each $R^{5'}$ is independently any structure of the above formula (5') wherein * indicates that this portion is connected to $R^5$.

7. A resin comprising a constitutional unit represented by the following formula (B2-M'):

Formula (B2-M')

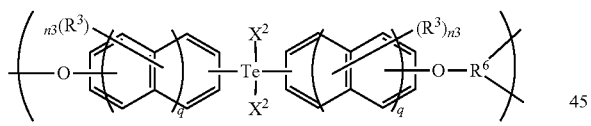

wherein each $X^2$ is independently a monovalent group containing an oxygen atom, a monovalent group containing a sulfur atom, a monovalent group containing a nitrogen atom, a hydrocarbon group, a hydrogen atom, or a halogen atom; each $R^3$ is independently a monovalent group containing an oxygen atom, a monovalent group containing a sulfur atom, a monovalent group containing a nitrogen atom, a hydrocarbon group, or a halogen atom; q is an integer of 0 to 2; $n^3$ is an integer of 0 to (4+2×q); and $R^6$ is any structure represented by the following formula (6):

Formula (6)

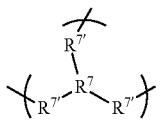

-continued

Formula (6')

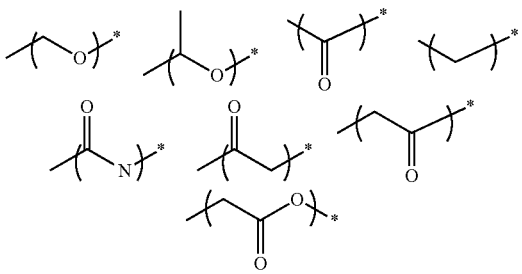

wherein $R^7$ is a substituted or unsubstituted linear alkylene group of 1 to 20 carbon atoms, branched alkylene group of 3 to 20 carbon atoms, or cyclic alkylene group of 3 to 20 carbon atoms, or a substituted or unsubstituted arylene group of 6 to 20 carbon atoms; each $R^{7'}$ is independently any structure of the above formula (6') wherein * indicates that this portion is connected to $R^7$.

8. A resin comprising a constitutional unit represented by the following formula (B3-M'):

Formula (B3-M')

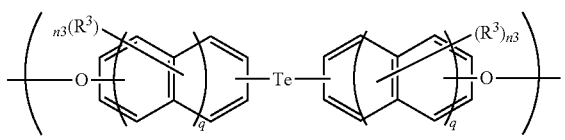

wherein each $R^3$ is independently a monovalent group containing an oxygen atom, a monovalent group containing a sulfur atom, a monovalent group containing a nitrogen atom, a hydrocarbon group, or a halogen atom; q is an integer of 0 to 2; and $n^3$ is an integer of 1 to (4+2×q).

9. A resin comprising a constitutional unit represented by the following formula (B4-M):

Formula (B4-M)

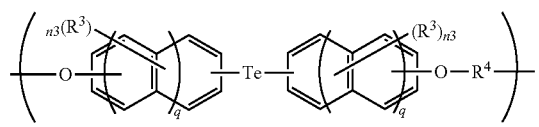

wherein each $R^3$ is independently a monovalent group containing an oxygen atom, a monovalent group containing a sulfur atom, a monovalent group containing a nitrogen atom, a hydrocarbon group, or a halogen atom; q is an integer of 0 to 2; $n^3$ is an integer of 1 to (4+2×q); and $R^4$ is any structure represented by the following formula (5):

Formula (5)

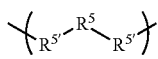

-continued

Formula (5')

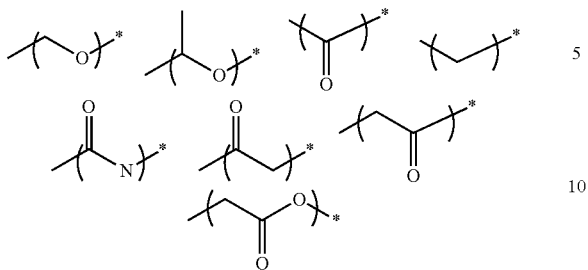

wherein $R^5$ is a substituted or unsubstituted linear alkylene group of 1 to 20 carbon atoms, branched alkylene group of 3 to 20 carbon atoms, or cyclic alkylene group of 3 to 20 carbon atoms, or a substituted or unsubstituted arylene group of 6 to 20 carbon atoms; each $R^{5'}$ is independently any structure of the above formula (5') wherein * indicates that this portion is connected to $R^5$.

10. A resin comprising a constitutional unit represented by the following formula (B4-M'):

Formula (B4-M')

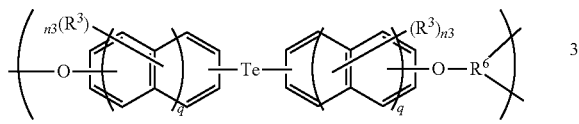

wherein each $R^3$ is independently a monovalent group containing an oxygen atom, a monovalent group containing a sulfur atom, a monovalent group containing a nitrogen atom, a hydrocarbon group, or a halogen atom; q is an integer of 0 to 2; $n^3$ is an integer of 0 to (4+2×q); and $R^6$ is any structure represented by the following formula (6):

Formula (6)

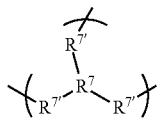

-continued

Formula (6')

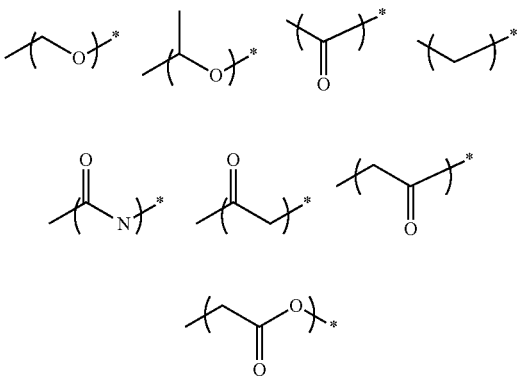

wherein $R^7$ is a substituted or unsubstituted linear alkylene group of 1 to 20 carbon atoms, branched alkylene group of 3 to 20 carbon atoms, or cyclic alkylene group of 3 to 20 carbon atoms, or a substituted or unsubstituted arylene group of 6 to 20 carbon atoms; each $R^{7'}$ is independently any structure of the above formula (6') wherein * indicates that this portion is connected to $R^7$.

11. A resin comprising a constitutional unit represented by the following formula (C2):

Formula (C2)

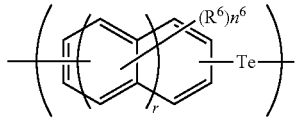

wherein each $R^6$ is independently a monovalent group containing an oxygen atom, a monovalent group containing a sulfur atom, a monovalent group containing a nitrogen atom, a hydrocarbon group, or a halogen atom, wherein at least one $R^6$ is a hydroxy group or a group in which a hydrogen atom of a hydroxy group is substituted with an acid crosslinking reactive group or an acid dissociation reactive group; r is an integer of 0 to 2; and $n^6$ is an integer of 2 to (4+2×r).

* * * * *

UNITED STATES PATENT AND TRADEMARK OFFICE
CERTIFICATE OF CORRECTION

| | | |
|---|---|---|
| PATENT NO. | : 11,852,970 B2 | Page 1 of 1 |
| APPLICATION NO. | : 15/754794 | |
| DATED | : December 26, 2023 | |
| INVENTOR(S) | : Hiroto Kudo et al. | |

It is certified that error appears in the above-identified patent and that said Letters Patent is hereby corrected as shown below:

On the Title Page

In Item (56), under "OTHER PUBLICATIONS", in Column 2, Line 44, delete "sulfer" and insert -- sulfur --, therefor.

In Item (56), under "OTHER PUBLICATIONS", in Column 2, Line 58, delete "Compunds" and insert -- Compounds --, therefor.

Signed and Sealed this
Twenty-third Day of July, 2024

Katherine Kelly Vidal
*Director of the United States Patent and Trademark Office*